US009144585B2

(12) United States Patent
Itskovitz-Eldor et al.

(10) Patent No.: US 9,144,585 B2
(45) Date of Patent: Sep. 29, 2015

(54) ISOLATED MESENCHYMAL PROGENITOR CELLS AND EXTRACELLULAR MATRIX PRODUCED THEREBY

(75) Inventors: Joseph Itskovitz-Eldor, Haifa (IL); Ronit Shtrichman, Haifa (IL); Eyal Zussman, Haifa (IL); Efrat Barak, Nofit (IL)

(73) Assignee: Technion Research & Development Foundation Limited, Haifa (IL)

( * ) Notice: Subject to any disclaimer, the term of this patent is extended or adjusted under 35 U.S.C. 154(b) by 0 days.

(21) Appl. No.: 13/812,552

(22) PCT Filed: Jul. 27, 2011

(86) PCT No.: PCT/IL2011/000604

§ 371 (c)(1),
(2), (4) Date: Jan. 28, 2013

(87) PCT Pub. No.: WO2012/014205

PCT Pub. Date: Feb. 2, 2012

(65) Prior Publication Data

US 2013/0230601 A1 Sep. 5, 2013

Related U.S. Application Data

(60) Provisional application No. 61/367,933, filed on Jul. 27, 2010, provisional application No. 61/432,207, filed on Jan. 13, 2011.

(51) Int. Cl.
*A61K 35/12* (2015.01)
*C12N 5/0775* (2010.01)

(52) U.S. Cl.
CPC .............. *A61K 35/12* (2013.01); *C12N 5/0662* (2013.01); *C12N 2506/02* (2013.01); *C12N 2506/45* (2013.01); *C12N 2509/00* (2013.01)

(58) Field of Classification Search
CPC ... A61K 35/545; A61K 35/12; C12N 5/0696; C12N 5/0662; C12N 2506/02; C12N 2509/00; C12N 2506/45
USPC ........................... 435/366, 402, 377; 424/572
See application file for complete search history.

(56) References Cited

U.S. PATENT DOCUMENTS

| | | | |
|---|---|---|---|
| 2001/0024825 | A1 | 9/2001 | Thomson |
| 2005/0181004 | A1 | 8/2005 | Hunter et al. |
| 2006/0293743 | A1 | 12/2006 | Andersen et al. |
| 2009/0138070 | A1 | 5/2009 | Holzer et al. |
| 2010/0129450 | A1 | 5/2010 | Atala et al. |
| 2010/0185219 | A1 | 7/2010 | Gertzman et al. |
| 2011/0135806 | A1 | 6/2011 | Grewe et al. |
| 2013/0030452 | A1 | 1/2013 | Itskovitz-Eldor et al. |
| 2013/0130387 | A1 | 5/2013 | Itskovitz-Eldor et al. |

FOREIGN PATENT DOCUMENTS

| | | |
|---|---|---|
| EP | 1674048 | 6/2006 |
| WO | WO 2005/111197 | 11/2005 |
| WO | WO 2007/080590 | 7/2007 |
| WO | WO 2007/080591 | 7/2007 |
| WO | WO 2009/019685 | 2/2009 |
| WO | WO 2009/098698 | 8/2009 |
| WO | WO 2010/042490 | 4/2010 |
| WO | WO 2010/077955 | 7/2010 |
| WO | WO 2011/003422 | 1/2011 |
| WO | WO 2012/014205 | 2/2012 |
| WO | WO 2012/014207 | 2/2012 |
| WO | WO 2012/014605 | 2/2012 |

OTHER PUBLICATIONS

Chen et al. "Extracellular matrix made by bone marrow cells facilitates expansion of marrow-derived mesenchymal progenitor cells and prevents their differentiation into osteoblasts", Journal of Bone and Mineral Research 22(12): 1943-56, 2007.*

Pereira et al. "Cultured adherent cells from marrow can serve as long-lasting precursor cells for bone, cartilage, and lung in irradiated mice", PNAS 92: 4857-61, 1995.*

Barberi et al., PLoS Medicine, 2(6), e161: 0554-0560, 2005.*

Poloni et al., Cytotherapy, 10(7): 690-697, 2008.*

International Preliminary Report on Patentability Dated Feb. 7, 2013 From the International Bureau of WIPO Re. Application No. PCT/IL2011/000604.

International Preliminary Report on Patentability Dated Feb. 7, 2013 From the International Bureau of WIPO Re. Application No. PCT/IL2011/000606.

Communication Pursuant to Rules 70(2) and 70a(2) EPC and Reference to Rule 39(1) EPC Dated Feb. 4, 2013 From the European Patent Office Re. Application No. 12178076.1.

Communcialion Pursuant to Article 94(3) EPC Dated Jan. 6, 2014 From the European Patent Office Re. Application No. 12178076.1.

Corrected International Search Report and the Written Opinion Dated Apr. 5, 2012 From the International Searching Authority Re. Application No. PCT/IL2011/000606.

European Search Report and the European Search Opinion Dated Oct. 24, 2012 From the European Patent Office Re. Application No. 12178076.1.

International Search Report and the Written Opinion Dated Dec. 9, 2011 From the International Searching Authority Re. Application No. PCT/IL2011/000604.

(Continued)

*Primary Examiner* — Thaian N Ton

(57) ABSTRACT

Provided are methods of isolating an extracellular matrix from mesenchymal progenitor cells which are characterized by a reduced differentiation ability into an adipogenic lineage as compared to adipose-derived mesenchymal stem cells. Also provide isolated extracellular matrix and hybrid devices comprising electrospun elements and extracellular matrix which can be used for various tissue regeneration, repair and reconstruction surgeries.

15 Claims, 23 Drawing Sheets
(20 of 23 Drawing Sheet(s) Filed in Color)

(56) References Cited

OTHER PUBLICATIONS

International Search Report and the Written Opinion Dated Mar. 21, 2012 From the International Searching Authority Re. Application No. PCT/IL2011/000606.
Aasen et al. "Efficient and Rapid Generation of Induced Pluripotent Stem Cells From Human Keratinocytes", Nature Biotechnology, XP055019438, 26(11): 1276-1284, Nov. 1, 2008.
Aasen et al. "Isolation and Cultivation of Human Keratinocytes From Skin or Plucked Hair for the Generation of Induced Pluripotent Stem Cells", Nature Protocols, XP009156425, 5(2): 371-382, Jan. 1, 2010. Box 1, P.374, Box 4, P.378, P.380, Fig.5, P.382.
Badylak "Xenogeneic Extracellular Matrix as a Scaffold for Tissue Reconstruction", Transplant Immunology, 12: 367-377, 2004.
Badylak et al. "Extracellular Matrix as a Biological Scaffold Material: Structure and Function", Acta Biomaterialia, 5: 1-13, 2009.
Barbero et al. "Plasticity of Clonal Populations of Dedifferentiated Adult Human Articular Chondrocytes", Arthritus & Rheumatism, 48(5): 1315-1325, May 2003.
Bieback et al. "Critical Parameters for the Isolation of Mesenchymal Stem Cells From Umbilical Cord Blood", Stem Cells, 22: 625-634, 2004.
Chen et al. "Scaffolds for Tendon and Ligament Repair: Review of the Efficacy of Commercial Products", Expert Reviews in Medicinal Devices, 6(1): 61-73, 2009.
Chen et al. "Stepwise Differentiation of Human Embryonic Stem Cells Promotes Tendon Regeneration by Secreting Fetal Tendon Matrix and Differentiation Factors", Stem Cells, XP009154459, 27(6): 1276-1287, Jun. 2009. p. 1278.
Chin et al. "Induced Pluripotent Stem Cells and Embryonic Stem Cells Are Distinguished by Gene Expression Signatures", Cell Stem Cell, 5: 111-123, Jul. 2, 2009.
Cohen et al. "Repair of Full-Thickness Tendon Injury Using Connective Tissue Progenitors Efficiently Derived From Human Embryonic Stem Cells and Fetal Tissues", Tissue Engineering: Part A, 16(10): 3119-3137, 2010.
De Peppo et al. "Human Embryonic Mesodermal Progenitors Highly Resemble Human Mesenchymal Stem Cells and Display High Potential for Tissue Engineering Applications", Tissue Engineering, XP002658133, 16(7): 2161-2182, Jul. 1, 2010. Tables 1, 2.
De Vries et al. "Repair of Giant Midline Abdominal Wall Hernias: 'Components Separation Technique' Versus Prosthetic Repair. Interim Analysis of a Randomized Controlled Trial", World Journal of Surgery, 31: 756-763, Mar. 5, 2007.
Harkness et al. "Selective Isolation and Differentiation of a Stromal Population of Human Embryonic Stem Cells With Osteogenic Potential", Bone, XP027070835, 48(2): 231-241, Epub Sep. 30, 2010 & Supplementary Material. Abstract.
Iiu et al. "Memory in Induced Pluripotent Stem Cells: Reprogrammed Iluman Retinal Pigmented Epithelial Cells Show Tendency for Spontaneous Redifferentiation", Stem Cells, 28(11): 1981-1991, Nov. 2010.
Hui et al. "Mesenchymal Stem Cells in Musculoskeletal Tissue Engineering: A Review of Recent Advances in National University of Singapore", Annals of the Academy of Medicine, Singpore, XP009075343, 34*2): 206-212, Mar. 1, 2005.
Hwang et al. "In Vivo Commitment and Functional Tissue Regeneration Using Human Embryonic Stem Cell-Derived Mesenchymal Cells", Proc. Natl. Acad. Sci. USA, PNAS, 105(52): 20641-20646, Dec. 30, 2008.
Karlsson et al. "Human Embryonic Stem Cell-Derived Mesenchymal Progenitors-Potential in Regenerative Medicine", Stem Cell Research, XP002658132, 3(1): 3950, Jul. 1, 2009. p. 44-47.
Kiskinis et al. "Progress Toward the Clinical Application of Patient-Specific Pluripotent Stem Cells", The Journal of Clinical Investigation, 1200): 51-59, Jan. 2010.
Li et al. "Derivation of Murine Induced Pluripotent Stem Cells (iPS) and Assessment of Their Differentiation Toward Osteogenic Lineage", Journal of Cellular Biochemistry, 109: 643-652, 2010.
Li et al. "Generation of Human-Induced Pluripotent Stem Cells in the Absence of Exogenous Sox2", Stem Cells, XP055019594, 27: 2992-3000, 2009.
Lian et al. "Functional Mesenchymal Stem Cells Derived From Human Induced Pluripotent Stem Cells Attenuate Limb Ischemia in Mice", Circulation, 121: 1113-1123, Mar. 9, 2010.
Lim et al. "Electrospun Scaffolds for Stem Cell Engineering", Advanced Drug Delivery Reviews, 61: 1084-1096, 2009.
Novak et al. "Enhanced Reprogramming and Cardiac Differentiation of Human Keratinocytes Derived From Plucked Hair Follicles, Using A Single Excisable Lentivirus", Cellular Reprogramming, 12(6): 665-678 & Supplementary Material, 2010.
Reing et al. "Degradation Products of Extracellular Matrix Affect Cell Migration and Proliferation", Tissue Engineering: Part A, 15(3): 605-614, 2009.
Shen et al. "Construction of Ureteral Grafts by Seeding Urothelial Cells and Bone Marrow Mesenchymal Stem Cells Into Polycaprolactone-Lecithin Electrospun Fibers", The International Journal of Artificial Organs, 33(3): 161-170, 2010.
Thibault et al. "Osteogenic Differentiation of Mesenchymal Stem Cells on Pregenerated Extracellular Matrix Scaffolds in the Absence of Osteogenic Cell Culture Supplements", Tissue Engineering: Part A, 16(2): 431-440, 2010.
Van't Riet et al. "Mesh Repair for Postoperative Wound Dehiscence in the Presence of Infection: Is Absorbable Mesh Safer Than Non-Absorbable Mesh?", Hernia, 11: 409-413, 2007.
Wernig et al. "A Drug-Inducible Transgenic System for Direct Reprogramming of Multiple Somatic Cell Types", Nature Biotechnology, XP008148061, 26(8): 916-924, Aug. 1, 2008. Figs.la, 5g, Table 1.
Yamashita "ES and iPS Cell Research for Cardiovascular Regeneration", Experimental Cell Research, XP027264818, 316(16): 2555-2559, Apr. 10, 2010. p. 2557, r-h Col.- p. 2558, 1-h Col., p. 2558-Last Para.
Restriction Official Action Dated Sep. 10, 2014 From the US Patent and Trademark Office Re. U.S. Appl. No. 13/558,483.
Restriction Official Action Dated Apr. 29, 2014 From the US Patent and Trademark Office Re. U.S. Appl. No. 13/812,566.
Official Action Dated Jul. 10, 2014 From the US Patent and Trademark Office Re. U.S. Appl. No. 13/812,566.
Limat et al. "Serial Cultivation of Single Keratinocytes From the Outer Root Sheath of Human Scalp Hair Follicles", Journal of Investigative Dermatology, 87(4): 485-488, Oct. 1986.
RAI Consortium "Section III: Lentiviral Infection", The RAI Consortium, p. 1-4, Sep. 30, 2005.
Silva et al. "Promotion of Reprogramming to Ground State Pluripotency by Signal Inhibition", PLoS Biology, 6(10): c253-2237 - c253-2247, Oct. 2008.
Sommer et al. "Induced Pluripotent Stem Cell Generation Using a Single Lentiviral Stem Cell Cassette", Stem Cells, 27: 543-549, Mar. 2, 2009.
Official Action Dated Feb. 24, 2015 From the US Patent and Trademark Office Re. U.S. Appl. No. 13/812,566.
Cowan et al. "Derivation of Embryonic Stem-Cell Lines From Human Blastocysts", The New England Journal of Medicine, 350(13): 1353-1356, Mar. 25, 2004.
Maherali et al. "A High-Efficiency System for the Generation and Study of Human Induced Pluripotent Stem Cells", Cell Stem Cell, 3: 340-345, Sep. 11, 2008.
Reichelt et al. "Establishment of Spontaneously Immortalized Keratinocyte Lines From Wild-Type and Mutant Mice", Epidermal Cells, Methods in Molecular Biology, 585(Chap.5): 59-69, Oct. 7, 2009.
Official Action Dated Dec. 2, 2014 From the US Patent and Trademark Office Re. U.S. Appl. No. 13/558,483.

* cited by examiner

FIG. 1A (ii)
FIG. 1A (iii)

Cellular

H&E

TC

FN

A-Cellular

Synthetic mesh

NFL-ECM

SCID mouse implant

Rat implant

Synthetic mesh

NFL-ECM

SCID mouse implant

Rat implant

NFL- ECM

X5

NFL only

SCID mouse implant

Rat implant

X20

PLGA only

Live cells + PLGA

Acellular PLGA ECM

PLGA only

Live cells + PLGA

PLGA + acellular ECM

Net

Net-NFL

Net-NFL-ECM

Net implant

NFL implant

Net-NFL
no ECM

Net-NFL –ECM
(AD5T)

Net-NFL –ECM
(KTN7.3)

NET-NFL, No ECM
NET-NFL-ECM (AD5T)
NET-NFL-ECM (KTN.7.3)
TCx4
TCx4
TCx10

ISOLATED MESENCHYMAL PROGENITOR CELLS AND EXTRACELLULAR MATRIX PRODUCED THEREBY

RELATED APPLICATIONS

This application is a National Phase of PCT Patent Application No. PCT/IL2011/000604 having International filing date of Jul. 27, 2011, which claims the benefit of priority under 35 USC §119(e) of U.S. Provisional Patent Application Nos. 61/367,933 filed on Jul. 27, 2010 and 61/432,207 filed on Jan. 13, 2011. The contents of the above applications are all incorporated by reference as if fully set forth herein in their entirety.

SEQUENCE LISTING STATEMENT

The ASCII file, entitled 55709SequenceListing.txt, created on Jan. 20, 2013, comprising 138,805 bytes, submitted concurrently with the filing of this application is incorporated herein by reference.

FIELD AND BACKGROUND OF THE INVENTION

The present invention, in some embodiments thereof, relates to isolated cell populations comprising mesenchymal progenitor cells (MPCs), and more particularly, but not exclusively, to methods of generating same and using same for producing and isolating extracellular matrix which can be used for preparation of implantable devices for tissue regeneration and/or repair.

The aim of regenerative medicine is to repair or replace damaged or diseased tissue in the human body. Cell therapy based upon stem and progenitor cells have many distinct advantages and offer tremendous potential for regenerative medicine. The multipotency and proliferative nature of stem cells makes them a more reliable cell source than terminally differentiated cells. Stem cells have additional advantage of being relatively more immune-compatible cells. In addition, stem cells can proliferate well on a supportive scaffold, and their cell fate can be further controlled and directed by their interactions with the synthetic scaffold (Lim S H and Mao H Q, 2009, Advanced Drug Delivery Reviews, 61: 1084-1096).

Adult mesenchymal stem cells (MSCs) derived from either bone marrow or adipose tissues are multipotent cells that can differentiate into various lineages including osteogenic, chondrogenic and adipogenic lineages, and as such can be used to enhance repair of a variety of soft tissue defects. However, adult MSCs exhibit a limited capacity to proliferate, loss of differentiation potential and reduced protective factors during ex-vivo expansion before possible therapeutic use. In addition, adult stem cells isolated from different subjects exhibit remarkable variability. Moreover, while isolation of adult MSCs from a human body involves invasive procedures, aging and aging-related disorders significantly impair the survival and differentiation capacity of MSCs, thus limiting their therapeutic efficacy. Due to these limitations, adult stem cells are not suitable for "off the shelf product" such as for production of extracellular matrix (ECM).

Mesenchymal stem cell-like cells can be generated from pluripotent stem cells capable of differentiation into cells of all three embryonic germ layers (i.e., endoderm, mesoderm and ectoderm) such as human embryonic stem cells (hESCs) and human induced pluripotent stem cells (hiPSCs). In contrast to adult stem cells, pluripotent stem cells can potentially indefinitely proliferate, providing a large number of cells with specific characteristics needed for regenerative medicine protocols. However, the practical use of pluripotent stem cells as a source for ECM, requires the development of simple and efficient protocols to generate "easy to grow" cell populations that can produce functional ECM for regenerative medicine.

Harkness L et al. 2010 ("Selective isolation and differentiation of a stromal population of human embryonic stem cells with osteogenic potential". Bone Sep 30. Epub ahead of print) describe the direct differentiation of hESCs into stroma-like cells which differentiate into the osteogenic lineage while producing a mineralized matrix and into the adipogenic lineage while producing fat drops.

Hwang N S et al. 2008 (PNAS 105: 20641-20646) describe derivation of hESCs to MSCs capable of producing fat, cartilage and bone in vitro.

Induced pluripotent stem cells (iPSCs) are somatic cells that have been reprogrammed into a pluripotent state resembling that of human embryonic stem cells (hESCs). Patient-specific iPSCs can provide useful platforms for the discovery of new drugs, as well as unprecedented insights into disease mechanisms that ultimately may be used to develop cell and tissue replacement therapies (Kiskinis E, and Eggan K. J. Clin. Investigation, 120: 51-59, 2010). Human iPSCs (hiPSCs) have been generated from various types of somatic cells, most commonly fibroblasts that are isolated from tissues harvested via surgical intervention.

Novak et al., 2010 [Cell Reprogram. 2010, 12(6): 665-78)] describe the derivation of hiPSCs from plucked human hair follicle keratinocytes (HFKTs) which spontaneously differentiated into functional cardiomyocytes (CMs).

Lian Q et al., 2010 (Circulation. 121:1113-1123) have recently demonstrated the differentiation potential of hiPSCs into functional MSCs, using single cell sorting of $CD105^+$/$CD24^-$ of differentiating hiPSCs. The resulting MSCs were capable of differentiation into adipogenic, osteogenic and chondrogenic lineages.

Li F. et al., 2010 (JCB 109: 643-652), describe the differentiation of murine iPSCs towards MSC-like cells by treating iPSC-derived-EBs with transforming growth factor beta-1 (TGFβ1) and retinoic acid. The resulting cells expressed putative MSCs markers and deposited calcium in vitro when cultured in an osteogenic medium.

WO/2007/080590 provides methods of generating multipotent connective tissue progenitor cells (CTPs) from embryonic stem cells and embryoid bodies. The CTPs population included 40-60% of CD105-positive cells.

WO/2007/080591 provides methods of generating multipotent connective tissue progenitor cells (CTPs) from adult stem cells.

The extracellular matrix (ECM) is a secreted product of cells that populate in a given tissue or organ. The ECM influences the behavior and phenotype of the resident cells. Cell attachment, migration, proliferation and three-dimensional arrangement are strongly affected by matrix composition and structure. The main advantages of using ECM scaffolds are their bioactivity and biocompatibility capabilities.

ECM composition includes the most abundant protein—type I Collagen, as well as fibronectin and laminin. Other substantial components are glycosaminoglycans, as chrondrotin sulfate, heparin and hyaluronic acid, which have superior binding properties of bioactive molecules as growth factors and cytokines. Growth factors, such as vascular endothelial growth factor (VEGF), fibroblast growth factor (FGF), epidermal growth factor (EGF), and TGFβ, are present within the ECM in very small quantities but play a critical role as potent modulators of cell behavior. Individual components of the ECM, such as collagen I or fibronectin have been used as alternative scaffold materials, but were found to be less bioactive than the whole intact ECM.

ECMs for clinical applications are currently derived from organs such as the small intestine, urinary bladder or skin (Reing J., et al. 2009, Tissue Engineering, Vol. 15: 605-614' Badylak S F. 2004. Transplant Immunology 12: 367-377), from allogeneic (human cadavers) or xenogeneic sources (porcine, bovine or equine small intestine submucosa, dermis and pericardium). Both cellular and acellular forms of ECM scaffolds have been used for tissue engineering applications. While the cellular form requires an autologous cell source, which is limited and may lead to patient's diminished functionality, the acellular form requires tissue processing, including elimination of all intact cells and degradation of nucleic acids, leaving only the ECM's proteins and growth factors biologically active. An example of a biological scaffold made of human cadaver is the GraftJacket™ product (Wright Medical Technology, TN, USA).

The ultimate goal in decellularizing a tissue, composed predominantly of Collagen fibers, is to remove any non-collagen components that may cause host rejection. However, in many cases the decellularization process is not complete and the scaffold includes traces of animal compounds, which elicit a significant inflammation response. In addition, cadaver donors are limited, thus scaffold made of this source are non-homogeneous, and non-reproducible. In addition, since derived from a human source, these scaffolds still exhibit the risk of pathogen transfer.

ECM mineralization is a physiologic process in bone, teeth, and hypertrophic cartilage, whereas in other locations it must be inhibited. Mineralization imparts important biomechanical and other functional properties to bones and teeth.

Synthetic scaffolds are manufactured from chemical compounds such as polyester, polypropylene, dacron, silicon and nylon fabric. Although they possess superior mechanical characteristics, they can never be integrated into the host tissue, and their poor biocompatibility causes numerous long-term complications, such as severe infections, chronic immune response and potential toxic byproducts (Chen J. et al. Expert Rev. Med. Devices, 2009, 6: 61-73).

Electrospinning can produce a macroporous scaffold comprising randomly oriented or aligned nanofibers. Electrospun polymeric fibrous meshes also offer a higher surface area for cell attachment and are relatively reproducible (Lim S H and Mao H Q, 2009; Adv. Drug. Del. Rev. 61:1084-1096).

Thibault R A et al. (Tissue Engineering, 2010, 16: 431-440) describe generation of a decellularized mineralized matrix from electrospun PCL fiber mesh scaffolds which were seeded with rat mesenchymal stem cells (MSCs) and cultured in a complete osteogenic medium.

WO/2009/098698 describes scaffolds composed of extracts of cellular and/or extracellular compartments for use in tissue regeneration.

The challenge in any reconstructive procedure is to provide a supporting structure while restoring the normal anatomic condition of the surrounding tissues. Though several materials can potentially provide the mechanical support, they do not possess the properties necessary to restore the living tissue's original quality.

Abdominal ventral hernia and pelvic floor defect (PFD) are common and challenging conditions for surgeons. It is estimated that 250,000 hernia repair and 300,000 procedures of prolapse and urinary incontinence surgeries are performed each year in the US. However, in about 12.5% of the hernia repair and 29% of the pelvic prolapse repairs repeated surgeries are needed within 5 years of initial surgery, mainly due to infection, seroma, wound dehiscence and formation of enterocutaneous fistula.

Synthetic meshes made of polypropylene and polyester are used for reconstructive surgeries (e.g., the Gyncare Prolift, Ethicon®, Johnson & Johnson, USA). Although the synthetic meshes are available and can simplify the operative procedure, reduce patient discomfort from an additional incision site and decrease operative time, in about 2.8-17.3% of the cases these meshes cause foreign-body reaction with risks of infection, rejection, visceral adhesion to the repair site, erosion to the bowel, urinary bladder and vaginal mucosa leading to enterocutaneous fistula, bowel obstruction and urinary bladder complications, extrusion of the repair material and infection. Infected synthetic repair material often necessitates surgical removal, leaving a contaminated field and a hernia deficit larger than the original (van't Riet M, et al., 2007. Hernia. 11:409-13; de Vries Reilingh T S, et al., 2007, World J. Surg. 31:756-63).

Additional background art includes Chin M H, et al., 2009 (CELL STEM CELL 5: 111-123]; Hu Q., et al., 2010 [Stem cells (ahead of print)]; Badylak S F et al. 2009 [ActaBiomaterialia, 5: 1-13]; Badylak S F 2004 [Transplant Immunology, 12: 367-377]; Cohen S. et al. [Tissue Eng Part A. 2010 (10): 3119-37]; Shen J. et al. 2010 (Int J Artif Organs, 33: 161-170); Barbero A., et al., Arthritis & Rheumatism, 48: 1315-1325, 2003; Bieback K., et al., Stem Cells 2004, 22:625-634; U.S. Patent Application No. 20100185219 (to Arthur A. Gertzman et al.).

SUMMARY OF THE INVENTION

According to an aspect of some embodiments of the present invention there is provided a method of isolating an extracellular matrix, comprising: (a) culturing mesenchymal progenitor cells under conditions which induce production of extracellular matrix from the mesenchymal progenitor cells, wherein differentiation into an adipogenic lineage of the mesenchymal progenitor cells is reduced by at least 70% as compared to differentiation of mesenchymal stem cells from an adult adipose source under identical assay conditions, and wherein at least 70% of the mesenchymal progenitor cells are CD105+ (CD105 positive), (b) isolating the extracellular matrix produced by the mesenchymal progenitor cells, thereby isolating the extracellular matrix.

According to an aspect of some embodiments of the present invention there is provided a method of generating mesenchymal progenitor cells from embryoid bodies (EBs), comprising: (a) dissociating the EBs into cell aggregates, (b) culturing the cell aggregates in a culture medium so as to expand a population of adherent cells by at least 2 folds, and (c) dissociating the adherent cells to single cells, and (d) culturing the single cells for at least one passage in a culture medium which comprises ascorbic acid but being devoid of dexamethasone, thereby generating the mesenchymal progenitor cells from the embryoid bodies.

According to an aspect of some embodiments of the present invention there is provided an isolated population of cells comprising mesenchymal progenitor cells generated according to the method of some embodiments of the invention.

According to an aspect of some embodiments of the present invention there is provided an isolated population of cells comprising at least 80% mesenchymal progenitor cells, wherein differentiation into an adipogenic lineage of the mesenchymal progenitor cells is reduced by at least 70% as compared to differentiation of mesenchymal stem cells from an adult adipose source under identical assay conditions, and wherein at least 70% of the mesenchymal progenitor cells are CD105+ (CD105 positive).

According to an aspect of some embodiments of the present invention there is provided an isolated extracellular matrix produced according to the method of some embodiments of the invention.

According to an aspect of some embodiments of the present invention there is provided a hybrid device comprising an electrospun element and the isolated extracellular matrix of some embodiments of the invention.

According to an aspect of some embodiments of the present invention there is provided a method of inducing soft tissue regeneration or repair, comprising (a) isolating an extracellular matrix according to the method of some embodiments of the invention, (b) decellularizing the extracellular matrix, and (c) implanting the extracellular matrix resultant of step (b) into a diseased or injured tissue of a subject, thereby inducing the soft tissue regeneration or repair.

According to an aspect of some embodiments of the present invention there is provided a method of inducing soft tissue regeneration or repair, comprising implanting the isolated extracellular matrix of some embodiments of the invention or the hybrid device of some embodiments of the invention into a diseased or injured tissue of a subject, thereby inducing the soft tissue regeneration or repair.

According to an aspect of some embodiments of the present invention there is provided a hydrogel comprising the isolated extracellular matrix of some embodiments of the invention or the hybrid device of some embodiments of the invention.

According to some embodiments of the invention, the mesenchymal progenitor cells are generated from embryoid bodies by a method comprising: (a) dissociating the EBs into cell aggregates, (b) culturing the cell aggregates in a culture medium so as to expand a population of adherent cells by at least 2 folds, and (c) dissociating the adherent cells to single cells, and (d) culturing the single cells for at least one passage in a culture medium which comprises ascorbic acid but being devoid of dexamethasone, so as to generate the mesenchymal progenitor cells from the embryoid bodies.

According to some embodiments of the invention, the culturing is performed on an electrospun element.

According to some embodiments of the invention, the method further comprising decellularizing the extracellular matrix.

According to some embodiments of the invention, the embryoid bodies are generated by differentiation of pluripotent stem cells.

According to some embodiments of the invention, the pluripotent stem cells are induced pluripotent stem cells (iPSCs).

According to some embodiments of the invention, the pluripotent stem cells are embryonic stem cells.

According to some embodiments of the invention, the iPSCs are derived from plucked human hair follicle keratinocytes (iPS-HFKTs).

According to some embodiments of the invention, the EBs are 8-14 day-old human EBs.

According to some embodiments of the invention, each of the aggregates comprises about 10-30 cells.

According to some embodiments of the invention, dissociating the EBs into the aggregates is effected using Collagenase B.

According to some embodiments of the invention, expansion of the adherent cells by at least 2 folds is effected within 2-3 days of culturing in the culture medium.

According to some embodiments of the invention, differentiation into an adipogenic lineage of the mesenchymal progenitor cells is reduced by at least 70% as compared to differentiation of mesenchymal stem cells from an adult adipose source under identical assay conditions.

According to some embodiments of the invention, differentiation into an osteogenic lineage of the mesenchymal progenitor cells is increased by at least 50% as compared to differentiation of mesenchymal stem cells from an adult adipose source under identical assay conditions.

According to some embodiments of the invention, the isolated extracellular matrix of some embodiments of the invention, being decellularized.

According to some embodiments of the invention, the culturing is performed on an electrospun element.

According to some embodiments of the invention, the electrospun element comprises polycaprolactone (PCL).

According to some embodiments of the invention, the electrospun element comprises polycaprolactone (PCL) and poly (lactic-co-glycolic acid) (PLGA).

According to some embodiments of the invention, at least 70% of the mesenchymal progenitor cells are CD90+ (CD90 positive).

According to some embodiments of the invention, at least 70% of the mesenchymal progenitor cells are characterized by a CD105+/CD90+/CD73+/CD44+/CD29+ signature.

According to some embodiments of the invention, at least 70% of the mesenchymal progenitor cells are characterized by a CD45−/CD34− signature.

According to some embodiments of the invention, the mesenchymal progenitor cells maintain the ability to form extracellular matrix for at least 8 passages.

According to some embodiments of the invention, the mesenchymal progenitor cells maintain the ability to form extracellular matrix for about 12-15 passages.

According to some embodiments of the invention, the extracellular matrix comprises collagen, actin, vimentin, fibronectin and laminin.

According to some embodiments of the invention, the hybrid device of some embodiments of the invention further comprising a synthetic mesh.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figures 1A, 1B, 1C, 1D, 1E, 1F, 1G, 1H:
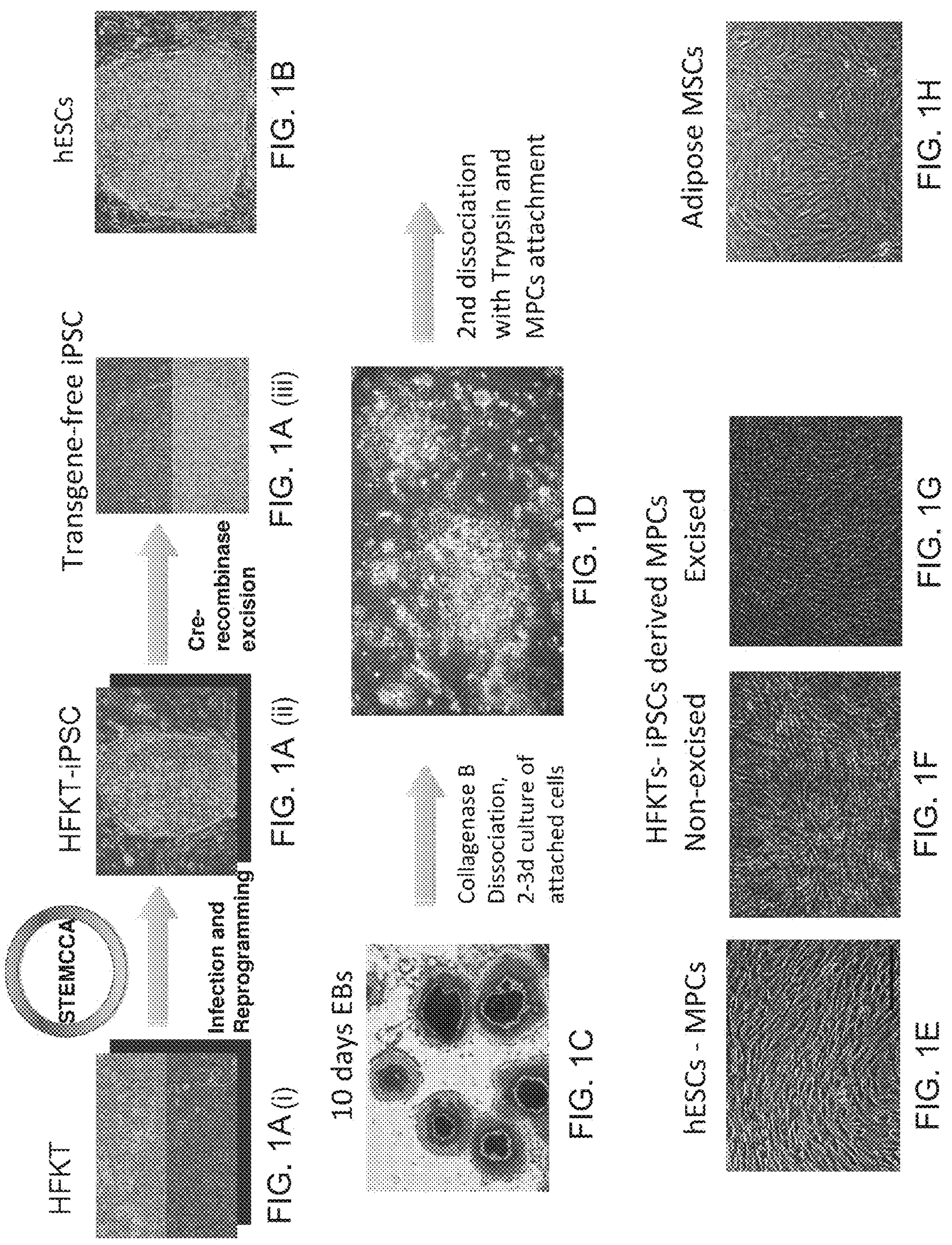

FIGS. 1A-H are images depicting the generation of mesenchymal progenitor cells (MPCs) from pluripotent stem cells according to some embodiments of the invention. FIG. 1A—depicts the steps of generating transgene-free induced pluripotent stem cells from hair follicle keratinocytes (HFKTs) which were further used to generate the MPCs according to some embodiments of the invention. HFKTs (FIG. 1A(i)) were reprogrammed using a single lentiviral STEMCCA vector [Somers, A., et al. 2010. Generation of transgene-free lung disease-specific human iPS cells using a single excisable lentiviral stem cells cassette. Stem Cells, 28(10):1728-40; Sommer, C. A., et al., 2009. Induced pluripotent stem cell generation using a single lentiviral stem cell cassette. Stem Cells 27, 543-549) harboring the reprogramming factors (Oct4, Sox2, Klf4 and c-Myc). FIG. 1A(ii) shows the resulting induced pluripotent stem cell (HFKT-iPSC). Excision of the lentiviral STEMCCA vector (the transgene) with cre-recombinase resulted in a viral-free (transgene-free) iPSC clone (FIG. 1A(iii)). FIG. 1B—is an image of colony of human embryonic stem cells H9.2 cell line which was used for generation of MPCs according the method of some embodiments of the invention. FIG. 1C—embryoid bodies (EBs) were generated by the spontaneous differentiation of iPSCs (HFKT-iPSCs clone KTN7 and transgene-free HFKT-iPSCs clones: Cre-KTN7.3 and Cre-KTR 13.4) or hESCs-H9.2. Shown are 10-days EBs. FIG. 1D—MPCs according to some embodiments of the invention generated from the EBs. The EBs were dissociated by Collagenase B to small cell clusters of about 10-30 cells (e.g., 20 cells), which were cultured for 2-3 days in a BHK medium, which comprises ascorbic acid but is devoid of dexamethasone. Shown are the cell clusters following 2 days of culturing in the BHK medium). FIGS. 1E-G—images of mesenchymal progenitor cells derived from hESCs (FIG. 1E), or from HFKTs-iPSCs which were either non-excised by Cre-recombinase (FIG. 1F) or excised by Cre-recombinase (transgene-free) (FIG. 1G). FIG. 1H—an image of adipose-derived mesenchymal stem cells. Note that the morphology of the mesenchymal progenitor cells generated according to the method of some embodiments of the invention (FIGS. 1E-G) is similar to that of MSCs isolated from adipose tissue (FIG. 1H), which is used as a gold standard for MSCs. Also note that the excised HFKT-iPSCs Cre-KTN7.3 derived MPCs culture (FIG. 1G) is very homogeneous and condense relative to MPCs isolated from hESCs or from the transgene-containing HFKT-iPSCs.

Figures 2A, 2B, 2C, 2D, 2E, 2F, 2G, 2H:
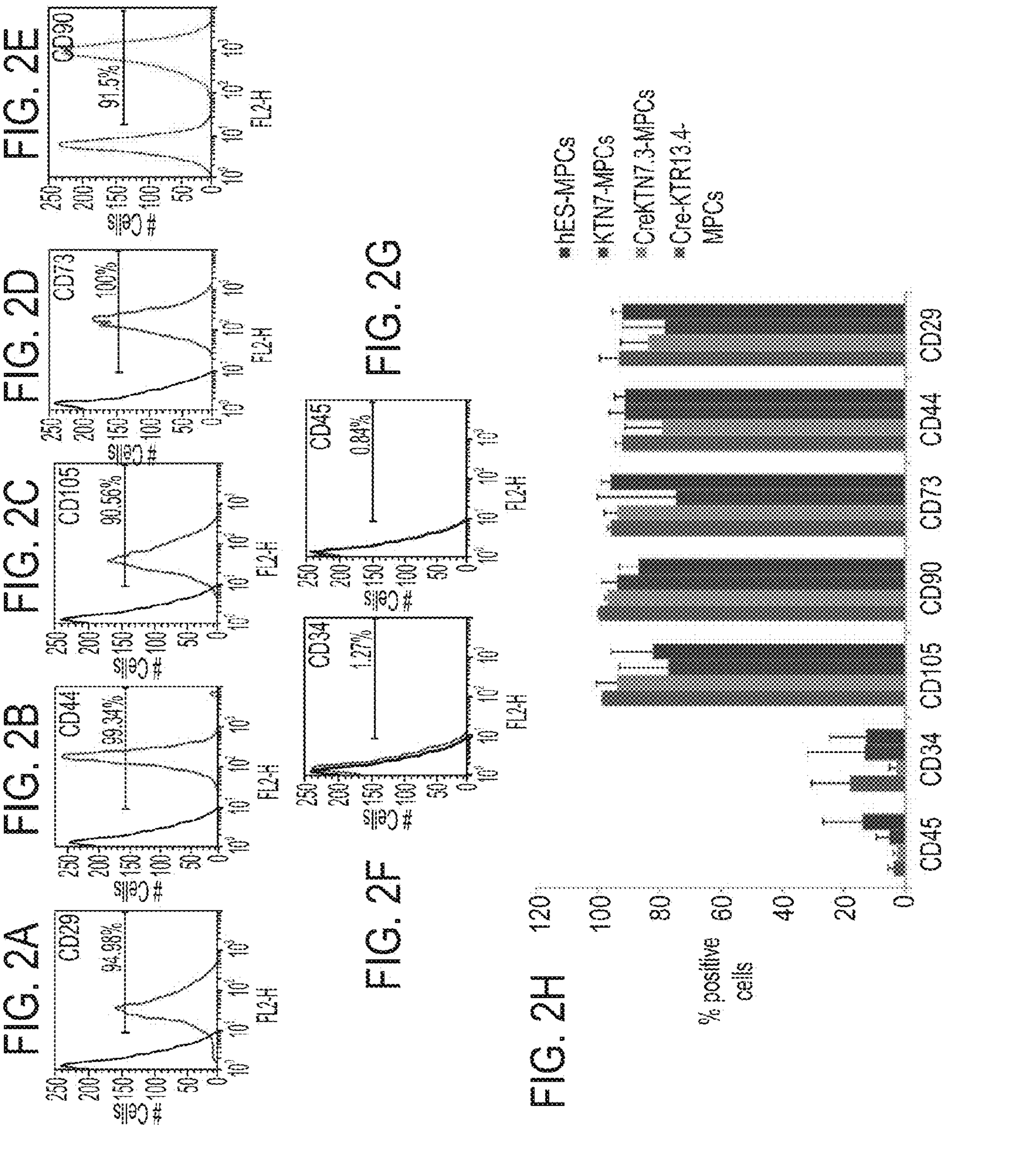

FIGS. 2A-G—Characterization of adipose derived MSCs by FACs analysis of typical MSCs markers. FIG. 2A—CD29; FIG. 2B—CD44; FIG. 2C—CD105; FIG. 2D—CD73; FIG. 2E—CD90; FIG. 2F—CD34; FIG. 2G—CD45. Results show that the adipose derived MSCs can be used as gold standard since they express high levels of known mesenchymal markers as: CD29 (94.98%), CD44 (99.84%), CD105 (98.56%), CD73 (100%), CD90 (91.5%) and are negative to the hematopoietic markers CD34 (1.27%) and CD45 (0.84%).

FIG. 2H—A histogram depicting MPCs characterization using FACS analysis of typical mesenchymal markers. Shown are the percentages of positive cells for each of the mesenchymal and hematopoietic markers. The MPCs were derived from the following sources: hESCs (blue bars), HFKT-iPSCs-Clone KTN7 (red bars) and the excised HFKT-iPSCs-Clones Cre-KTN7.3 (green bars) and Cre-KTR13.4 (purple bars). Results show that MPCs derived from the excised HFKT-iPSC clones express higher levels of mesenchymal markers (CD105, CD90, CD73, CD44 and CD29) relative to MPCs derived from non-excised KTN7 or from hESCs. Data were obtained relative to the negative control cells stained with only a secondary antibody.

Figures 3A, 3B, 3C, 3D, 3E, 3F, 3G, 3H, 3I, 3J, 3K, 3L:
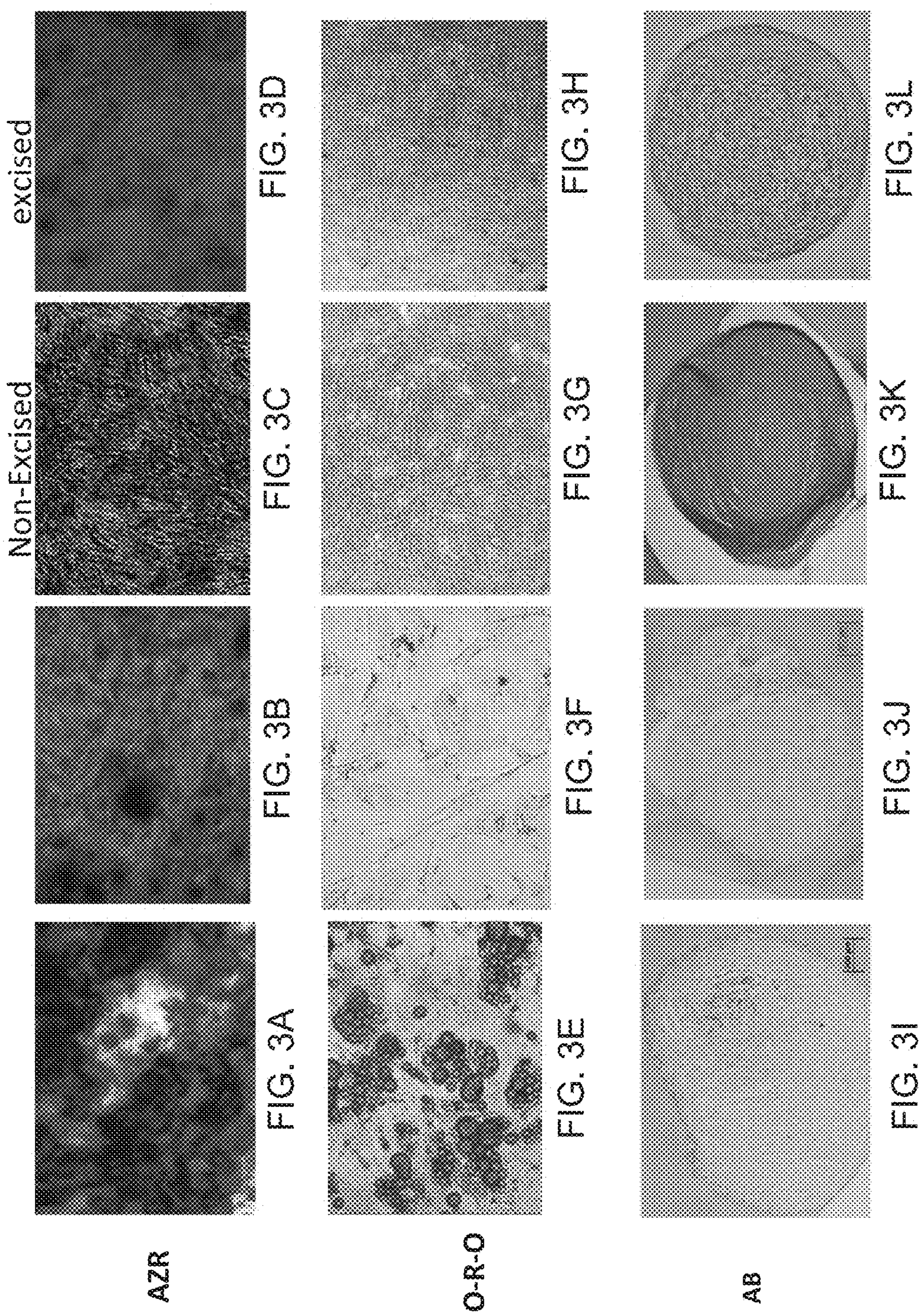

FIGS. 3A-L are images depicting the results of in vitro differentiation assays of MSCs which were derived from adipose tissue (FIGS. 3A, 3E, 3I), hESCs-derived MPCs (FIGS. 3B, 3F, 3J), human HFKT-non-excised-iPSCs derived MPCs (FIGS. 3C, 3G, 3K), and human HFKT-excised-iPSCs derived MPCs (FIGS. 3D, 3H, 3L). Bone differentiation was analyzed using Alizarin-red staining following 30 days in an osteogenic medium (FIGS. 3A-D); Fat Differentiation was analyzed using Oil-Red O staining following 30 days in an adipogenic medium (FIGS. 3E-H); Cartilage differentiation was analyzed by Alcian-Blue staining following 30 days in a chondrogenic medium (FIGS. 3I-L). Results show that all cell lines are positive for Alizarin-red staining, indicating calcium deposition by cells of an osteogenic lineage. In addition, while cartilage differentiation was most efficient with the excised HFKT-iPSCs derived MPCs (FIG. 3L) and the non-excised HFKT-iPSCs derived MPCs (FIG. 3K), adipogenic differentiation was pronounced in adipose-derived MSCs (FIG. 3E), but was hardly evident in hESC-derived MPCs (FIG. 3F) and completely absent in HFKT-iPSCs-derived MPCs (FIGS. 3G and H). Results represent exemplary data of three independent repeated experiments.

Figures 4A, 4B, 4C, 4D, 4E, 4F, 4G, 4H, 4I, 4J:
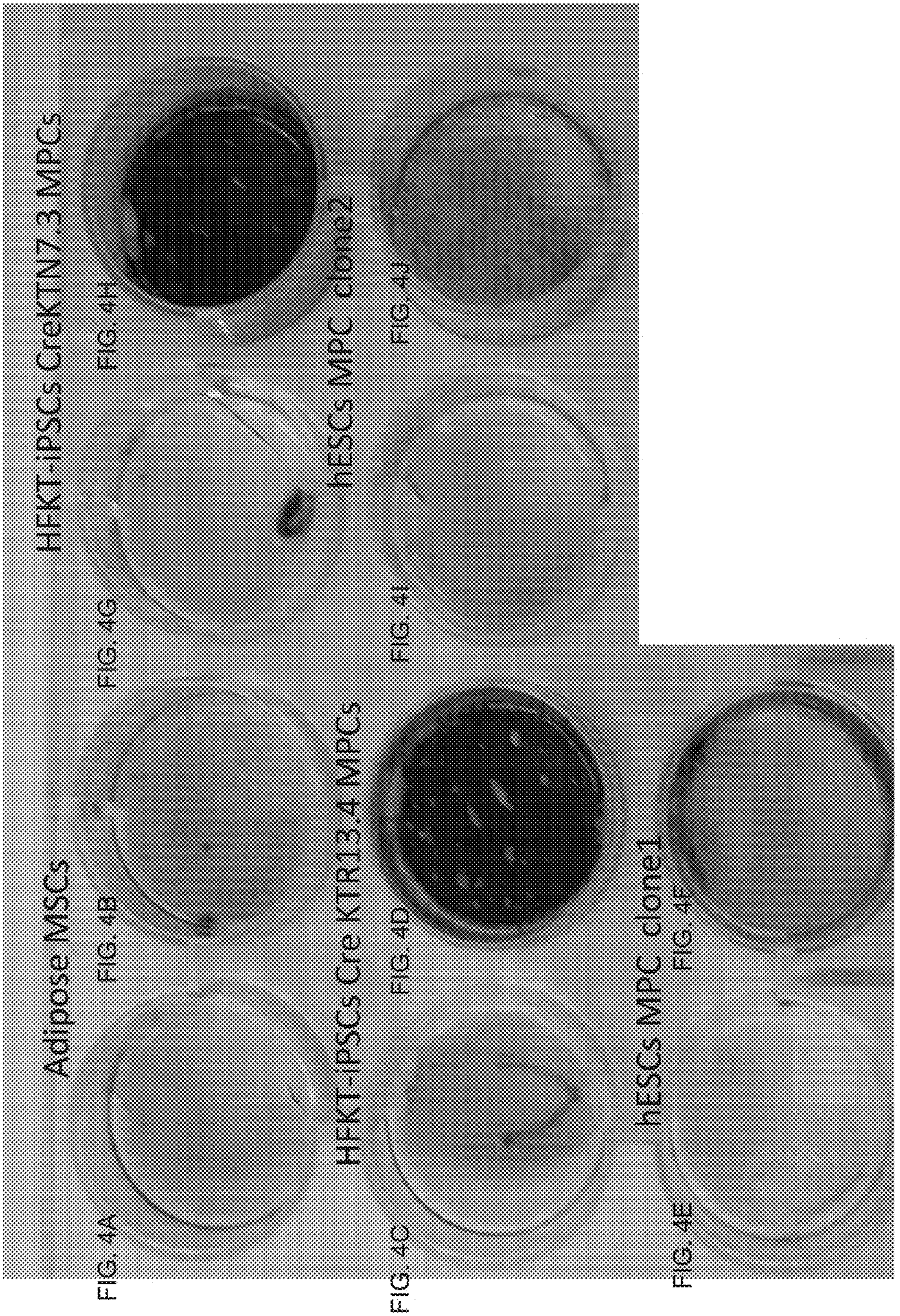

FIGS. 4A-J are images of tissue culture plates depicting in vitro differentiation of adipose-derived MSCs and pluripotent stem cells-derived MPCs into the osteogenic lineage. Adipose MSCs (FIGS. 4A-B), HFKT-iPSCs Cre KTR13.4 (FIGS. 4C-D), hESCs MPCs clone 1 (FIGS. 4E-F), HFKT-iPSCs CreKTN7.3 MPCs (FIGS. 4G-H) and hESCs MPCs clone 2 (FIGS. 4I-J) were cultured for 4 weeks in either a non-inducing medium (BHK medium; FIGS. 4A, C, E, G, and I) or an osteogenic inducing medium (osteogenic medium; FIGS. 4B, D, F, H and J) and the cells were then stained with Alizarin-red. Note that bone differentiation is highly elevated in MPCs derived from the excised HFKT-iPSCs clones relative to MPCs derived from hESCs clones or from adipose MSCs.

Figures 5A, 5B, 5C, 5D, 5E, 5F, 5G, 5H, 5I, 5J, 5K, 5L:
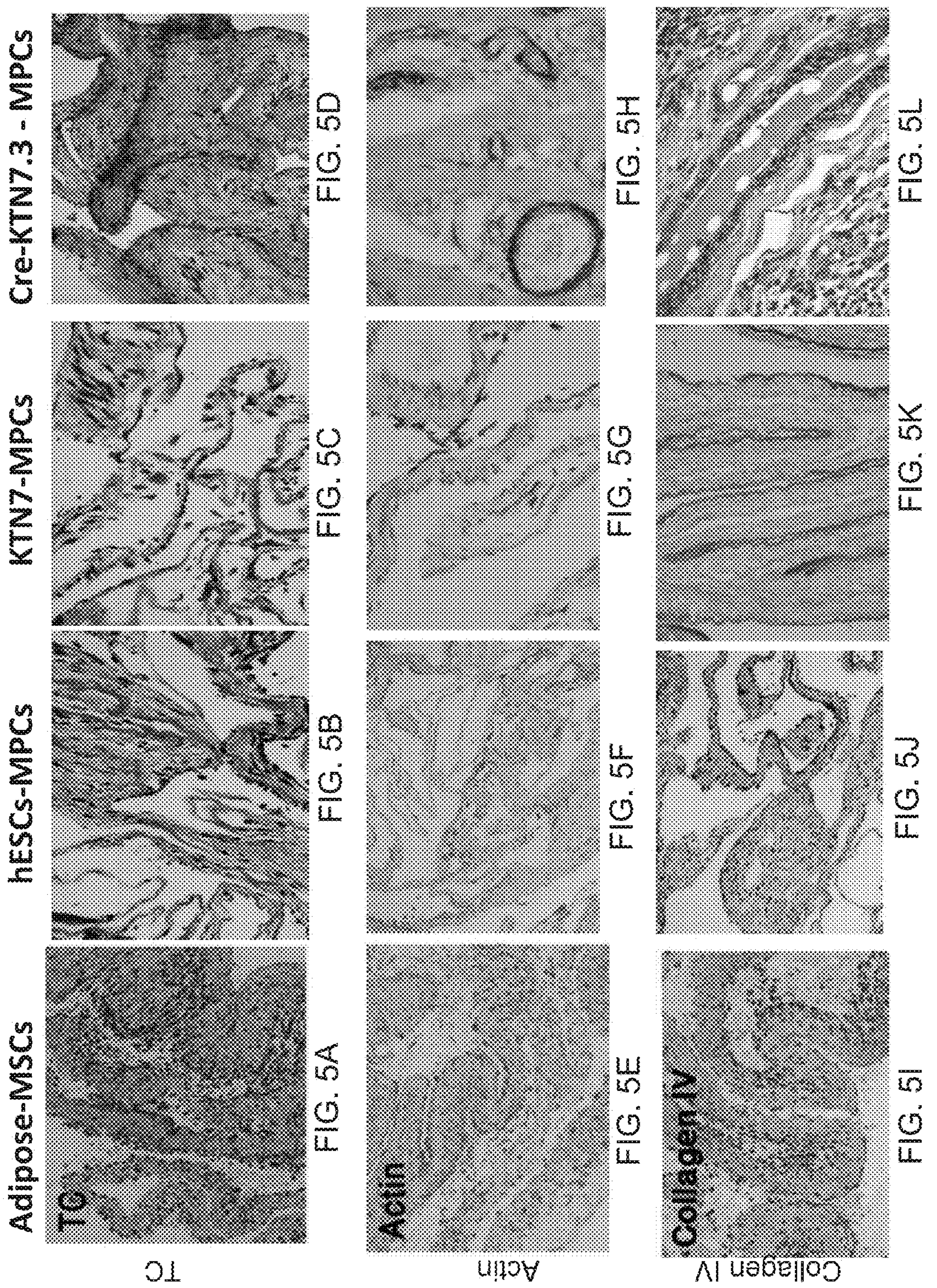
Figures 5M, 5N, 5O, 5P, 5Q, 5R, 5S, 5T, 5U, 5V, 5W, 5X:
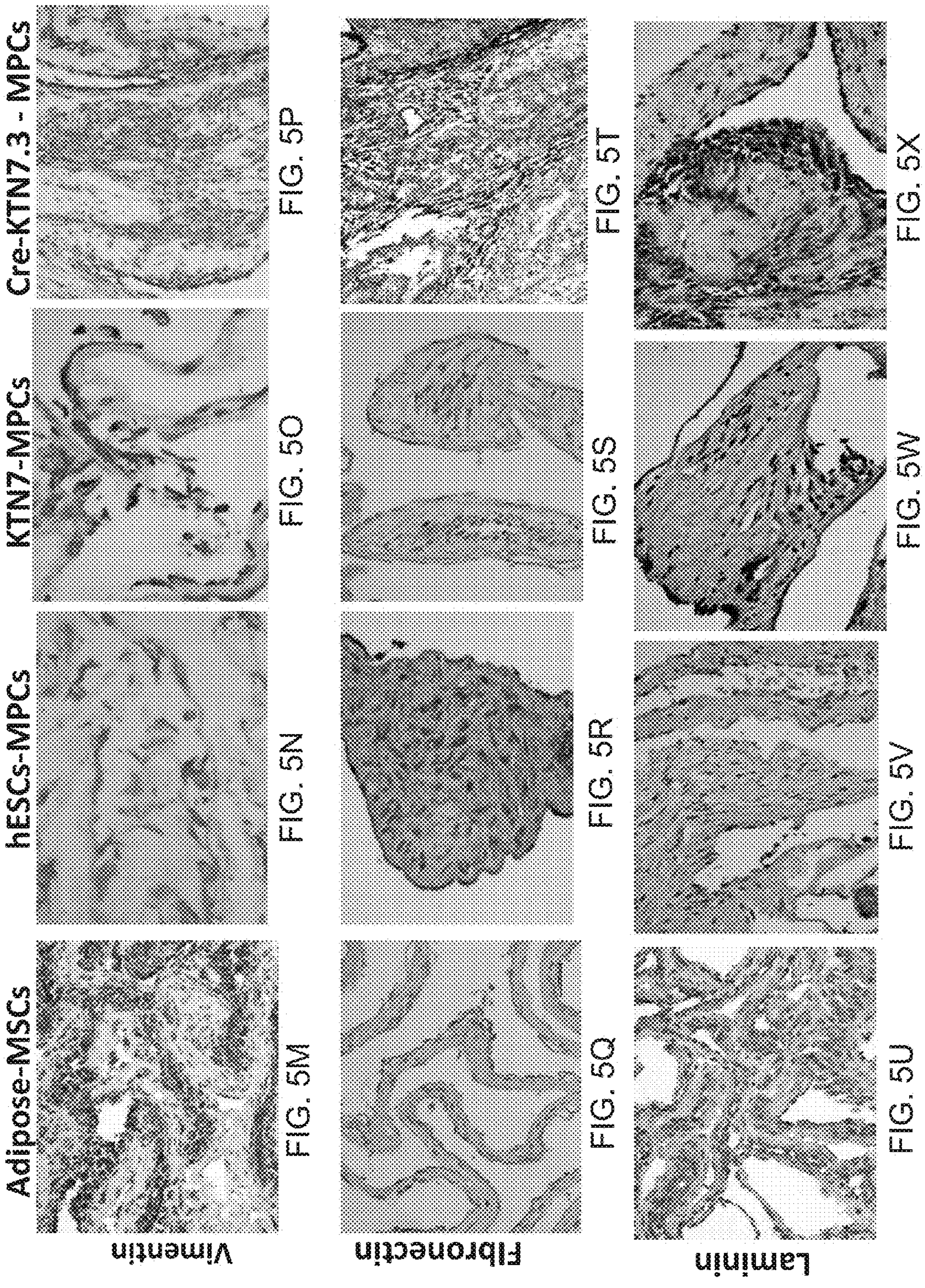

FIGS. 5A-X—Histology analyses of extracellular matrix (ECM) generated from adult human adipose MSCs (FIGS. 5A, 5E, 5I, 5M, 5Q, 5U) as well as from MPCs generated from the pluripotent sources: hESCs (FIGS. 5B, 5F, 5J, 5N, 5R, 5V), and HFKT-iPSCs clone KTN7 (FIGS. 5C, 5G, 5K, 5O, 5S, 5W) and the excised clone Cre-KTN7.3 (FIGS. 5D, 5H, 5L, 5P, 5T, 5X). Trichrome (TC) staining stained all collagens by a strong blue dye (FIGS. 5A-5D). Immunostainings were done with antibodies against actin (FIGS. 5E-H), Collagen IV (FIGS. 5I-5L), Vimentin (FIGS. 5M-P), fibronectin (FIGS. 5Q-T) and laminin (FIGS. 5U-X). Results show that all MPCs tested produce high quantities of ECM collagens (FIGS. 5B-D) as compared to the ECM quantities produced by adipose-derived MSCs (FIG. 5A), with most significant ECM components could be detected at ECM generated by the excised HFKT-iPSCs clones (results show here for Cre-KTN7.3 clone, similar data were found for the other excised clone Cre-KTR13.4 (Data not shown). Immunostaining of ECM generated from all stem cells sources revealed positive expression of specific ECM proteins including actin, collagen IV, fibronection, laminin and vimentin. However, round structures of actin protein were found only within ECM derived MPCs originated from transgene-free HFKT-iPSCs. This ECM source also exhibits higher and specific expression of collagen IV, fibronectin and Laminin relative to other pluripotent sources that were tested.

Figures 6A, 6B, 6C, 6D, 6E, 6F, 6G, 6H:
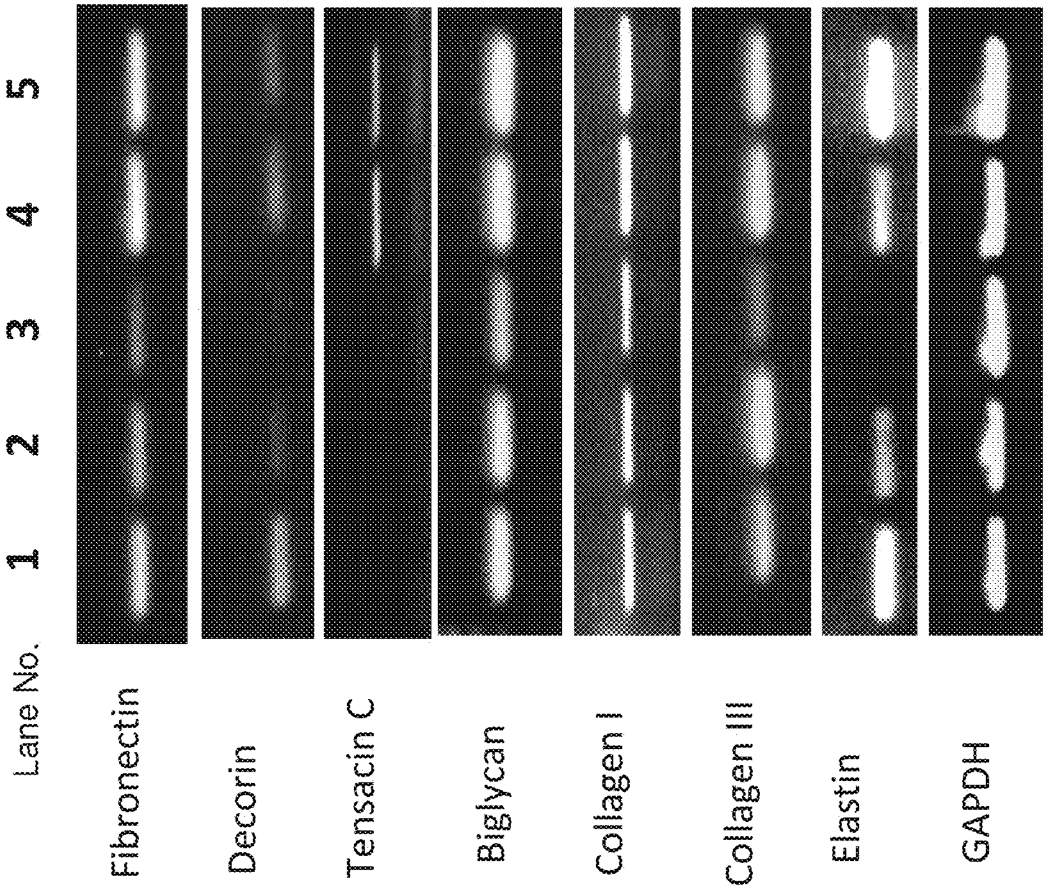

FIGS. 6A-H—are RT-PCR analyses depicting gene expression of ECM markers. RT-PCR was done for ECM samples generated by the following cell sources: Adipose derived MSCs (lane 1), hESCs derived MPCs (lane 2), KTN7 derived MPCs (lane 3), Cre-KTN7.3 derived MPCs (lane 4), Cre-KTR13.4 derived MPCs (lane 5). FIG. 6A—Fibronectin; FIG. 6B—Decorin; FIG. 6C—Tensacin C; FIG. 6D—Biglycan; FIG. 6E—Collagen I; FIG. 6F—Collagen III; FIG. 6G—Elastin; FIG. 6H—GAPDH. Results show that most markers were highly expressed in the ECM samples obtained from the excised HFKT-iPSCs clones Cre-KTN7.3 and Cre-KTR13.4.

Figures 7A, 7B, 7C, 7D, 7E, 7F, 7G, 7H:
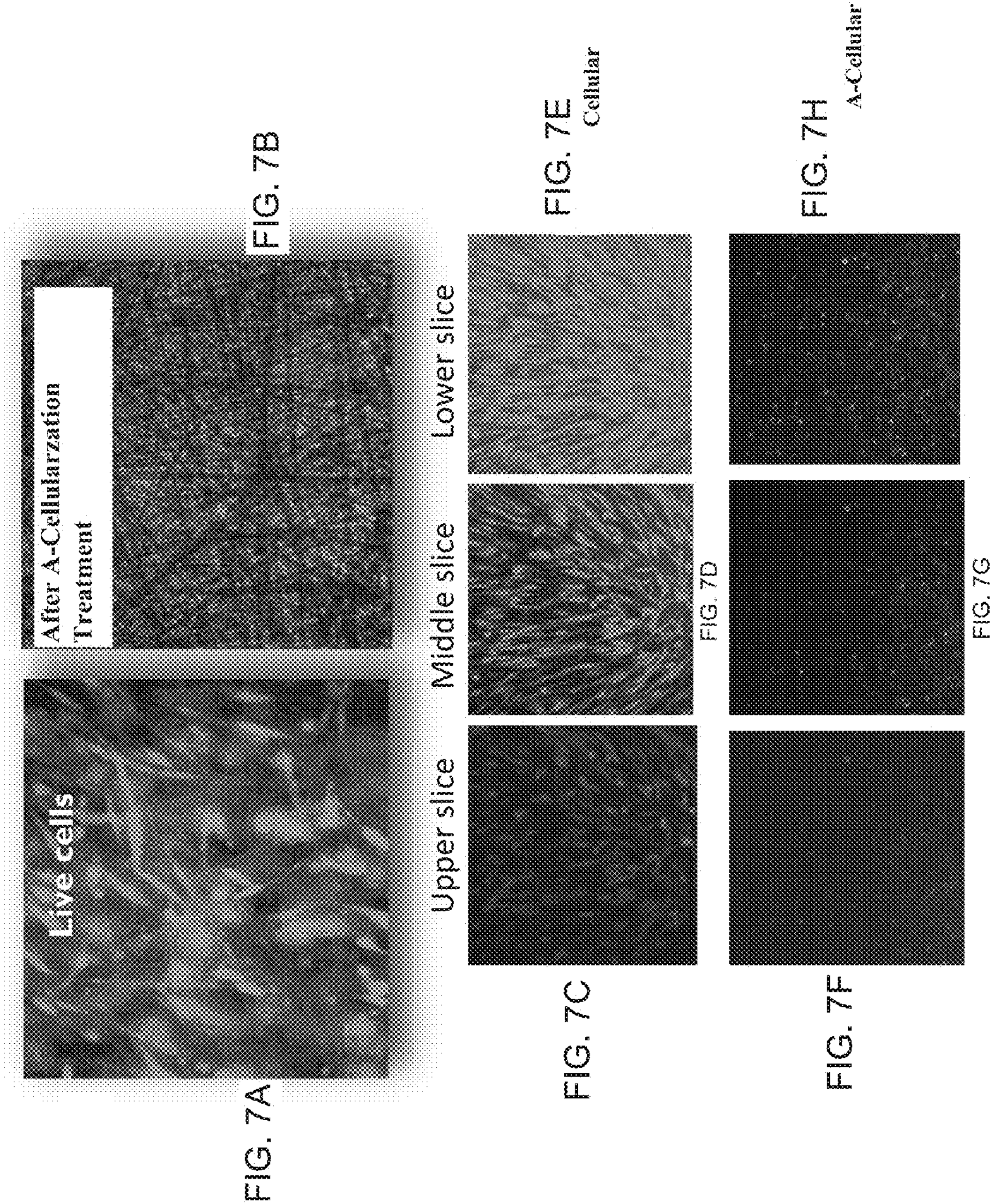

FIGS. 7A-H are images of seeded nanofibers layer (NFL) with live cells or acellularized NFL. MPCs derived from the excised HFKT-iPSCs clone KTN7.3 were seeded on the NFL and cultured for 3-4 weeks in the BHK medium which enables ECM generation. Live cells staining was done using Vybrabt© CFDA SE cell tracker kit (Invitrogen). Acellularization treatment on NFL-ECM includes incubation in hypertonic solution and then tritonX100 and DNAse treatment. FIG. 7A—image of fluorescent microscopy of NFL with live cells; FIG. 7B—image of fluorescent microscopy of acellularized NFL. The live cells staining show the efficiency of MPCs propagation within the NFL. Following acellularization treatment cells could be eliminated from the NFL. FIGS. 7C-7H—images obtained by confocal microscopy analysis of nanofibers with live cells (FIGS. 7C-E) and acellularized nanofibers (FIGS. 7F-H). Shown are representative images of the upper slices (FIGS. 7C, 7F), middle slices (FIGS. 7D, 7G) and lower slices (FIGS. 7E, 7H). Note that the cells efficiently penetrate to internal layers of the scaffold, shown by the various slices. This analysis indicates that cells proliferated within the NFL, and not only on the NFL surface.

Figure 8A:
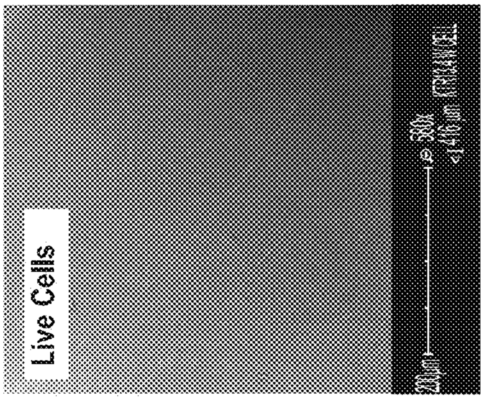
Figure 8B:
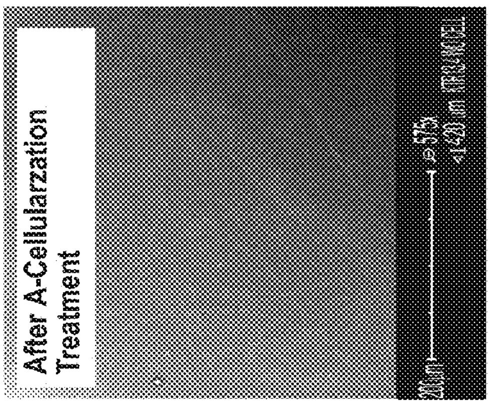
Figure 8C:
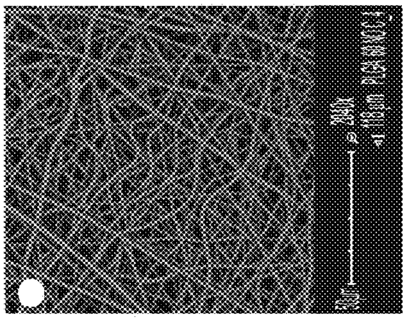
Figure 8D:
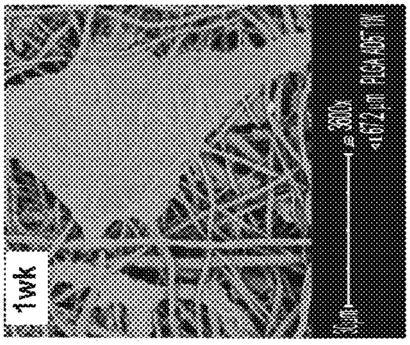
Figure 8E:
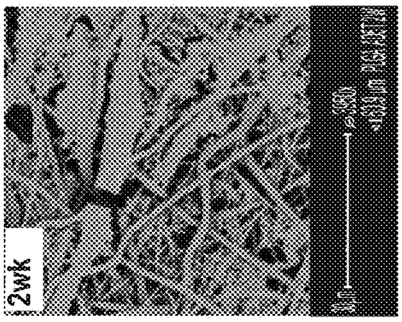

FIGS. 8A-B are scanning electron microscopy (SEM) images depicting live cells (KTR13.4 MPCs) on PLGA-NFL (FIG. 6A) and PLGA-NFL following acellularization (FIG. 6B). Size bar=200 μm.

FIGS. 8C-F are images of high magnification scanning electron microscopy (SEM) depicting generation of ECM on PLGA-NFL scaffolds. PLGA-NFLs were seeded with Cre-KTR13.4 MPCs and cultured for several weeks in the presence of the BHK medium. At predetermined time points, 0 (no cells were seeded) (FIG. 8C), one week (FIG. 8D), two weeks (FIG. 8E) and three weeks (FIG. 8F) in culture. The scaffolds were subject to an acellularization process and photographed using SEM. Note the structure of the PLGA nanofibers in the absence of cells in FIG. 8C. Following 1 and 2 weeks of culturing the MPCs on the NFL ECM proteins, manifested as collagen fibers, are shown within the NFL, while following 3 weeks MPCs derived ECM has completely covered the NFL surface.

Figure 9A:
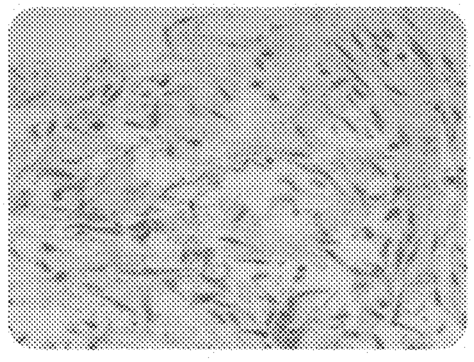
Figure 9B:
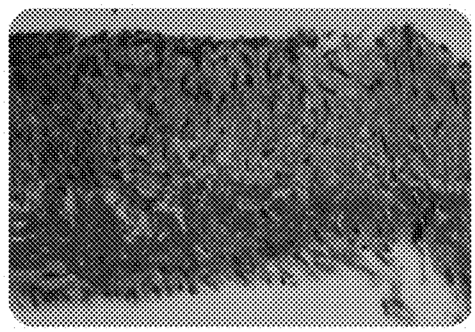
Figure 9C:
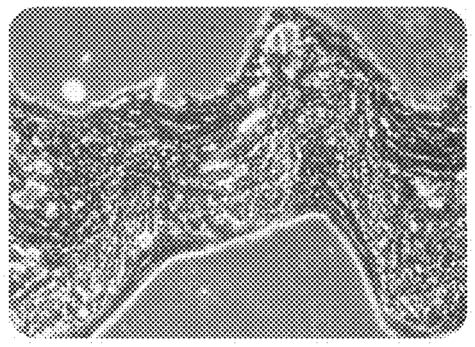
Figure 9D:
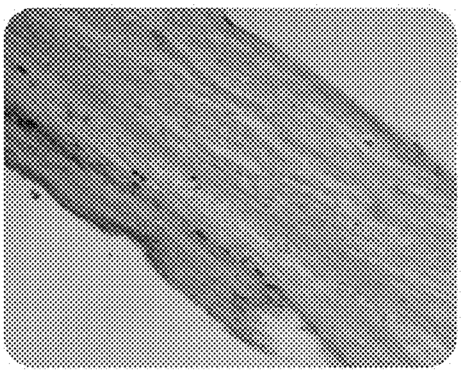
Figure 9E:
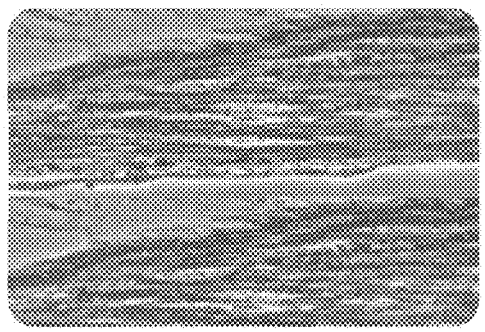
Figure 9F:
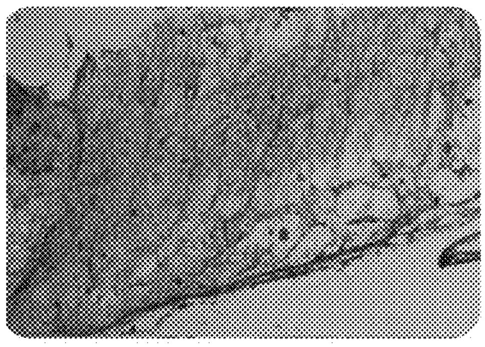

FIGS. 9A-F are images depicting histology characterization of ECM generated within the NFL before (FIGS. 9A-C) and following (FIGS. 9-F) the acellularization process. ECM was generated from MPCs derived from HFKT-iPSCs Cre-KTR13.4 clone cultured within PLGA-NFL for 3 weeks. FIGS. 9A and D—Hematoxylline and eosine (H&E) staining; FIGS. 9B and E—trichrom (TC) staining; FIGS. 9C and F—fibronectin immunostaining. Acellular ECM-NFL was characterized by H&E staining indicating the elimination of viable cells (FIG. 9D) as compared to cellular ECM-NFL (FIG. 9A). Trichrom (TC) staining and fibronectin immunostaining indicate that ECM proteins were generated within the NFL and remain intact following acellularization treatment.

Figure 10A:
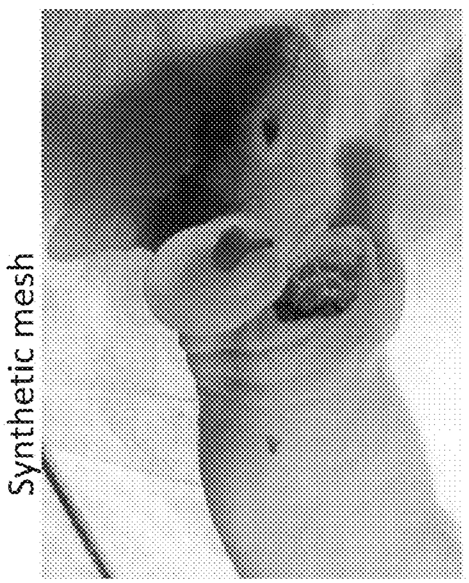
Figure 10B:
Figure 10C:
Figure 10D:
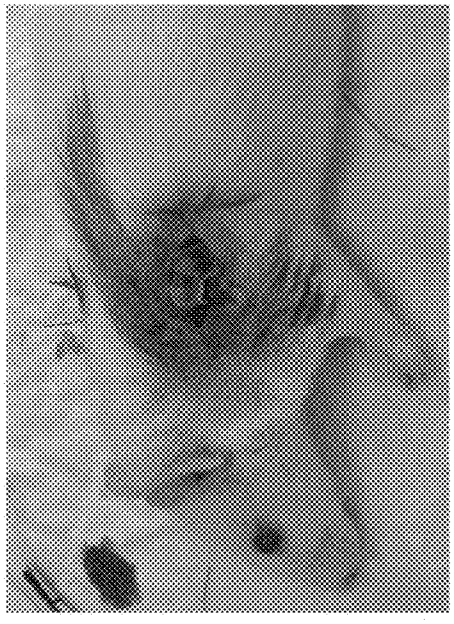
Figure 10E:
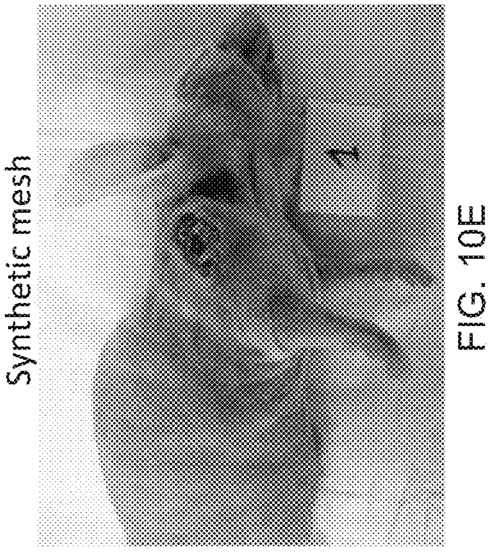
Figure 10F:
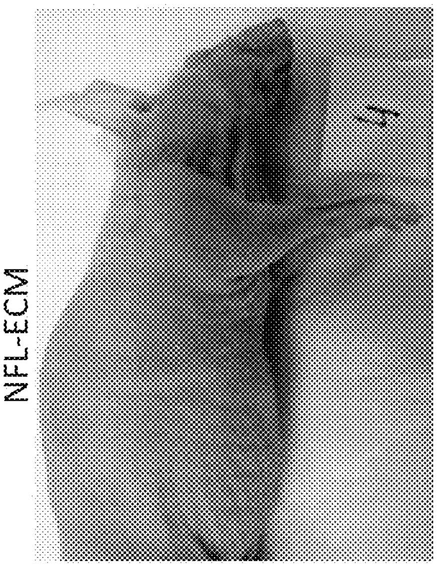
Figure 10G:
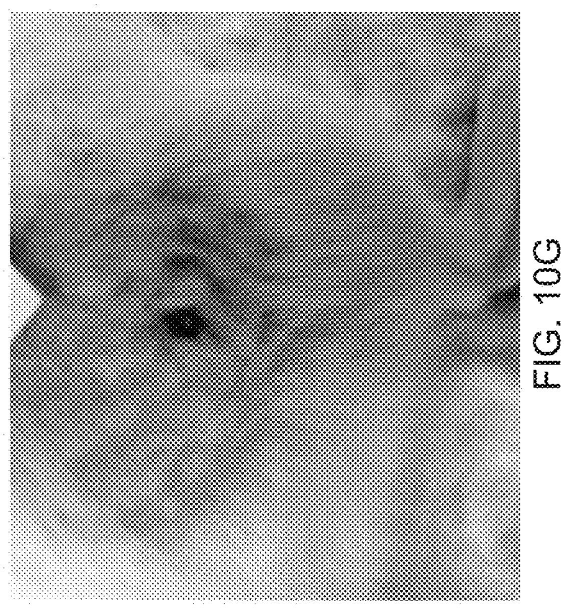
Figure 10H:
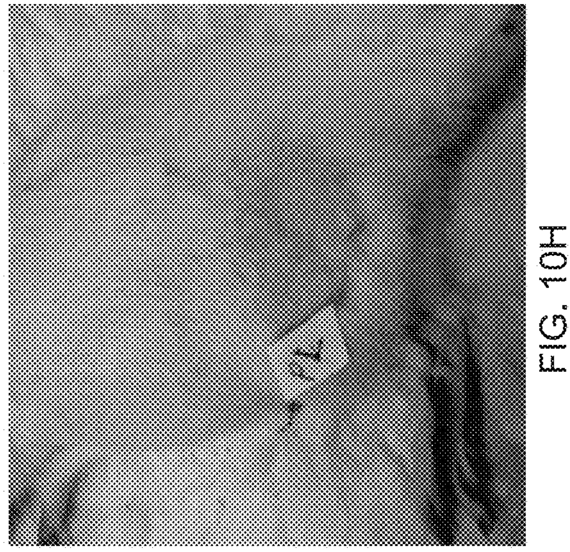

FIGS. 10A-H are photographs of mice demonstrating subcutaneous transplantation of synthetic mesh (Prolift®, Ethicon) (FIGS. 10A, 10C, 10E and 10G), and NFL-ECM construct (FIGS. 10B, 10D, 10F and 10H) in SCID beige mice (FIGS. 10A-B; FIGS. 10E-F) and Sprague-Dawley Rats (FIGS. 10C-D and FIGS. 10G-H). The implants were originally sutured and well covered by the animal skin. Two identical implants were transplanted in both neck sides of SCID Beige mice, and within two thighs of the rat (FIGS. 10A-D). Eight weeks post transplantation (FIGS. 10E-H) the animals were sacrificed and analyzed and implants were subjected to histology analysis. Note that 8 weeks post transplantation in both transplanted SCID mice and rats 75% of synthetic meshes implants were completely discharged and could be clearly observed externally of the animal skin (FIGS. 10E and 10G). Moreover, the SCID mice transplanted with the synthetic mesh exhibit a sick and slim appearance as compared with the mice transplanted by NFL-ECM (e.g., compare the mouse in FIG. 10E to the mouse in FIG. 10F). In addition, note that the NFL-ECM implants were not rejected from the animal's body and the transplanted SCID mice were big and healthy. Also note that rats transplanted with the NFL-ECM were healthy with complete healing of the wound (FIG. 10H) as compared to the rat sutured with the synthetic mesh (FIG. 10G).

Figures 11A, 11B, 11C, 11D:
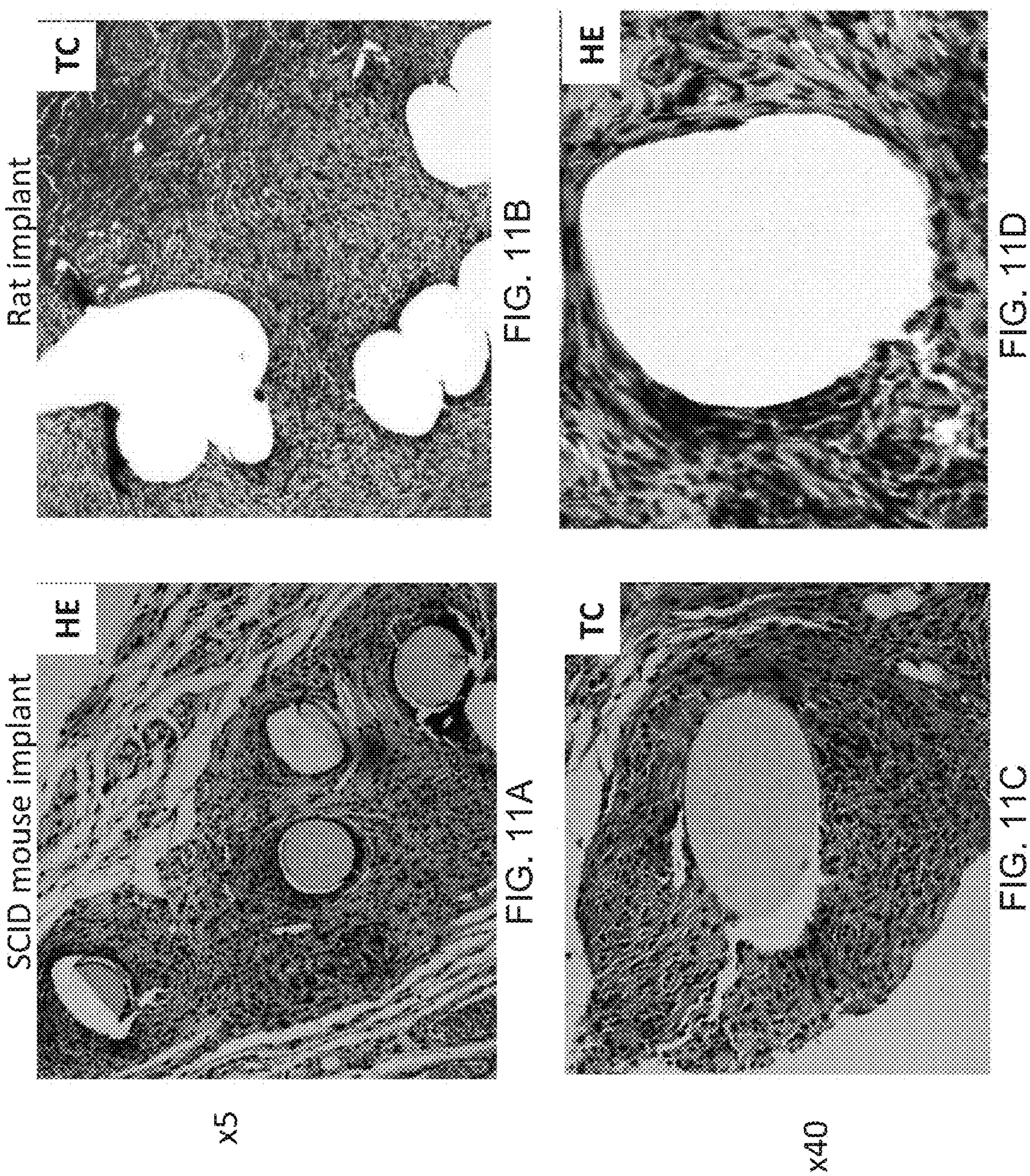

FIGS. 11A-D are images of histological sections of synthetic mesh implants sections in SCID mice (FIGS. 11A and 11C) and rats (FIGS. 11B and 11D). Histology was done for paraffin sections using hematoxilin & Eosin (HE) (FIGS. 11A and 11D) and trichrome (TC) staining (FIGS. 11B and 11C). Data revealed rigorous granuloma containing lymphocytes and neutrophils surrounding the synthetic fibers, observed as blue and white ellipsoids which are not stained by the histochemistry reagents. Magnification: ×5 in FIGS. 11A and 11B; ×40 in FIGS. 11C and 11D.

Figure 12A:
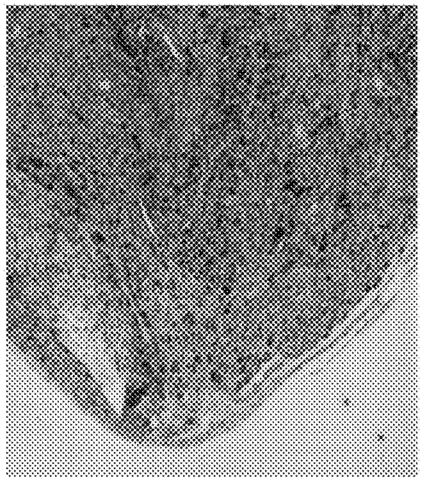
Figure 12B:
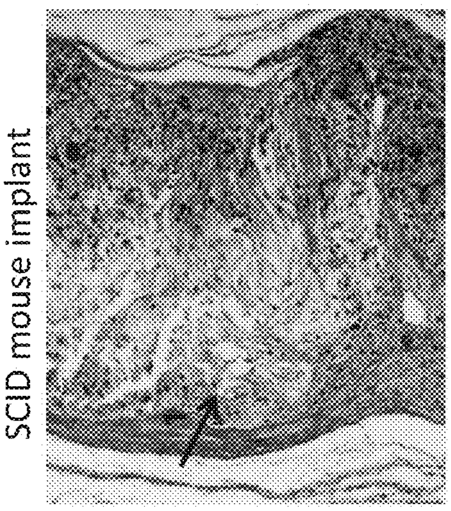
Figure 12C:
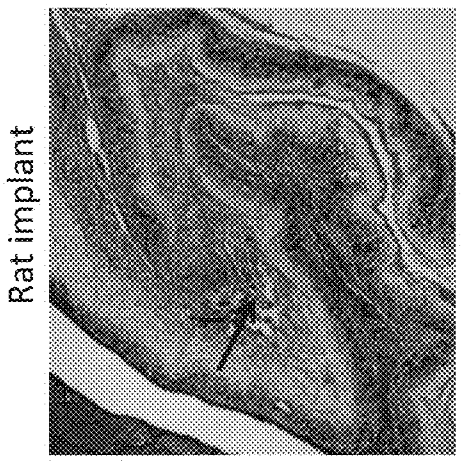
Figure 12D:
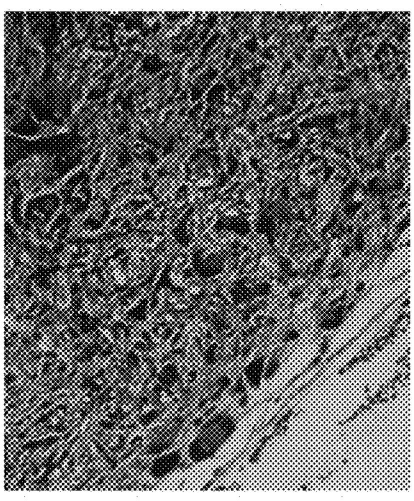
Figure 12E:
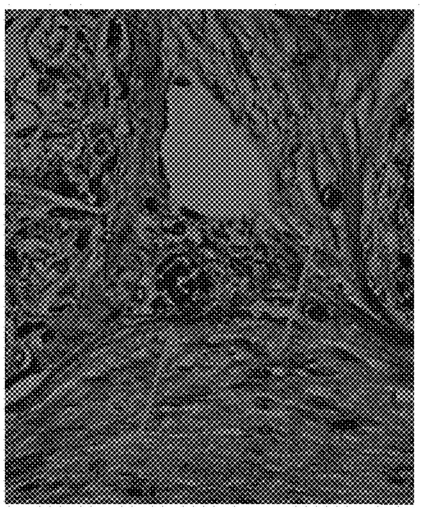

FIGS. 12A-F are images of histological sections of NFL-ECM implants sections in SCID mice (FIGS. 12B and 12E) and rats (FIGS. 12C and 12F) and in mice which were transplanted with NFL implant (FIGS. 12A and 12D). Results show that implants from NFL, made of electrospun PCL polymer (with no ECM), significantly induced the animal immune response (FIGS. 12A and 12D). Granulomas, particularly containing macrophages, are observed within the NFL region, surrounding by the PCL nanofibers which were not completely degraded following 8 weeks in vivo (FIGS. 12A and 12D). In contrast, the immune response against the hybrid NFL-ECM implant is reduced in both SCID mice and rats (FIGS. 12B, 12C, 12E and 12F). Although granuloma regions could be observed within the hybrid, better integration with the host tissue was visible, strong collagen structures were generated around and within the hybrid device (arrow 1) and new blood vessels were emerged (arrow 2). Magnification: ×5 in FIGS. 12A-C; ×20 in FIGS. 12D-F.

Figures 13A, 13B, 13C, 13D, 13E, 13F:
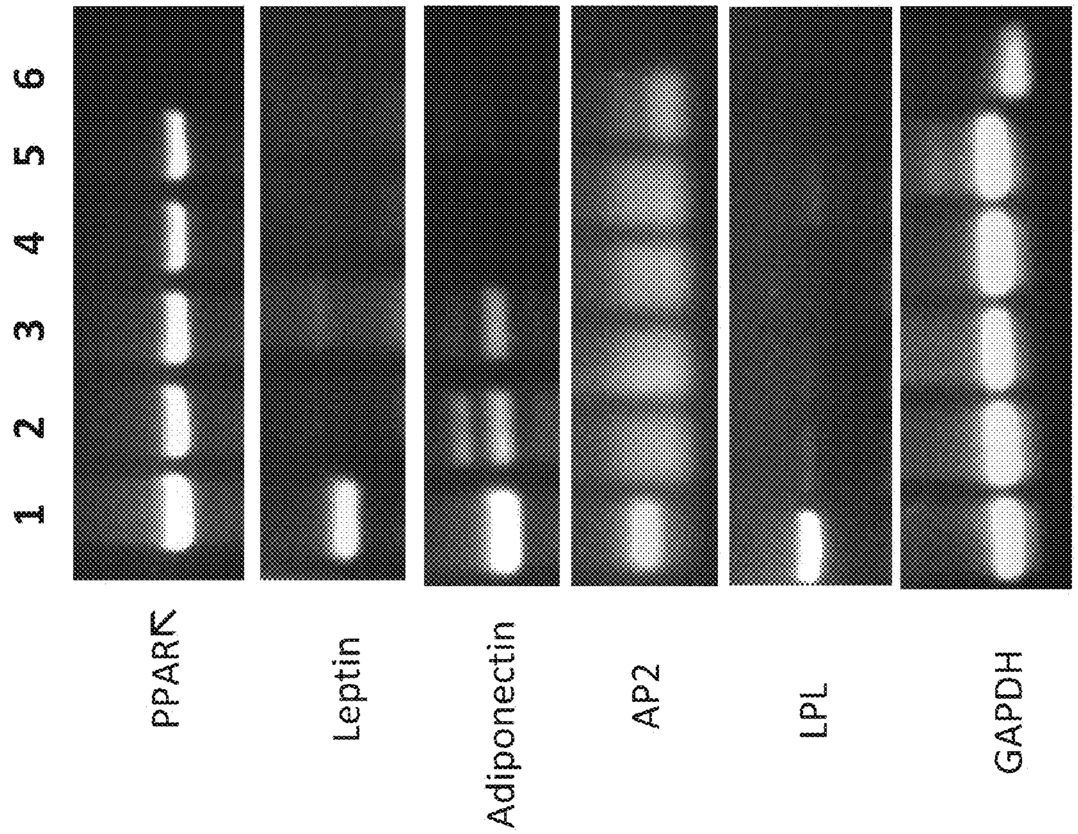

FIGS. 13A-F are images depicting RT-PCR analysis of adipogenic markers in adipose-derived MSCs and pluripotent stem cells-derived MPCs following their differentiation into adipogenic lineages. Total RNA was extracted from cells after 4 weeks of culturing in adipogenic medium and RT-PCR was performed with primer specific to the following mRNA: peroxisome proliferator-activated receptors gamma (PPARγ) (FIG. 13A); leptin (FIG. 13B); adiponectin (FIG. 13C); Adipocyte protein 2 (AP2) (FIG. 13D); Lipoprotein lipase (LPL) (FIG. 13E); and GAPDH (FIG. 13F). Results are shown for the following clones: Lane 1—Adipose MSCs—AD5T; lane 2—HFKT-iPSCs Cre-KTR13.4 MPCs; lane 3—HFKT-iPSCs Cre-KTN7.3 MPCs; lane 4—hESCs (H9.2) derived MPCs (clone 1); lane 5—hESCs (H9.2) derived MPCs (clone 2); lane 6—No DNA (negative control).

Figure 14A:
Figure 14D:
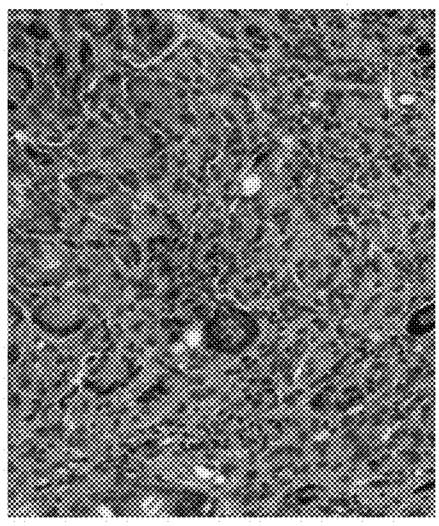
Figure 14B:
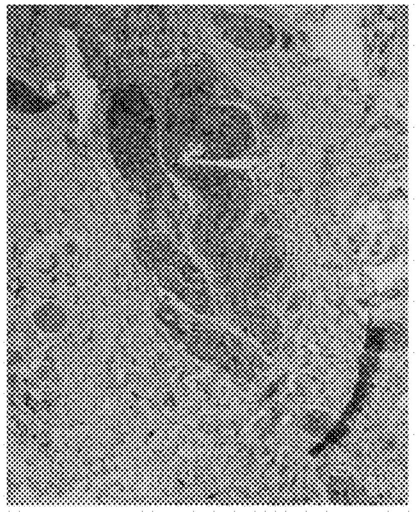
Figure 14E:
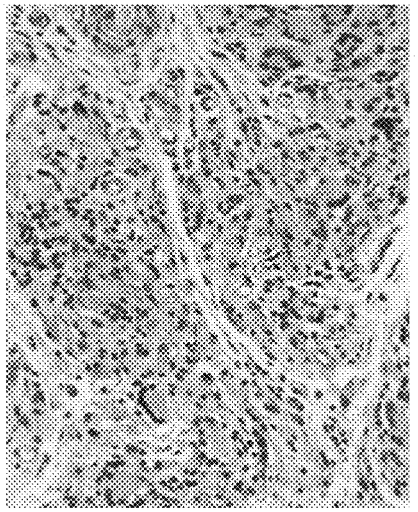
Figure 14C:
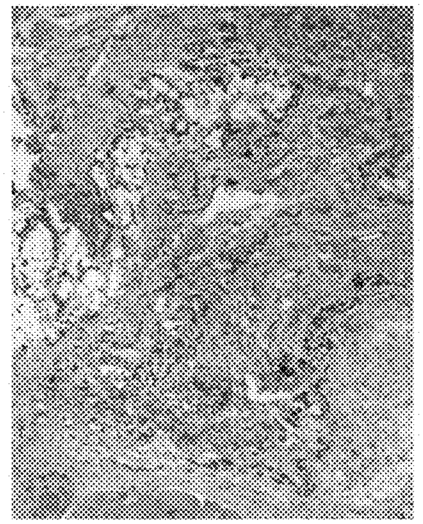
Figure 14F:
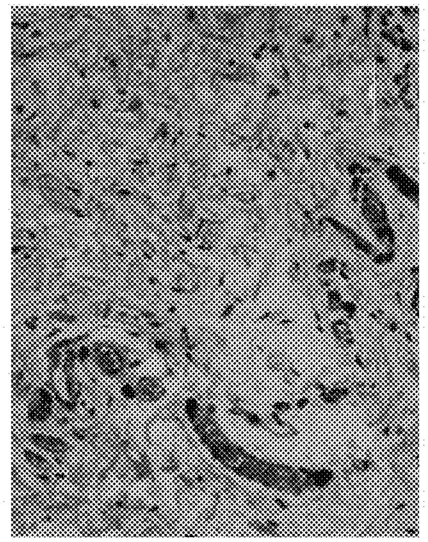
Figure 14G:
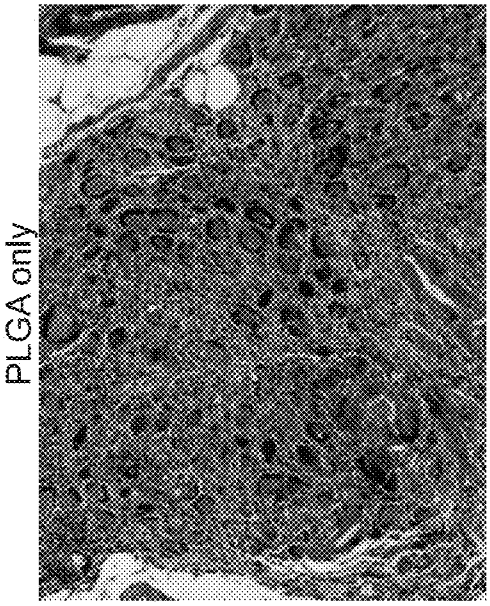
Figure 14H:
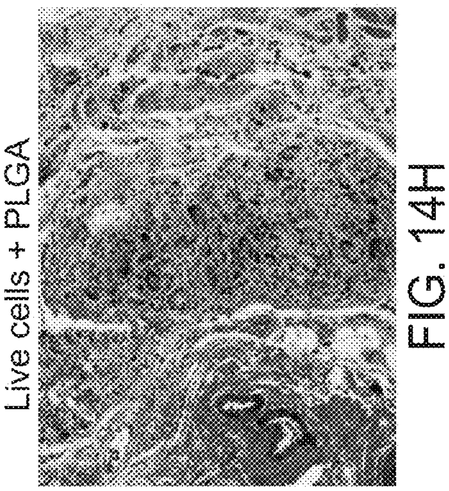
Figure 14I:
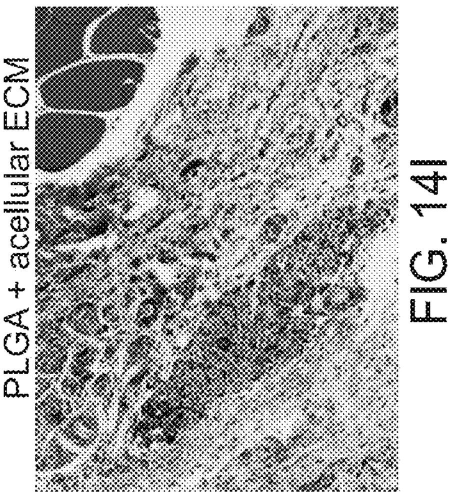

FIGS. 14A-I are microscopic images depicting hematoxylin and Eosin (H&E) (FIGS. 14A-F) and trichrome (TC) (FIGS. 14G-I) of subcutaneously transplanted rats with PLGA scaffolds. Nanofiber layer (NFL) composed of PLGA alone (FIGS. 14A, D and G), or of PLGA with live HFKT-iPSCs Cre KTN7.3 MPCs (before acellularization, FIGS. 14B, E and H) or of PLGA-ECM (made of HFKT-iPSCs Cre KTN7.3 MPCs cells after acellularization; FIGS. 14C, F and I) were used for transplantation in Sprague-Dawley Rats. The scaffolds were originally sutured and well covered by the animal skin. Two identical implants were transplanted within the rat's two thighs. Eight weeks post transplantation the animals were sacrificed and implants were subjected to histology analysis of paraffin sections. FIG. 14A—PLGA alone, H&E ×4 magnification; FIG. 14B—Live cells+PLGA, H&E ×4 magnification; FIG. 14C—Acellular PLGA-ECM, H&E ×4 magnification; FIG. 14D—PLGA alone, H&E ×20 magnification; FIG. 14E—Live cells+PLGA, H&E ×20 magnification; FIG. 14F—Acellular PLGA-ECM, H&E ×20 magnification; FIG. 14G—PLGA alone, TC staining, ×10 magnification; FIG. 14H—Live MPCs (Cre-KTN7.3)+PLGA, TC staining, ×10 magnification; FIG. 14I—Acellular PLGA-ECM, TC staining, ×10 magnification.

Figure 15A:
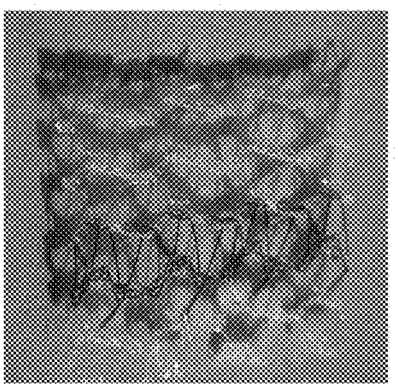
Figure 15B:
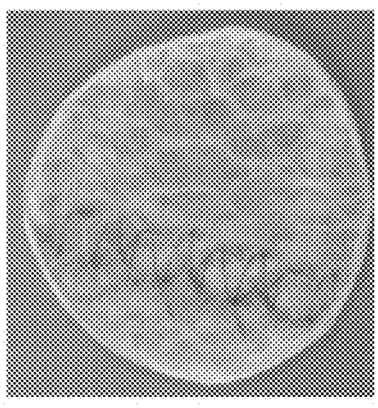
Figure 15C:
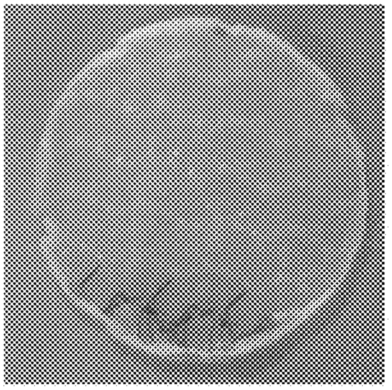
Figure 15D:
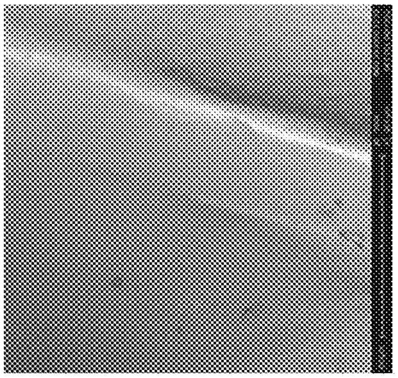

FIGS. 15A-D are images depicting the NET-NFL-ECM device. A synthetic Net (Prolift, Ethicon) (FIG. 15A) is coated by nanofibers layer (NFL) using electrospinning of either PCL, PLGA or a combination of PCL/PLGA nanofibers (FIG. 15B). The coated mesh was used as a substrate for MPC culturing and ECM secretion during 4 weeks in the presence of BHK medium. The hybrid device is subjected to acellularization process and then to lyophilization (FIG. 15C). SEM analysis of the hybrid NET-NFL-ECM device is shown in FIG. 15D and demonstrate that the ECM fully covers the NFL.

Figure 16A:
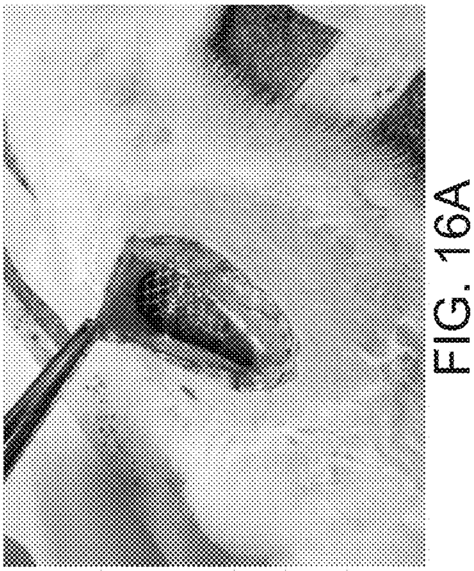
Figure 16B:
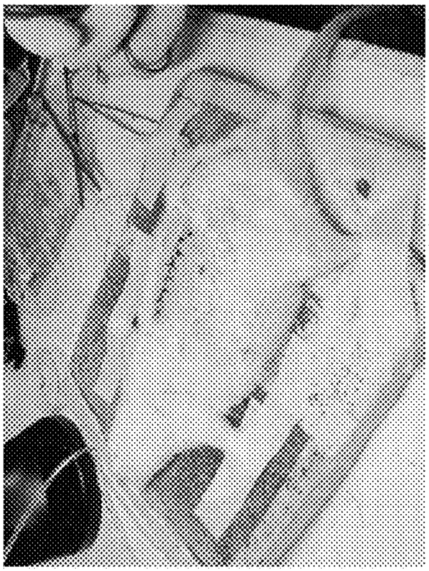
Figure 16C:
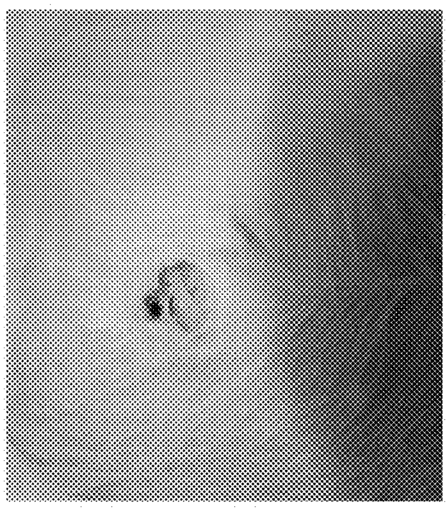
Figure 16D:
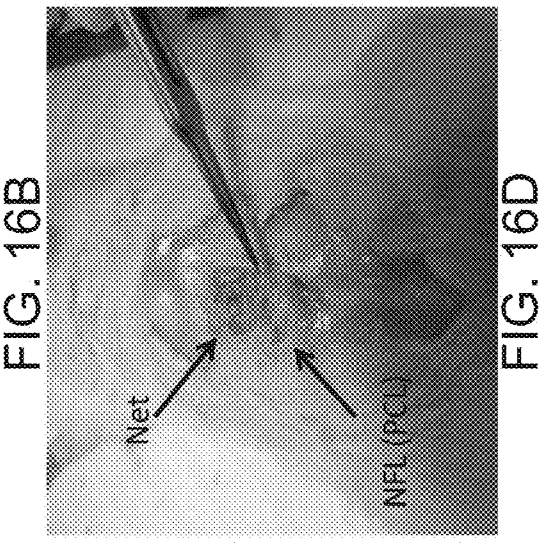

FIGS. 16A-D are images depicting Net transplantation in the rat abdominal wall. Two control implants, Net (prolift, Ethicon) and NFL (30 μm wideness), no ECM) were transplanted in the abdominal wall of one rat. Following 8 weeks the rats were sacrificed, the implant area was exposed and a sample from the implant surrounding tissue was subjected to histology analysis. FIG. 16A—incision of the rat skin and peritoneum muscle, and implantation of the hybrid device. FIG. 16B—incision suturing post transplantation. FIG. 16C—the Net implant 8 weeks post transplantation; FIG. 16D—the NFL implant 8 weeks post transplantation. Note that while the Net implant was extruded out of the transplantation site to below the skin (FIG. 16C), the NFL implant was in the right tissue position, nicely coated with fibrotic tissue (FIG. 16D).

Figure 17A:
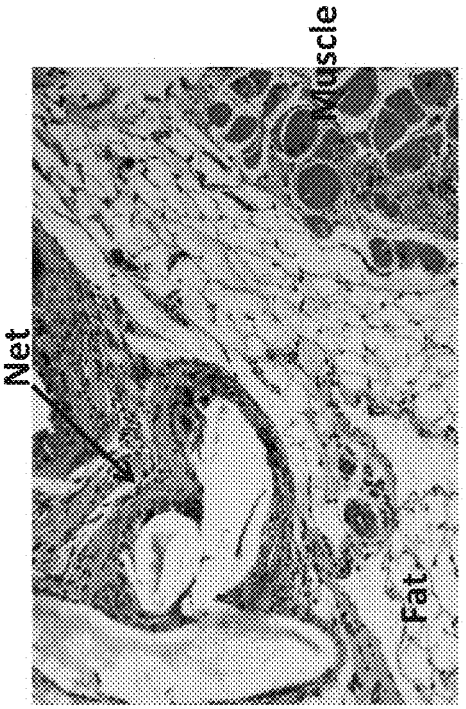
Figure 17B:
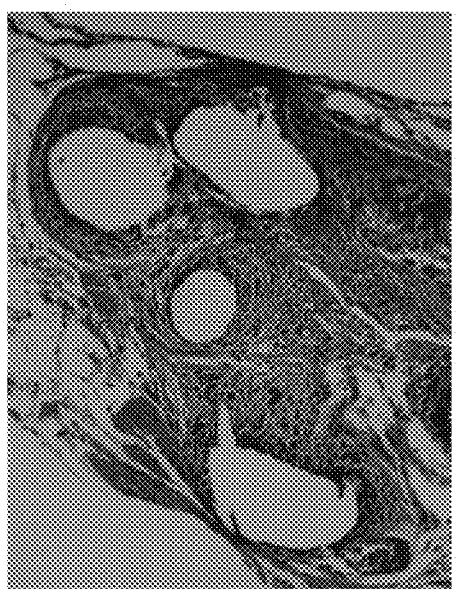
Figure 17C:
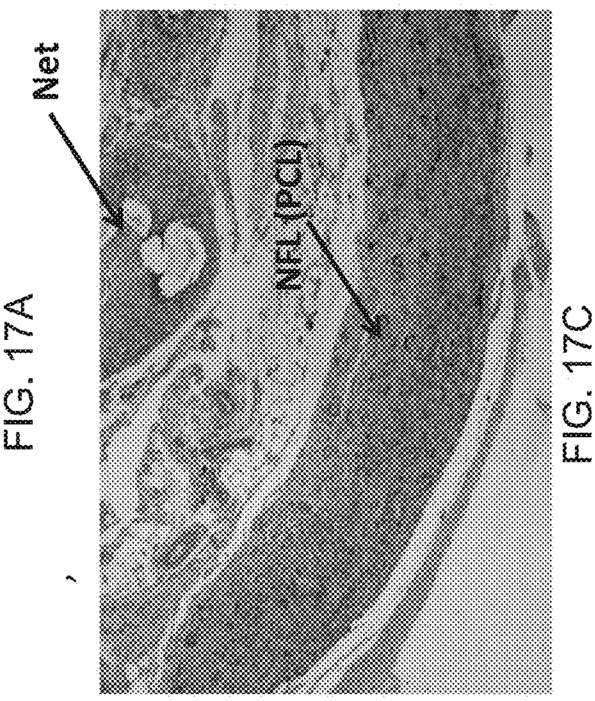
Figure 17D:
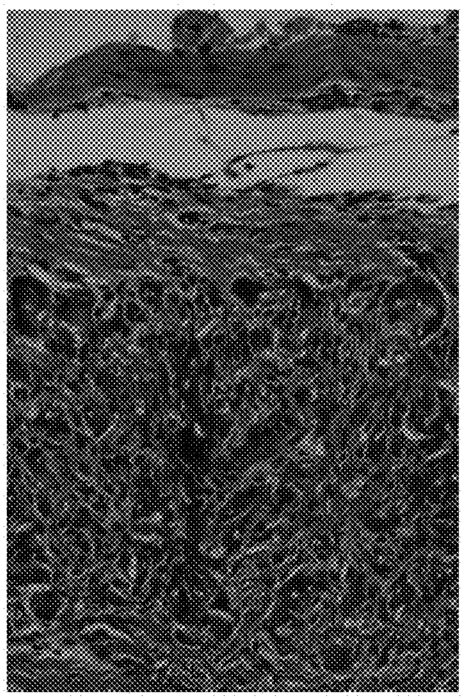

FIGS. 17A-D are microscopic images depicting histology of rat tissues surrounding the control implants; Net scaffold (FIGS. 17A-B) and NFL scaffold (FIGS. 17C-D). Rats were implanted as described in FIGS. 16A-D and histological analysis was performed 8 weeks post transplantation. FIG. 17A H&E staining, ×4 magnification; Note the location of the Net implant within the fat tissue and external to the muscle tissue. These results are in correlation with the extrusion observation shown at FIG. 16C. FIG. 17B—TC staining, ×10 magnification; Note the accumulation of immune cells around the Net fibers. FIG. 17C—H&E staining, ×10 magnification; Note that the NFL implant is well located along the muscle tissue (the original implantation site), while some Net residues are also seen at the fat tissue. FIG. 17D—TC staining, ×20 magnification; Note the granuloma and giant cells within NFL made of PCL Nanofibers. The NFL is surrounded by fibrous collagen structure.

Figures 18A, 18B, 18C:
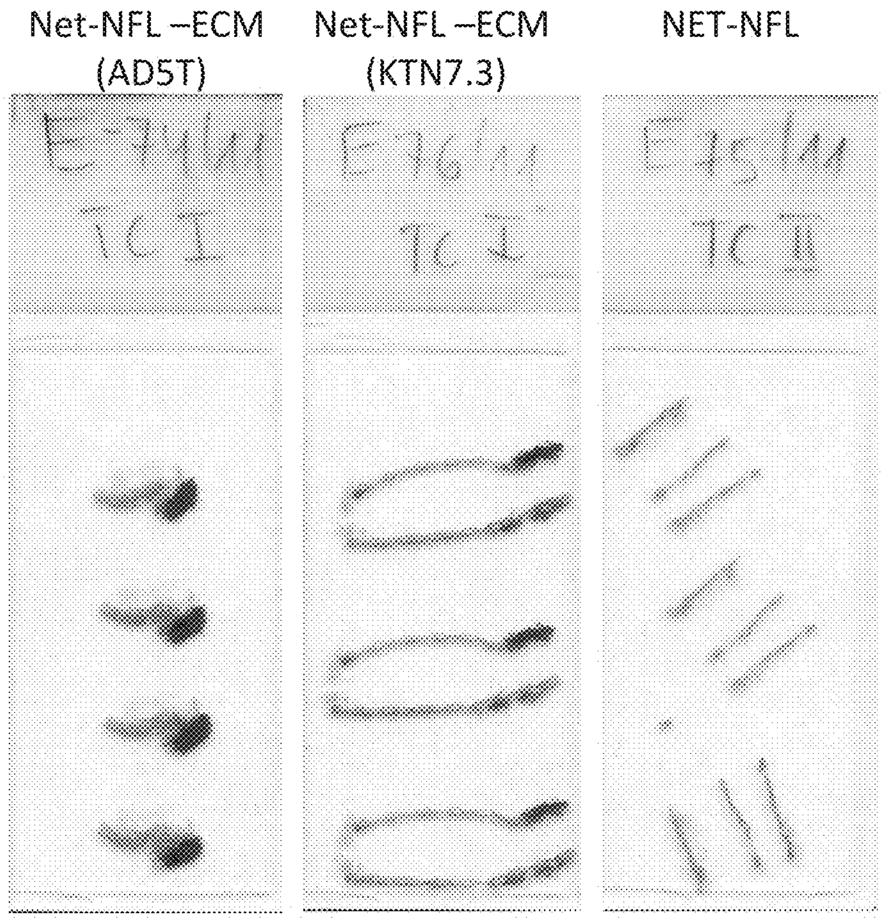

FIGS. 18A-C are photographs of microscopic slides showing slices obtained from paraffin sections depicting Net-NFL (Nanofiber layers) implants following transplantation in the rat abdominal wall. NFL implants were generated using the Prolift™ (Ethicon, Sommerville, N.J., USA) net coated with 30 μm PCL nanofibers, which was used as a substrate for culturing either adult adipose derived MSCs—AD5T [Net-NFL-ECM (AD5T); FIG. 18A] or HFKT-iPSCs-Cre KTN7.3 MPCs [Net-NFL-ECM (KTN7.3); FIG. 18B), or without culturing of MPCs and thus without ECM (Net-NFL, FIG. 18C). Following 4 weeks of culturing, the hybrid devices were subjected to an acellularization procedure and transplanted into the rat abdominal wall. Two duplicates were transplanted from each scaffold type. Eight weeks post transplantation the implants were removed along with the surrounding tissue, stained with Trichrome and photographed. Note the width and connection with the rat muscle tissue of the different implants. The Net-NFL without ECM is very thin and almost no new rat tissues were generated within this implant, while the implants including ECM are much wider, with a clear regeneration of rat's new tissue. Also, the implants made of Net-NFL-ECM are connected to the rat muscle tissue while the Net-NFL devoid of ECM is not connected to the rat muscle tissue.

Figure 18D:
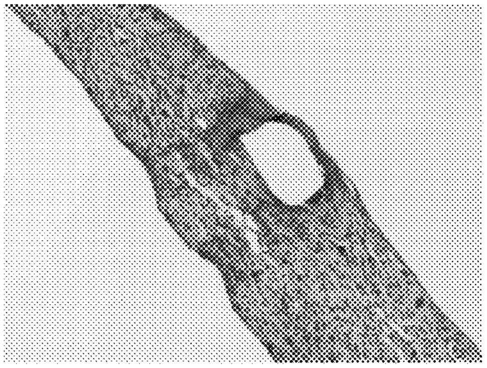
Figure 18E:
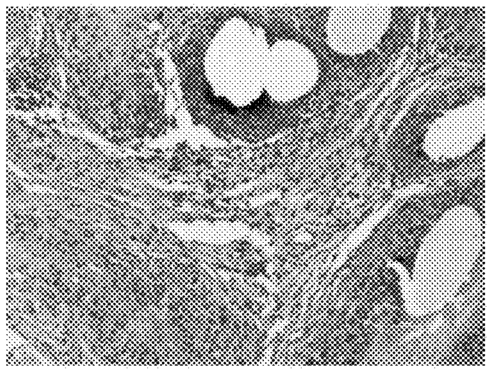
Figure 18F:
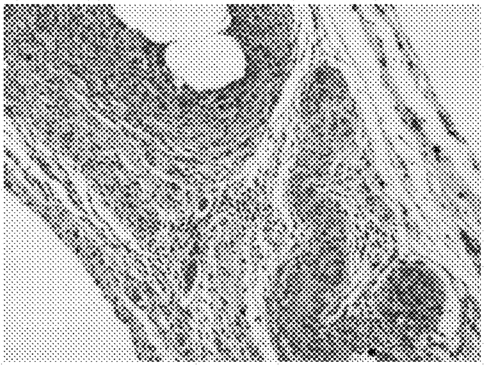

FIGS. 18D-F are photographs of microscopic images depicting histological analysis of the NFL implants 8 weeks post transplantation as described in the description of FIGS. 18A-C above. The histological sections were stained with H&E staining (magnification ×10). Note the significant new generation of blood vessels in implants made of NET-NFL-ECM derived from HFKT-iPSCs-Cre KTN7.3 MPCs (FIG. 18F), as compared to implants made of NET-NFL-ECM derived from AD5T cells (FIG. 18E), and the absence of any blood vessels in tissues implanted with the Net-NFL devoid of ECM (FIG. 18D).

Figures 18G, 18H, 18I, 18J, 18K, 18L, 18M, 18N, 18O:
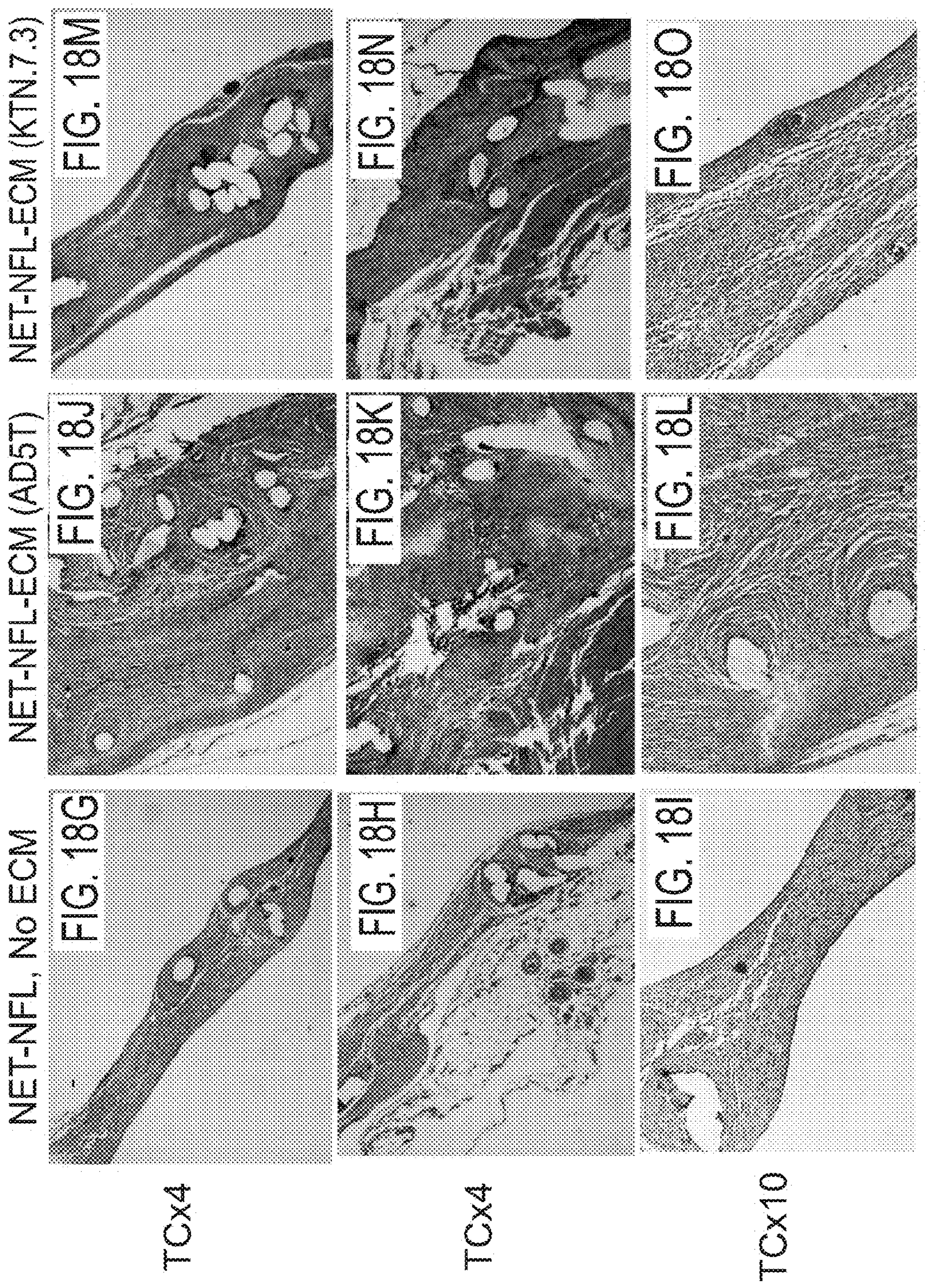

FIGS. 18G-O are photographs of microscopic images depicting histological analysis of the NFL implants 8 weeks post transplantation as described in the description of FIGS. 18A-C above. The histological sections were stained with TC staining and show the localization of the implants within the rat tissues. Magnifications are ×4 (FIGS. 18G, J, M, H, K and N) and ×10 (FIGS. 18I, L and O). Note that while the Net-NFL implant was located at the external fat tissue (FIG. 18H), the Net-NFL-ECM implants were located at their original site near the rat's muscle tissue (FIGS. 18K and N). FIGS. 18I, L and O demonstrate that no significant immune response occurred around the implants, but massive fibrous collagen structure was generated within the ECM derived implants (FIGS. 18L and O).

DESCRIPTION OF SPECIFIC EMBODIMENTS OF THE INVENTION

The present invention, in some embodiments thereof, relates to an isolated population of mesenchymal progenitor cells, methods of generating same, and using same for producing massive amounts of extracellular matrix which can be used for various tissue regeneration and repair applications.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have uncovered a novel method of isolating extracellular matrix (ECM) from pluripotent stem cells.

Thus, as described in the Examples section which follows, the present inventors were capable following laborious experimentations to isolate a novel population of mesenchymal progenitor cells (MPCs) from embryoid bodies (FIGS. 1A-H, Example 1 of the Examples section which follows). About 80-100% of the isolated MPCs are characterized by the CD29+/CD44+/CD105+/CD73+/CD90+/CD45−/CD34− expression signature (FIG. 2H, Example 2 of the Examples section which follows). In addition, while MPCs isolated from the pluripotent stem cells were capable of differentiation into the chondrogenic lineages in a similar manner as did adipose-derived mesenchymal stem cells (FIGS. 3I-L, Example 3), the MPCs isolated from the pluripotent stem cells exhibited a markedly reduced differentiation ability towards the adipogenic lineage as determined by Oil-Red O staining (FIGS. 3F-H; Example 3) when compared to adipose-derived mesenchymal stem cells (FIG. 3E; Example 3). Further RT-PCR analyses revealed a markedly reduced expression level of adipogenic markers such as leptin, adiponectin, Adipocyte protein 2 (AP2) and Lipoprotein lipase (LPL) in MPCs as compared to the level in adipose MSCs (FIG. 13B-E; Example 3). In addition, MPCs isolated from iPSCs exhibited a markedly increased expression of Alizarine red as compared to MPCs isolated from hESCs or MSCs from an adipose source (FIGS. 4A-J; Example 3). As is further described in the Examples section which follows, the ECM produced by the MPCs included Collagen, actin, vimentin, fibronectin, laminin, decorin, tensacin C and elastin (FIGS. 5A-X, 6A-H; Example 4 of the Examples section which follows). In addition, when culturing the MPCs on nanofibers produced by electrospinning the present inventors obtained a hybrid device in which the ECM penetrate within internal layers of the nanofiber (FIGS. 7A-H, 8A-F, 9A-F; Example 5 of the Examples section which follows). Moreover, in vivo transplantation of the hybrid device in injured tissues of animals was found to be superior in terms of compatibility and bioactivity over implantation of synthetic meshes (FIGS. 10A-H, 11A-D, 12A-F; Example 6 of the Examples section which follows). Thus, transplantation into rats of a device composed of PLGA nanofiber layers (NFL) and ECM generated from the MPCs (e.g., the HFKT-iPSCs Cre KTN7.3 MPCs) resulted in good integration into the host tissue with the emergence of new and large blood vessels at the implant site, with a reduced host immune response as compared to NFLs without the ECM (FIGS. 14A-I, Example 7). Furthermore, transplantation of a device composed of a synthetic mesh (net), nanofiber layers (e.g., PCL, PLGA or a combination thereof), and ECM generated from MPCs resulted in a better integration into the host tissue as compared to transplantation of the synthetic mesh alone (FIGS. 16A-D, and 17A-D; Example 8) or as compared to a device made of the net-NFL and ECM generated from adult MSCs (e.g., AD5T) (FIGS. 18D-F; Example 8). In addition, while no significant immune response occurred around any of the implants (FIGS. 18I, L and O), a massive fibrous collagen structure was generated within the ECM-derived implants (FIGS. 18L and O; Example 8), demonstrating that these implants also contributes to angiogenesis and integration of the implant within the rat tissues. These results demonstrate the production of isolated ECM, a device made of nanofibers and ECM, with or without a synthetic mesh, which are suitable for tissue regeneration and repair.

Thus, according to an aspect of some embodiments of the invention there is provided a method of generating mesenchymal progenitor cells from embryoid bodies (EBs). The method is effected by: (a) dissociating the EBs into cell aggregates, (b) culturing the cell aggregates in a culture medium so as to expand a population of adherent cells by at least 2 folds, and (c) dissociating the adherent cells to single cells, and (d) culturing the single cells for at least one passage in a culture medium which comprises ascorbic acid but being devoid of dexamethasone, thereby generating the mesenchymal progenitor cells from the embryoid bodies.

As used herein the phrase "mesenchymal progenitor cells (MPCs)" refers to cells which are not terminally differentiated but exhibit a reduced differentiation potential to mesenchymal cell lineages as compared to naturally occurring mesenchymal stem cells derived from an adult tissue.

As used herein the phrase "mesenchymal stem cells (MSCs)" refers to cells derived from an adult tissue which are capable of differentiation into at least cells of an osteogenic lineage (e.g., osteoblasts), cells of an adipogenic lineage (e.g., adipose cells), and cells of a chondrogenic lineage (e.g., chondrocytes).

As used herein the phrase "embryoid bodies" refers to three dimensional multicellular aggregates of differentiated and undifferentiated cells derivatives of three embryonic germ layers.

Embryoid bodies are formed upon the removal of embryonic stem cells (ESCs) or induced pluripotent stem cells (iPSCs) from feeder layers or feeder cells-free culture systems. ESCs and/or iPSCs removal can be effected using type IV Collagenase treatment for a limited time. Following dissociation from the culturing surface, the cells are transferred to tissue culture plates containing a culture medium supplemented with serum and amino acids.

During the culturing period, EBs are further monitored for their differentiation state. Cell differentiation can be determined upon examination of cell or tissue-specific markers which are known to be indicative of differentiation. For example, to EB-derived-differentiated cells may express the neurofilament 68 KD which is a characteristic marker of the ectoderm cell lineage.

The differentiation level of the EB cells can be monitored by following the loss of expression of Oct-4, and the increased expression level of other markers such as α-fetoprotein, NF-68 kDa, α-cardiac and albumin Methods useful for monitoring the expression level of specific genes are well known in the art and include RT-PCR, semi-quantitative RT-PCR, Northern blot, RNA in situ hybridization, Western blot analysis and immunohistochemistry.

Embryoid bodies can be generated from pluripotent stem cells of various primates and mammals such as human, monkeys and rodents (e.g., mouse, rat).

According to some embodiments of the invention, the embryoid bodies are obtained from human embryoid bodies.

According to some embodiments of the invention, the embryoid bodies are obtained by spontaneous differentiation of pluripotent stem cells.

The phrase "embryonic stem cells" refers to embryonic cells which are capable of differentiating into cells of all three embryonic germ layers (i.e., endoderm, ectoderm and mesoderm), or remaining in an undifferentiated state. The phrase "embryonic stem cells" may read on cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrulation stage blastocyst (see WO2006/040763) and embryonic germ (EG)

cells which are obtained from the genital tissue of a fetus any time during gestation, preferably before 10 weeks of gestation.

The embryonic stem cells of some embodiments of the invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; and Gardner et al., [Fertil. Steril. 69: 84, 1998].

It will be appreciated that commercially available stem cells can also be used according to some embodiments of the invention. Human ES cells can be purchased from the NIH human embryonic stem cells registry [Hypertext Transfer Protocol://grants (dot) nih (dot) gov/stem_cells/registry/current (dot) htm]. Non-limiting examples of commercially available embryonic stem cell lines are BG01, BG02, BG03, BG04, CY12, CY30, CY92, CY10, TE03, TE32, CHB-4, CHB-5, CHB-6, CHB-8, CHB-9, CHB-10, CHB-11, CHB-12, HUES 1, HUES 2, HUES 3, HUES 4, HUES 5, HUES 6, HUES 7, HUES 8, HUES 9, HUES 10, HUES 11, HUES 12, HUES 13, HUES 14, HUES 15, HUES 16, HUES 17, HUES 18, HUES 19, HUES 20, HUES 21, HUES 22, HUES 23, HUES 24, HUES 25, HUES 26, HUES 27, HUES 28, CyT49, RUES3, WA01, UCSF4, NYUES1, NYUES2, NYUES3, NYUES4, NYUES5, NYUES6, NYUES7, UCLA 1, UCLA 2, UCLA 3, WA077 (H7), WA09 (H9), WA13 (H13), WA14 (H14), HUES 62, HUES 63, HUES 64, CT1, CT2, CT3, CT4, MA135, Eneavour-2, WIBR1, WIBR2, WIBR3, WIBR4, WIBR5, WIBR6, HUES 45, Shef 3, Shef 6, BJNhem19, BJNhem20, SA001, SA001.

In addition, ES cells can be obtained from other species as well, including mouse (Mills and Bradley, 2001), golden hamster [Doetschman et al., 1988, Dev Biol. 127: 224-7], rat [Iannaccone et al., 1994, Dev Biol. 163: 288-92] rabbit [Giles et al. 1993, Mol Reprod Dev. 36: 130-8; Graves & Moreadith, 1993, Mol Reprod Dev. 1993, 36: 424-33], several domestic animal species [Notarianni et al., 1991, J Reprod Fertil Suppl. 43: 255-60; Wheeler 1994, Reprod Fertil Dev. 6: 563-8; Mitalipova et al., 2001, Cloning. 3: 59-67] and non-human primate species (Rhesus monkey and marmoset) [Thomson et al., 1995, Proc Natl Acad Sci USA. 92: 7844-8; Thomson et al., 1996, Biol Reprod. 55: 254-9].

Extended blastocyst cells (EBCs) can be obtained from a blastocyst of at least nine days post fertilization at a stage prior to gastrulation. Prior to culturing the blastocyst, the zona pellucida is digested [for example by Tyrode's acidic solution (Sigma Aldrich, St Louis, Mo., USA)] so as to expose the inner cell mass. The blastocysts are then cultured as whole embryos for at least nine and no more than fourteen days post fertilization (i.e., prior to the gastrulation event) in vitro using standard embryonic stem cell culturing methods.

EG cells are prepared from the primordial germ cells obtained from fetuses of about 8-11 weeks of gestation (in the case of a human fetus) using laboratory techniques known to anyone skilled in the arts. The genital ridges are dissociated and cut into small chunks which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., [Proc. Natl. Acad. Sci. USA 95: 13726, 1998] and U.S. Pat. No. 6,090,622.

Induced pluripotent stem cells (iPS; embryonic-like stem cells), are cells obtained by de-differentiation of adult somatic cells which are endowed with pluripotency (i.e., being capable of differentiating into the three embryonic germ cell layers, i.e., endoderm, ectoderm and mesoderm). According to some embodiments of the invention, such cells are obtained from a differentiated tissue (e.g., a somatic tissue such as skin) and undergo de-differentiation by genetic manipulation which re-program the cell to acquire embryonic stem cells characteristics.

According to some embodiments of the invention, the induced pluripotent stem cells are formed by inducing the expression of Oct-4, Sox2, Kfl4 and c-Myc in a somatic stem cell. Thus, iPS cells can be generated by retroviral transduction of somatic cells such as fibroblasts, hepatocytes, gastric epithelial cells with transcription factors such as Oct-3/4, Sox2, c-Myc, and KLF4 [Yamanaka S, Cell Stem Cell. 2007, 1(1):39-49; Aoi T, et al., Generation of Pluripotent Stem Cells from Adult Mouse Liver and Stomach Cells. Science. 2008 Feb. 14. (321:699-702); IH Park, Zhao R, West J A, et al. Reprogramming of human somatic cells to pluripotency with defined factors. Nature 2008; 451:141-146; K Takahashi, Tanabe K, Ohnuki M, et al. Induction of pluripotent stem cells from adult human fibroblasts by defined factors. Cell 2007; 131:861-872]. Other embryonic-like stem cells can be generated by nuclear transfer to oocytes, fusion with embryonic stem cells or nuclear transfer into zygotes if the recipient cells are arrested in mitosis.

According to some embodiments of the invention, the induced pluripotent stem cells are generated by reprogramming somatic cells with a single polycistronic excisable lentiviral vector (e.g., the STEMCCA vector described in Somers, A., et al. 2010. Generation of transgene-free lung disease-specific human iPS cells using a single excisable lentiviral stem cells cassette. Stem Cells, 28(10):1728-40; Sommer, C. A., et al., 2009. Induced pluripotent stem cell generation using a single lentiviral stem cell cassette. Stem Cells 27, 543-549; each of which is fully incorporated herein by reference.

According to some embodiments of the invention, the somatic cells used for generating the iPSCs are keratinocytes derived from plucked hair follicles.

According to some embodiments of the invention, the iPSCs are derived from plucked human hair follicle keratinocytes (iPS-HFKTs).

According to some embodiments of the invention, the iPSCs are formed from a somatic cell that was reprogrammed with a viral-excisable vector that was further excised from the genome of the iPSCs, essentially as described in as described in Novak et al., 2010 [Cell Reprogram. 2010, 12(6): 665-78)] which is fully incorporated herein by reference.

A non-limiting example of a viral-excisable vector is the lentiviral STEMCCA vector.

According to some embodiments of the invention, the embryoid bodies or the pluripotent stem cells are derived from an individual having a normal karyotype according to the species to which the individual belong. For example, for human individuals, a normal karyotype is of 22XY or 22XX chromosomes.

According to some embodiments of the invention, the embryoid bodies or the pluripotent stem cells are derived from a healthy individual.

According to some embodiments of the invention, the embryoid bodies are cultured on defined, xeno-free, feeder-free culturing systems. Such feeder-free systems (e.g., using low attachment culture dishes) can include a culture medium which is serum-free, and/or xeno-free (i.e., devoid of contamination by another species, for example, devoid of animal contamination of human cells) provides a more defined environment for the EBs, which can be controlled, such as to be free of xeno-contaminant and cellular contaminants.

It should be noted that for therapeutic applications, all media used to culture the cells include synthetic or recombinantly expressed components, such that the cells cultured therein are completely devoid of any xeno-contaminants.

The term "xeno" is a prefix based on the Greek word "Xenos", i.e., a stranger. As used herein the phrase "xeno-free" refers to being devoid of any components which are derived from a xenos (i.e., not the same, a foreigner) species. Such components can be contaminants such as pathogens associated with (e.g., infecting) the xeno species, cellular components of the xeno species or a-cellular components (e.g., fluid) of the xeno species.

According to some embodiments of the invention, the EBs used by the method of some embodiments of the invention are derived from about 8-14 days of differentiation of human EBs, e.g., about 8, 9, 10, 11, 12, 13 or 14 day-old human EBs.

According to some embodiments of the invention, the EBs used by the method of some embodiments of the invention are 10-day-old human EBs.

It should be noted that the first day of EBs differentiation is considered about 24 hours after the pluripotent stem cells were allowed to differentiate in vitro by removing the pluripotent stem cells from their undifferentiated culture conditions, such as by removing them from feeder layers or from their feeder-free culture systems (e.g., matrix such as an extracellular matrix).

As described, the method of some embodiments of the invention comprises dissociating the EBs into cell aggregates.

According to some embodiments of the invention, each of the aggregates formed by dissociating the EBs comprises about 10-30 cells, e.g., between about 12-28 cells, e.g., between about 15-25 cells, e.g., about 20 cells.

According to some embodiments of the invention, the dissociation of EBs is performed by treatment with Collagenase and optionally also with DNAse I. The Collagenase can be Collagenase B (e.g., available from Roche, catalogue number 11 088 807 001) used in a concentration in the range of about 0.1-5 mg/ml (e.g., in PBS), e.g., about 0.5-3 mg/ml, e.g., about 0.8-2 mg/ml, e.g., about 0.8-1.5 mg/ml, e.g., about 1 mg/ml Collagenase B. The DNAse I (e.g., available from Roche, catalogue number 2139) can be used in a concentration of about 10-500 U/ml, e.g., about 50-350 U/ml, e.g., about 100-200 U/ml, e.g., about 150 U/ml DNAse I.

Incubation with the Collagenase and DNAse I solution can be performed while shaking the vessel containing the EBs, for an incubation time which may vary between about 5-30 minutes, e.g., between about 10-25 minutes, e.g., between about 15-20 minutes, e.g., about 20 minutes. To increase efficiency, the dissociation can be performed at about 37° C. while shaking. The dissociation conditions can be adjusted according to the source or origin of the EBs.

Following is a non-limiting description of dissociation of human EBs into cell aggregates. EBs can be formed from pluripotent stem cells (iPSCs or hESCs) in 10-cm tissue culture plate. Prior to dissociation, the EBs are collected in a 50 ml tube, centrifuged for 3 minutes at 800 rounds per minute (rpm), washed with 5 ml phosphate buffered saline (PBS) and centrifuged again. PBS is then removed and Collagenase B (0.5 ml from a stock of 1 mg/ml of Collagenase in F-12 DMEM medium) and Deoxyribonuclease I (at a final concentration of 0.5 mg/ml are added for an incubation time of about 20 minutes at 37° C. while periodically shaking the EBs. The Collagenase/DNAse reaction are stopped by addition of EBs medium +20% defined FBS (or serum replacement) to the cell aggregates, followed by gentle centrifugation (e.g., for 10 minutes at 1200 rpm).

According to some embodiments of the invention, once the EBs are dissociated to cell aggregates these cell aggregates are further cultured in a culture medium so as to expand a population of adherent cells by at least about 2 folds, e.g., by at least 2.5 folds, about 3 folds, about 4 folds, about 5 folds. The culturing period desired for selection and expansion of the adherent cells is usually between 2-4 days (e.g., 2-3 days).

According to some embodiments of the invention, culturing the cell aggregates is performed on low-adhesive (low-attachment) tissue culture plates (e.g., such as Greiner Bio-One Ltd. Brunel Way, Stroudwater Business ParkGL10 3SX StonehouseGreat Britain). In an exemplary embodiment, the plates are not gelatin-coated plates.

According to some embodiments of the invention, culturing the cell aggregates is performed on non-coated plates (e.g., plates which are not coated by for example, gelatin).

The culture medium which is used for culturing the cell aggregates can be any culture medium suitable for growing EBs. The medium can be supplemented with serum (e.g., human serum, bovine serum) or serum replacement and additional additives. For example, such a culture medium can be a basic culture medium [e.g., DMEM (an optimized Dulbeco's modified Eagle's medium for ES cells; Gibco-BRL, Gaithersburg, Md.)] supplemented with serum or serum replacement [e.g., 20% Knockout® SR (Gibco-BRL)], glutamine (e.g., 1 mM glutamine), β-mercaptoethanol (e.g., 0.1 mM β-mercaptoethanol), and nonessential amino acids (e.g., 1% nonessential amino acids).

Additionally or alternatively, the culture medium which is used for culturing the cell aggregates comprises ascorbic acid.

As used herein "ascorbic acid" refers to the synthetic or naturally occurring ascorbic acid (an organic acid with antioxidant properties), also known as vitamin C, which is suitable for culturing cells (e.g., sterile preparation).

The ascorbic acid which is included in the culture medium of the method of this aspect of the present invention can be obtained from Sigma (St Louis, Mo., USA) and is provided at a concentration of at least about 20 μg/ml, more preferably, at least about 30 μg/ml, preferably, at a concentration which is selected from the range of about 10-500 μg/ml, e.g., about 50-300 μg/ml, e.g., about 50-200 μg/ml, e.g., about 50-150 μg/ml, e.g., about 80-120 μg/ml, e.g., about 100 μg/ml.

According to some embodiments of the invention, the culture medium which comprises ascorbic acid is devoid of dexamethasone.

As used herein the phrase "devoid of dexamethasone" refers to a medium which includes less than about 1% of dexamethasone, e.g., less than 0.5%, less than about 0.1%, less than about 0.05%, less than about 0.01%, e.g., less than 0.005% of dexamethasone.

The culture medium, which comprises ascorbic acid, can further include about 5-30% of serum or serum replacement (e.g., a xeno-free serum replacement), e.g., about 10-20% serum or serum replacement.

In addition, the culture medium which comprises ascorbic acid may further include glutamine, non-essential amino acids, antibiotics, sodium Pyruvate and 2-mercaptoethanol.

A non-limiting example of a culture medium which comprises ascorbic acid and which is suitable for culturing the cell aggregates include the BHK medium which consists of Glasgow Minimum Essential Medium (GMEM) with glutamine (GIBCO-Invitrogen, Paisley, UK) and supplemented with 10% lot specific fetal bovine serum (FBS) (Hyclone, Logan, Utah, USA), 1% penicillin (10,000 U/mL)-streptomycin (10 mg/mL) (Biological industries, Beit Haemek, Israel), 1% non-essential amino acids (NEAA) ×100, 1 mM sodium Pyruvate, 0.75 mM 2-mercaptoethanol (all from GIBCO-Invitrogen, Paisley, UK) and 100 μg/ml L-ascorbic acid 2-phosphate (Sigma, Rehovot, Israel).

In exemplary embodiments the cell aggregates are first cultured for one day in an EBs-culture medium (devoid of ascorbic acid, e.g., an EB medium) and are then cultured in a culture medium which comprises ascorbic acid (e.g., the BHK medium) for additional 2-3 days.

As described, the method of some embodiments of the invention comprises dissociating the expanded adherent cells into single cells (e.g., when each cell does not form contact with another cell in the same cell suspension). The dissociation is performed under conditions which enable separation of cell aggregates/clumps while preserving the viability of the separated cells of the dissociated EBs. For example, an enzyme such as Trypsin (e.g., at a concentration of 0.25%) can be used for 5-15 minutes at 37° C. The single cell suspensions can be further filtered through a Mesh (Cell strainer, 70 μm Nylon, BD Falcon, BD Biosciences, MA, USA) such that only single cells (and not cell clusters are isolated.

As described above, once single cells are obtained they are further cultured for at least one passage in a culture medium which comprises ascorbic acid but being devoid of dexamethasone.

Culturing of the single cells can be performed by seeding the single cells in a culture vessel (e.g., a two-dimensional or three-dimensional culture vessel) or into a matrix (e.g., a cell supporting scaffold, such as a nanofiber or a two-dimensional matrix) in the presence of a culture medium. When cultured on a two-dimensional culture system the single cells can be seeded at a concentration of about 2-200 cells/$cm^2$, e.g., 1-100×$10^5$ cells/$cm^2$, e.g., 50-100×$10^5$ cells/$cm^2$, e.g., about 50×$10^5$ cells/$cm^2$.

Once cultured, the culture medium can be replaced every day or every other day. During culturing, the cells can be monitored for their morphology. A characteristic cell morphology is of "fibroblast-like cells", e.g., flat, elongated cells with wide cytoplasm surrounding an elliptical, speckled nucleus, with abundant rough endoplasmic reticulum. It should be noted that during ongoing passaging the MPCs are big and flat, but during ECM generation the cells become smaller, condensed and generating several cell layers.

It should be noted that the concentration of the cells can be determined by counting a sample of the cells, using any known method, such as Triphan-blue.

When the cells exhibit subconfluency (e.g., about 80-90% confluency), the cultured cells are passaged. Passaging can be performed by dissociating cells from the wall of the culture vessel using e.g., type IV Collagenase [e.g., at a concentration of 0.1% (gram per 100 ml PBS solution) for 20-60 minutes] followed by trypsinization (using e.g., 0.1% trypsin-EDTA for 5-10 minutes), counting the single cells and splitting the cells to 2-3 culture vessels.

According to some embodiments of the invention, the first passaging occurs after 2-10 days of the initial seeding, e.g., 2-8 days, 2-6 days, 2-4 days of the initial seeding.

According to some embodiments of the invention, the cell culture is subjected to culture passaging every 4-8 days, e.g., culture passaging occurs every 3-8 days, e.g., every 4 days.

Culturing can be performed for several passages, e.g., from 1-15 passages, e.g., 1-2, 1-3, 1-4, 1-5, 1-6, 1-7, 1-8, 1-9, 1-10, 1-11, 1-12, 1-13, 1-14 or 1-15 passages, or until senescence.

As used herein the term "senescence" refers to the stage in which the cells lose their ability to divide, or significantly reduce their growth rate.

Thus, using the method of some embodiments of the invention a novel population of mesenchymal progenitor cells can be isolated.

Thus, according to an aspect of some embodiments of the invention, there is provided an isolated population of cells comprising at least about 60%, e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, e.g., 100% mesenchymal progenitor cells, wherein differentiation into an adipogenic lineage of the mesenchymal progenitor cells is reduced by at least about 50%, e.g., by about 55%, about 60%, about 65%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, e.g., at least about 99%, e.g., 100% as compared to differentiation of mesenchymal stem cells selected from an adult adipogenic tissue under identical assay conditions.

Quantization of the degree of differentiation into an adipogenic lineage can be performed by various methods (e.g., assays). For example, the number of fat drops per cells in the culture can be measured using for example, an image analysis system (e.g., ImagePro software). Additionally or alternatively, the differentiation to adipogenic lineage can be determined by quantitative Real Time PCR using adipogenic differentiation markers as: Peroxisome-proliferator-activated receptor-γ [PPAR γ; using e.g., primers specific to GenBank Accession Nos. NM_005037.5 (SEQ ID NO:55), NM_015869.4 (SEQ ID NO:56), NM_138711.3 (SEQ ID NO:57) and/or NM_138712.3 (SEQ ID NO:58)], CCAAT/enhancer-binding proteins beta [C/EBPβ; using e.g., primers specific to GenBank Accession NO. NM_005194.2 (SEQ ID NO:59)], Leptin [using e.g., primers specific to GenBank Accession NO. NM_000230.2 (SEQ ID NO:54)] and adiponectin [using e.g., primers specific to GenBank Accession NO. NM_001177800.1 (SEQ ID NO:53) and/or NM_004797.3 (SEQ ID NO:60)].

As shown in FIGS. 4A-J and described in Example 3 of the Examples section which follows, the MPCs of some embodiments of the invention exhibit increased calcific deposition as determined by Alizarin Red staining, indicative of the increased osteogenic differentiation potential.

According to some embodiments of the invention, the isolated population of mesenchymal progenitor cells are characterized by increased osteogenic differentiation potential as compared to the osteogenic differentiation potential of adipose-derived MSCs under identical assays conditions.

According to some embodiments of the invention, the isolated population of cells is characterized by at least 20% higher calcific deposition as compared to the calcific deposition by adipose-derived adult mesenchymal stem cells under identical assay conditions, e.g., at least about 30%, at least about 40%, at least about 50%, at least about 60%, at least about 65%, at least about 70%, e.g., about 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, e.g., 100%, 200%, 300%, 400%, 500%, 600%, 700%, 800%, 900% or 1000% higher calcific deposition as compared to the calcific deposition observed from adipose-derived adult mesenchymal stem cells under identical assay conditions.

Quantification of the calcific deposition can be determined by various methods, such as by Alizarin Red staining.

According to some embodiments of the invention, the isolated population of cells comprises at least about 60%, e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, e.g., 100% of mesenchymal progenitor cells which express CD105 (i.e., exhibit a CD105+ expression pattern).

According to some embodiments of the invention, the isolated population of cells comprises between 80-100% CD105 positive cells.

As used herein the phrases "express" or "not express" refer to cells having a positive (+) or negative (−) expression profile, respectively, of a certain marker (e.g., gene or gene product).

CD105, also known as endoglin (gene symbol ENG) is a homodimeric transmembrane protein, a major glycoprotein of the vascular endothelium. Endoglin is a component of the transforming growth factor beta receptor complex and it binds TGFB1 and TGFB3 with high affinity. There are two known variants of endoglin: isoform 1 (GenBank Accession No. NP_001108225.1; SEQ ID NO:61) and isoform 2 (GenBank Accession No. NP_000109.1; SEQ ID NO:62).

According to some embodiments of the invention, detection of CD105 expression can be performed using an anti CD105 antibody.

Suitable CD105 antibodies which can be used to detect CD105 on the cells include R-Phycoerythrin (PE)-conjugated anti-CD105 (eBioscience), Fluorescein isothiocyanate (FITC)-conjugated anti-CD105 (ABCAM), APC-conjugated anti-CD105 (eBioscience).

According to some embodiments of the invention, the isolated population of cells comprises at least about 60%, e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, e.g., 100% of mesenchymal progenitor cells which express CD90 (i.e., exhibit a CD90+ expression pattern).

CD90 (Cluster of Differentiation 90), also known as Thy-1 cell surface antigen (THY1) is a 25-37 kDa heavily N-glycosylated, glycophosphatidylinositol (GPI) anchored conserved cell surface protein with a single V-like immunoglobulin domain, originally discovered as a thymocyte antigen.

A non-limiting example of a suitable CD90 antibodies which can be used to detect the CD90 surface marker on cells include, the mouse anti CD90 PE conjugated (Biolegend).

According to some embodiments of the invention, the isolated population of cells comprises at least about 60%, e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, e.g., 100% of mesenchymal progenitor cells which are characterized by a CD105+/CD90+/CD73+/CD44+/CD29+ expression signature (i.e., express the CD105/CD90/CD73/CD44/CD29 cell surface markers).

According to some embodiments of the invention, the isolated population of cells comprises at least about 60%, e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, e.g., 100% of mesenchymal progenitor cells which are characterized by a CD45−/CD34− signature (i.e., do not express the CD45 and CD34 cell surface markers).

According to some embodiments of the invention, the mesenchymal progenitor cells are capable of forming extracellular matrix.

According to some embodiments of the invention, the isolated population of mesenchymal progenitor cells maintain the ability to form extracellular matrix for at least 1, 2, 3, 4, 5, 6, 7, 8, 9, 10, 11, 12, 13, 14 and 15 passages, e.g., between 1-15 passages.

According to an aspect of some embodiments of the invention there is provided a method of isolating an extracellular matrix, comprising: (a) culturing the mesenchymal progenitor cells of some embodiments of the invention under conditions which induce production of extracellular matrix from the mesenchymal progenitor cells, (b) isolating the extracellular matrix produced by the mesenchymal progenitor cells, thereby isolating the extracellular matrix.

As used herein the phrase "extracellular matrix (ECM)" refers to a material produced and secreted by living cells which provides structural support for cells cultured therein.

In a mammalian tissue the ECM is deposited outside of the cells into the interstitial matrix and the basement membrane.

Generally, the ECM includes fibrous elements (particularly collagen, elastin, or reticulin), cell adhesion polypeptides (e.g., fibronectin, laminin and adhesive glycoproteins), and space-filling molecules [usually glycosaminoglycans (GAG), proteoglycans]. Other substantial components are growth factors and cytokines, which are present within the ECM in very small quantities but play a critical role as potent modulators of cell behavior.

According to some embodiments of the invention, the ECM produced and secreted by the cells is capable of carrying (e.g., supporting) cells or cell components.

Culturing the mesenchymal progenitor cells (MPCs) can be performed on any culture vessel (e.g., a two-dimensional culture plate, or a three-dimensional culture vessel), with or without additional substrate or scaffold to which the cells may attach. Thus, the MPCs can be cultured on a low-adhesive tissue culture plate and the ECM can be deposited in layers on the surface of the culture plate. Additionally or alternatively, the MPCs can be cultured on a scaffold, to thereby form a three-dimensional ECM structure.

According to some embodiments of the invention, the substrate or scaffold on which the MPCs are cultured is an electrospun element.

According to some embodiments of the invention, the culturing is performed on an electrospun element. It should be noted that as in any culturing method, the cells are cultured on the electrospun element (e.g., nanofibers) in the presence of a suitable culture medium, such as a medium which comprises ascorbic acid (e.g., the BHK medium). The concentration of MPCs seeded on the nanofibers can be selected from about $0.5\text{-}1.5\times10^5$ cells/cm$^2$.

According to some embodiments of the invention, the medium used for culturing the MPCs is devoid of dexamethasone and/or Glycerol 2-phosphate in order to prevent formation of a mineralized ECM.

Manufacturing of electrospun elements can be done by an electrospinning process which is well known in the art. Following is a non-limiting description of an to electrospinning process. One or more liquefied polymers (i.e., a polymer in a liquid form such as a melted or dissolved polymer) are dispensed from a dispenser within an electrostatic field in a direction of a rotating collector. The dispenser can be, for example, a syringe with a metal needle or a bath provided with one or more capillary apertures from which the liquefied polymer(s) can be extruded, e.g., under the action of hydrostatic pressure, mechanical pressure, air pressure and high voltage.

The rotating collector (e.g., a drum) serves for collecting the electrospun element thereupon. Typically, but not obligatorily, the collector has a cylindrical shape. The dispenser (e.g., a syringe with metallic needle) is typically connected to a source of high voltage, preferably of positive polarity, while the collector is grounded, thus forming an electrostatic field between the dispenser and the collector. Alternatively, the dispenser can be grounded while the collector is connected to a source of high voltage, preferably with negative polarity. As will be appreciated by one ordinarily skilled in the art, any of the above configurations establishes motion of positively charged jet from the dispenser to the collector. Inverse electrostatic configurations for establishing motions of negatively charged jet from the dispenser to the collector are also contemplated.

At a critical voltage, the charge repulsion begins to overcome the surface tension of the liquid drop. The charged jets depart from the dispenser and travel within the electrostatic field towards the collector. Moving with high velocity in the inter-electrode space, the jet stretches and solvent therein evaporates, thus forming fibers which are collected on the collector, thus forming the electrospun element.

As used herein, the phrase "electrospun element" refers to an element of any shape including, without limitation, a planar shape and a tubular shape, made of one or more nonwoven polymer fiber(s), produced by a process of electrospinning. When the electrospun element is made of a single fiber, the fiber is folded thereupon, hence can be viewed as a plurality of connected fibers. It is to be understood that a more detailed reference to a plurality of fibers is not intended to limit the scope of the present invention to such particular case. Thus, unless otherwise defined, any reference herein to a "plurality of fibers" applies also to a single fiber and vice versa. The electrospun element is also referred to as a nanofiber hereinafter.

The polymer fibers of the electrospun element can be arranged on a single layer, but, more preferably, the fibers define a plurality of layers hence form a three dimensional structure. The polymer fibers may have a general random orientation, or a preferred orientation, as desired e.g., when the fibers are collected on a cylindrical collector such as a drum, the polymer fibers can be aligned predominantly axially or predominantly circumferentially. Different layers of the electrospun element may have different orientation characteristics. For example, without limiting the scope of some embodiments of the invention to any specific ordering or number of layers, the fibers of a first layer may have a first predominant orientation, the fibers of a second layer may have a second predominant orientation, and the fibers of third layer may have general random orientation.

Various parameters involved in the electrospinning process may vary during the process in a continuous or non-continuous manner. These include, but not limited to: the velocity of the rotating collector, the characteristic of the electrostatic field vector (magnitude and/or direction), the size or shape of the capillary apertures of the dispenser (e.g., the size and/or cross-sectional shape of a needle attached to the dispenser), the dispensing flow rate of the at least one liquefied polymer the viscosity and/or concentration of the liquefied polymer and the concentration of charge control agent.

The characteristic of the electrostatic field vector can be varied during the electrospinning process in more than one way. In one preferred embodiment, the variation of the electric field is effected by varying, preferably continuously, the distance between the dispenser and the collector; in another preferred embodiment, the variation of the electric field is effected by varying, preferably continuously, the potential difference between the dispenser and the collector; in an additional embodiment, the variation of the electrostatic field is effected by varying both the distance and the potential difference in a substantially continues manner.

The polymer used in the electrospinning process for the manufacture of the electrospun element can be a natural, synthetic and/or biocompatible polymer.

The phrase "synthetic polymer" refers to polymers that are not found in nature, even if the polymers are made from naturally occurring biomaterials. Examples include, but are not limited to, aliphatic polyesters, poly(amino acids), copoly (ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, and combinations thereof.

Suitable synthetic polymers for use in the present invention can also include biosynthetic polymers based on sequences found in collagen, elastin, thrombin, fibronectin, starches, poly(amino acid), poly(propylene fumarate), gelatin, alginate, pectin, fibrin, oxidized cellulose, chitin, chitosan, tropoelastin, hyaluronic acid, polyethylene, polyethylene terephthalate, poly(tetrafluoroethylene), polycarbonate, polypropylene and poly(vinyl alcohol), ribonucleic acids, deoxyribonucleic acids, polypeptides, proteins, polysaccharides, polynucleotides and combinations thereof.

The phrase "natural polymer" refers to polymers that are naturally occurring. Non-limiting examples of such polymers include, silk, collagen-based materials, chitosan, hyaluronic acid, alginate and albumin.

As used herein, the phrase "co-polymer" refers to a polymer of at least two chemically distinct monomers. Non-limiting examples of co-polymers include, PLA-PEG, PEGT/PBT, PLA-PGA PEG-PCL and PCL-PLA.

The phrase "biocompatible polymer" refers to any polymer (synthetic or natural) which when in contact with cells, tissues or body fluid of an organism does not induce adverse effects such as immunological reactions and/or rejections and the like. It will be appreciated that a biocompatible polymer can also be a biodegradable polymer.

The phrase "biodegradable polymer" refers to a synthetic or natural polymer which can be degraded (i.e., broken down) in the physiological environment such as by proteases. Biodegradability depends on the availability of degradation substrates (i.e., biological materials or portion thereof which are part of the polymer), the presence of biodegrading materials (e.g., microorganisms, enzymes, proteins) and the availability of oxygen (for aerobic organisms, microorganisms or portions thereof), carbon dioxide (for anaerobic organisms, microorganisms or portions thereof) and/or other nutrients.

Degradable polyesters are one of the widely used synthetic materials for electrospinning because they are biodegradable with metabolizable degradation products. The degradation rate of polyester can be controlled by changing the constitute of the polymer. Examples of biodegradable polymers include, but are not limited to, collagen, fibrin, hyaluronic acid, polylactic acid (PLA), polyglycolic acid (PGA), polycaprolactone (PCL), polydioxanone (PDO), trimethylene carbonate (TMC), calcium sulfate, polyethyleneglycol (PEG), Collagen, PEG-DMA, Alginate, Hydroxyapatite, chitosan, and/or copolymers thereof and/or mixtures thereof. For example, PLGA—Poly(lactic-co-glycolic) acid is the copolymer of both PGA and PLA, being the most popular synthetic polymer for tissue engineering applications because of its excellent biocompatibility and variable degradability obtained by controlled the ratio of PGA:PLA within the copolymer. PCL is a crystalline, biodegradable polymer, which is easily fabricated, and when electrospun exhibits good mechanical properties.

According to some embodiments of the invention, the electrospun element comprises polycaprolactone (PCL).

According to some embodiments of the invention, the electrospun element comprises polycaprolactone (PCL) and poly (lactic-co-glycolic acid) (PLGA), and/or combination thereof (e.g. PCL/PLGA 1:6).

According to some embodiments of the invention, the liquefied polymer can be made of one polymer or more, each can be a polymer or a co-polymer such as described hereinabove.

According to some embodiments of the invention, the liquefied polymer is a mixture of at least one biocompatible polymer and a co-polymer (either biodegradable or non-biodegradable).

Thus, the cultured MPCs produce ECM on the culture vessel or the substrate (e.g., the electrospun element) which can be further isolated.

The term "isolated" as used herein refers to at least partially separated from the natural environment e.g., the cells producing the ECM.

According to some embodiments of the invention, the isolated ECM is at least partially separated from the culture vessel used for growing the cells.

According to some embodiments of the invention, the ECM comprises proteins such as collagens (various types as collagen I, collagen III, IV, V, VI), actin, Vimentin, fibronectin and laminin, desmin, Glucoseaminoglycans (GAGs).

According to some embodiments of the invention, the ECM is a non-mineralized ECM. As used herein the phrase "non-mineralized" ECM refers to an ECM which is substantially devoid of calcium deposits.

According to some embodiments of the invention, the ECM comprises no more than 10% (weight/weight) of calcium deposits, e.g., no more than about 9%, nor more than about 8%, 7%, 6%, 5%, 4%, 3%, 2%, 1% of calcium, e.g., 0% calcium deposits.

In order to make the produced ECM amendable for tissue regeneration or repair applications, the ECM should be devoid of cellular components.

According to some embodiments of the invention, the method further comprising decellularizing the extracellular matrix.

As used herein the phrase "decellularizing the ECM" refers to removal of cells from the ECM.

According to some embodiments of the invention, the isolated ECM is decellularized.

According to some embodiments of the invention, the isolated ECM is devoid of any cellular components (i.e., an acellular ECM).

The phrase "devoid of any cellular components" as used herein refers to being more than about 80%, e.g., more than 81%, 82%, 83%, 84%, 85%, 86%, 87%, 88%, 89%, 90%, 91%, 92%, 93%, 93%, 94%, 95%, 96%, 97%, 98%, 99%, e.g., 100% devoid of the cellular components present in the cell culture which comprises the ECM prior to the decellularization process.

As used herein, the phrase "cellular components" refers to cell membrane components or intracellular components which make up the cell. Examples of cell components include cell structures (e.g., organelles) or molecules comprised in same. Examples of such include, but are not limited to, cell nuclei, nucleic acids, residual nucleic acids (e.g., fragmented nucleic acid sequences), cell membranes and/or residual cell membranes (e.g., fragmented membranes) which are present in cells of the tissue. It will be appreciated that due to the removal of all cellular components from the cell culture which comprises the ECM, the decellularized ECM cannot induce an immunological response when implanted in a recipient subject, e.g., a recipient to which the cells or cell components are xenogenic or allogenic.

Decellularization of the ECM can be done by various methods known in the art. For example, acellularization can be performed by combination of physical treatment—lyophilization, freeze and thaw cycling and DNase treatment, essentially as described in Ngangan A V and McDevitt T C [2009, Biomaterials 30:1143-1149 which is fully incorporated herein by reference in its entirety]; acellularization can be performed by Peracetic acid, Sodium dodecyl sulfate, Tritonx100 and DNase essentially as described in Nair R. et al. [2008, J. Biomater. Sci. Polymer Edn. 19: 801-819, which is fully incorporated herein by reference in its entirety]; acellularization can be performed by treatment with distilled water (e.g., Aqua dest) for 24 hours, 1% SDS for 24 hours, distilled water for 24 hours and 70% Ethanol for 24 hours, followed by washes with PBS, essentially as described in Tischer T. et al. [2007, Arch Orthop Trauma Surg. 127:735-741, which is fully incorporated herein by reference in its entirety]; acellularization can be performed by washes in hypertonic 1.1% NaCl-0.02% ethylenediaminetetraacetic acid (EDTA; Sigma, St. Louis, Mo.) for 2 hours and then in hypotonic 0.7% NaCl-0.02% EDTA for 2 hours, followed by two 24 hours cycles of enzymatic digestion using 0.05% trypsin (Sigma)-0.02% EDTA in PBS at pH 7.4 and at 37° C., supplemented with Pen-Strep and Fungizone, followed by wash(es) in detergent solution of 1% Triton-X-100 (polyethylene octylphenyl ether) and 0.1% ammonium hydroxide in PBS for four consecutive 48 hours cycles, and extensive washes in sterile saline, immersion in 70% ethanol overnight, and washes in sterile water, and lyophilization, essentially as described in Eitan Y. et al. [2010, Tissue engineering part C Methods. 16(4):671-83] which is fully incorporated herein by reference in its entirety]; acellularization can be performed by combination of physical and chemical treatments as—sonication, agitation, freezing and thawing, and then several detergent washes, essentially as described in Badylak S F et al. 2009 [ActaBiomaterialia, 5: 1-13, which is fully incorporated herein by reference in its entirety].

It should be noted that when the ECM is deposited on a substrate such as a scaffold made of an electrospun element, the decellularization process is performed such that the cellular components are removed while the ECM deposited on the scaffold is unharmed, and exhibits the same structure and mechanical properties as the ECM prior to the decellularization process.

Following is a non-limiting description of an acellularization protocol which can be used to decellularize the ECM of some embodiments of the invention.

The ECM is subject to treatment with a hypertonic solution (e.g., 50 mM Tris-HCl, 1 mM NaCl, 10 mM EDTA). The duration of incubation in the hypertonic solution can be from a few minutes, to hours and days. According to some embodiments of the invention, the ECM is treated with the hypertonic solution during an overnight incubation with gentle agitation. The treatment is then followed by one or more washes in a neutral buffer such as PBS, each wash can be done for a few minutes up to several hours. The ECM is then treated by Triton X-100 (e.g., about 1% Triton X-100) for a time period which varies between few minutes to several hours. According to some embodiments of the invention, the ECM is treated with the Triton X-100 solution for 1-2 hours at room temperature, with gentle agitation. Following treatment with Triton, the ECM can be washed with PBS, e.g., 2 washes in PBS, each wash for 5 minutes, following which the ECM is subject to DNAase treatment (using e.g., DNAse 1, at a concentration of 1 mg/ml for 1 hour at 37° C.).

For therapeutic applications, the ECM is generated and isolated (via acellularization) under sterile conditions (i.e., free of living organisms such as bacteria and yeast). In addition, the ECM can be subject to lyophilization under sterile conditions, and optionally can be subject to sterilization using ultra violet (UV) radiation, plasma treatment or both. Thus, the isolated ECM of some embodiments of the invention has a medical grade purity (i.e., safe for administration), and in some embodiments of the invention even an implant grade purity (i.e., safe for implantation).

The isolated ECM of some embodiments of the invention can be kept as an “off the shelf” product for a long period of time, which is practically eternal.

Thus, according to some embodiments of the invention, there is provided an isolated extracellular matrix produced according to the method of some embodiments of the invention.

According to some embodiments of the invention, the isolated ECM forms part of a device (e.g., scaffold such as an electrospun element).

According to an aspect of some embodiments of the invention, there is provided a hybrid device comprising an electrospun element and the isolated extracellular matrix of some embodiments of the invention. According to some embodiments of the invention, the ECM is deposited on the electrospun element and covers internal layers thereof (e.g., all layers of the electrospun element).

According to some embodiments of the invention, the hybrid device further comprising a supportive mesh, e.g., a synthetic mesh or net.

The supportive mesh of some embodiments of the invention may generally serve to provide strength and structural integrity to the biological tissue during its use in medical applications, thus serving as a reinforcement material. The reinforcement material may typically support the biological tissue and the surrounding tissue in general during wound repair and tissue closure.

According to some embodiments of the invention, the supportive mesh comprises a non-biodegradable material.

As used herein the phrase “non-biodegradable material” refers to a substance (e.g., metal, polymer) which is essentially stable i.e., non-degradable in the physiological environment of a subject (e.g., within a human body, e.g., within tissues or body fluids of the subject).

According to a specific embodiment, the material maintains at least about 90%, e.g., about 91%, about 92%, about 93%, about 94%, about 95%, about 96%, about 97%, about 98%, about 99%, 100% of its structure, function and dimension over a period of several years (e.g., at least 1-2 years) or over a life time in the body or tissue.

According to some embodiments of the invention, the non-biodegradable material is non-absorbable by the subject’s body.

According to some embodiments of the invention, the supportive mesh is biocompatible.

Selection of the supportive mesh may take into consideration the pore size, strength, permeability and flexibility of the material, as well as the structure and function of the surrounding tissue. For example, for use in applications involving load-bearing tissue, the supportive mesh may provide the appropriate tensile strength and flexibility to support the biological material and surrounding tissue during the formation of new tissue sufficient to support surrounding tissue. One of ordinary skill in the art can recognize the desired characteristics of the supportive mesh in selecting the optimal material.

The supportive mesh may comprise a material selected from the group consisting of polypropylene mesh such as Prolene™ (Ethicon Inc., Somerville, N.J.) and Marlex™ (C. R. Bard Inc.); polyester such as Dacron™ and Mersilene™ (Ethicon Inc., Somerville, N.J.); silicone, polyethylene, polyamide, titanium, stainless steel, polymethylmethacrylate, nylon, silk, cotton; polyglactic acid such as Vicryl™ mesh (Ethicon Inc., Somerville, N.J.), polyglycolic acid such as Dexon™ mesh; poliglecaprone, polydioxone and expanded polytetrafluoroethylene such as DualMesh™, Mycromesh™, or other expanded PTFE (W. L. Gore and Associates); PDS®, Vicryl®, or Monocryl®. In some embodiments, the supportive mesh may be multifilament polyester strands or monofilament polyester strands.

Supportive meshes can be purchased from any commercial source and manipulated into the desired shape or form using techniques known in the art. For example, in forming the shape of a mesh, the supportive mesh can be an over- and under-weave that is heat tacked at each junction point.

In some embodiments of the invention, the supportive mesh may undergo a crosslinking treatment to alter the mechanical properties of the material. For example, the supportive mesh may undergo crosslinking treatment to increase the strength of the material for medical applications in load-bearing tissue.

The supportive mesh may be of any shape or size according to its application as a support to the biological material in medical applications. Selection of the appropriate shape or size of the supportive mesh is routine for one of ordinary skill in the art. For example, the supportive mesh may be in the form of fibers organized as a mesh or lattice. In some embodiments, the mesh may be comprised of a web, wherein the web is defined by a plurality of spaced apertures. The mesh or lattice can have various designs such as polygons (triangles, rectangles, etc.), circles, ovals, spirals, or any combination thereof. The spaces between the fibers of the mesh can vary according to the size of the mesh and the medical application (e.g., for implantation in a load-bearing tissue), but are preferably between about 0.1 cm and about 2.0 cm.

According to some embodiments of the invention, the supportive mesh may be treated with an anti-infective agent. Non-limiting examples of anti-infective agents include, but are not limited to, anti-inflammatory agents, analgesic agents, local anesthetic agents, antispasmodic agents, or combinations thereof.

The addition of suitable anti-infective compounds to the surface of the mesh on the strands and junction points attack may inhibit the growth and proliferation of bacteria on and/or near the implant.

According to some embodiments of the invention, the supportive mesh may be treated with a protease inhibitor in order to alter its degradation rate. Non-limiting examples of protease inhibitors which can be used along with the invention include, but are not limited to, Aminoethylbenzenesulfonyl fluoride HCL, Aprotinin, Protease Inhibitor E-64, Leupeptin, Hemisulfate, EDTA, Disodium (0.025-0.10 um) or trypsin-like proteases, Pepstatin A (Aspartic Proteases), Mannistat (MMP2), or any combination thereof.

The above described treatments may be applied by methods known in the art, including, but not limited to, bathing, injecting, transfecting, bonding, coating, adding genetically modified cells and/or genetic material itself, or laminating.

The supportive mesh can be for example, the Prolift™ net available from to Ethicon, Sommerville, N.J., USA.

The isolated ECM or the hybrid device comprising same of some embodiments of the invention is characterized by bioactivity, biocompatibility and safety for surgical tissue reconstruction applications.

As used herein the phrase "bioactivity" refers to the ability to stimulate host cell restoration and tissue remodeling. A good bioactivity can be evaluated by the ability to induce host tissue integration and ability of biodegradation or absorption when replaced by the host tissue.

According to some embodiments of the invention, the biocompatibility of the isolated ECM or the hybrid device comprising same is such that following implantation in a subject the ECM or the device is not rejected or extruded, and/or does not cause long term inflammation, contamination, and/or disease transmission.

The isolated ECM or the hybrid device comprising same of some embodiments of the invention is homogenous, and uniform, with minimal batch to batch variations.

The isolated ECM or the hybrid device comprising same of some embodiments of the invention is highly available since can be generated by a robust technology using pluripotent stem cells.

As described above and further shown in the Examples section which follows, the present inventors used the decellularized ECM for implantation into mice and rats and showed that the isolated ECM is superior in its biocompatibility characteristics and the ability to induce tissue regeneration over commercially available supportive meshes (e.g., synthetic meshes) which were used as controls. Thus, as shown in FIGS. 10A-H, while the synthetic meshes were rejected by the implanted mice and rats and failed to close the incision, the nanofiber ECM implant, which was generated according to the method of some embodiments of the invention, was capable of successfully closing and healing the wound, while inducing a regenerated tissue.

Thus, according to an aspect of some embodiments of the invention, there is provided a method of inducing soft tissue regeneration or repair, the method is effected by implanting the isolated extracellular matrix of some embodiments of the invention or the hybrid device comprising same of some embodiments of the invention into a diseased or injured tissue of a subject, thereby inducing the soft tissue regeneration or repair.

According to an aspect of some embodiments of the invention, there is to provided a method of inducing soft tissue regeneration or repair. The method is effected by: (a) isolating an extracellular matrix according to the method of some embodiments of the invention, (b) decellularizing the extracellular matrix, and (c) implanting the extracellular matrix resultant of step (b) into a diseased or injured tissue of a subject, thereby inducing the soft tissue regeneration or repair.

According to some embodiments of the invention, the ECM is generated by culturing the MPCs of some embodiments of the invention on an electrospun element such that the extracellular matrix is deposited on the electrospun element.

According to some embodiments of the invention, the decellularization is performed on a device (e.g., a hybrid device) which comprises the electrospun element and the ECM deposited thereon (forming e.g., an acellular hybrid device).

As used herein the phrase "soft tissue" refers to a tissue that connects, supports, or surrounds other structures and organs of the body, not being a mineralized tissue as bone or tooth. Examples of soft tissues include, but are not limited to tendons, ligaments, fascia, skin, fibrous tissues, fat, synovial membranes (connective tissue), muscles, nerves and blood vessels.

As used herein the phrase "inducing soft tissue regeneration or repair" refers to initiating and/or improving the rate, degree and/or quality of a biological process of tissue regeneration or repair (including reconstruction of tissue).

According to some embodiments of the invention, the hybrid device ECM is used to reconstruct a tissue, by providing a mechanical strength while avoiding rejection by the recipient subject.

In cases of reconstruction surgeries, the repair of tissue can be evaluated by degree of compatibility of the graft by the host tissue, the generation of fibrous capsule around the foreign implant and the presence or absence of rejection of the implant.

As used herein the phrase "improving a biological process of tissue regeneration or repair" refers to improving the rate, degree and/or quality of a biological process of tissue regeneration or repair of tissue regeneration by at least about 2%, at least about 3%, at least about 4%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, e.g., 100%, at least about 2 times, at least about 3-10 times, at least about 20, 30, 40, 50, 60-100, 200, 300, 400, 500-1000 times as compared to a tissue which is not being treated by the isolated ECM or the hybrid device comprising same of some embodiments of the invention, or as compared to a tissue treated under the same (e.g., identical) conditions by implanting a supportive mesh (e.g., a synthetic mesh) which is devoid of extracellular matrix.

Methods of implanting grafts such as the isolated ECM or the hybrid device comprising same of some embodiments the invention into a subject are known in the art. For example, the isolated ECM or the hybrid device can be implanted subcutaneously, intradermally, into any body cavity (e.g., abdomen), into a wounded tissue, into an incision, and/or injected as a filler and as such can be used in many reconstructive surgeries in order to treat a subject in need of soft tissue regeneration or repair.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "subject" includes mammals, preferably human beings at any age which suffer from the pathology.

Following is a non-limiting list of pathologies which can be treated by implanting the isolated ECM of some embodiments of the invention: abdominal ventral hernia, pelvic floor defect (PFD), pelvic organ prolapse, stress urinary incontinence (a common disorder among women), and other pathologies which require replacement or reconstruction of various tissues.

Following is a non-limiting list of uses of the isolated ECM or the device comprising same of some embodiments of the invention: surgical products such as vascular and arterial graft, valve and aorta replacement, lower urinary tract reconstruction, skin substitute or reconstruction, use as myocardial patch and heart valve substitute, venous graft reconstruction, various orthopedic applications as tendon and ligaments replacement, tendon and ligament reconstruction, use as a drug release device, use as a dermal filler(s), probably as a gel generated from the acellular hybrid device, use as a biosynthetic prosthesis for the repair of ventral abdominal hernia and pelvic organ prolapse, use of the hybrid device for coating an available synthetic mesh (such a product can restore the physical properties of the prosthesis and the mechanical support to the defected anatomical site, triggering minimal adverse events), slings for the repair of stress urinary incontinence, use as dermal filers, e.g., as a hydrogel generated from the acellular NFL-ECM device (Badylak S F. 2004; Xenogeneic extracellular matrix as a scaffold for tissue reconstruction. Trans Immunol. 12: 367-377), or the ECM alone dissolve in a hydrogel.

The most common treatment for stress urinary incontinence is the use of suburethral synthetic slings, which demonstrate a relatively high rate of extrusion of the repair material and infection at the surgery site. The hybrid device of some embodiments of the invention can reduce these side effects.

According to an aspect of some embodiments of the invention, there is provided a hydrogel comprising the isolated ECM of some embodiments of the invention and/or the hybrid device of the some embodiments of the invention.

As used herein the term "hydrogel" refers to any material with molecular net structure in which water constitutes more than 50%. For example, a hydrogel can include the isolated ECM of some embodiments of the invention and/or the hybrid device of the some embodiments of the invention with a water constitute of at least 70%.

Non-limiting examples of polymers which can be used to generate the hybrid device-containing hydrogel include Collagen, PEG, PEG-DMA, and Alginate.

The hydrogel can be prepared from dextrandialdehyde with or without crosslinking with gelatin essentially as described in Schacht E et al. 1997 (Reactive and functional polymers 33:109-116) and/or Draye J P et al. 1998 (Biomaterials 19: 1677-1687), each of which is fully incorporated herein by reference in its entirety. The isolated ECM or the hybrid device comprising same undergoes decellularization and lyophilization and the dry acellular material (ECM or hybrid device comprising same) is dissolved in the hydrogel for in vivo injection of the mixture into the animal. The hydrogel which comprises the isolated ECM or the hybrid device comprising same can be assayed by subcutaneous injection, following which the injection area is analyzed by measuring its size during time post injection and by histology analysis of the injected animals.

The isolated ECM, the hybrid device and/or the hydrogel comprising same of some embodiments of the invention can be included in a kit/article of manufacture along with a packaging material and/or instructions for use in any of the above described methods, uses or applications.

The methods/uses described herein may be conducted batchwise.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Materials:

BHK Medium consists of a Glasgow Minimum Essential Medium (GMEM) with glutamine (GIBCO-Invitrogen, Paisley, UK) and supplemented with 10% lot specific fetal bovine serum (FBS) (Hyclone, Logan, Utah, USA), 1% penicillin (10,000 U/mL)-streptomycin (10 mg/mL) (Biological industries, Beit Haemek, Israel), 1% non-essential amino acids (NEAA) ×100, 1 mM sodium Pyruvate, 0.75 mM 2-mercaptoethanol (all from GIBCO-Invitrogen, Paisley, UK) and 100 μg/ml L-ascorbic acid 2-phosphate (Sigma, Rehovot, Israel).

EBs Medium—

80% F12 DMEM (an optimized Dulbeco's modified Eagle's medium for ES cells; Gibco-BRL, Gaithersburg, Md.), 20% fetal bovine serum (HyClone, Utah, USA), 1 mM glutamine (Gibco-BRL), 0.1 mM β-mercaptoethanol (Sigma, St. Louis, Mo.), and 1% nonessential amino acids stock (Gibco-BRL).

Derivation of Mesenchymal Progenitor Cells (MPCs) from hESCs and iPSCs Via the Formation of Embryoid Bodies (EBs)— hESCs or hiPSCs were cultured routinely. Embryoid bodies (EBs) differentiation was performed as previously described (Itskovitz-Eldor et al. 2000, Molecular Medicine 6: 88-95). For EB's dissociation, the EBs, which were generated in 10-cm tissue culture plate, were collected in a 50 ml tube, centrifuged for 3 minutes at 800 rounds per minute (rpm), washed with 5 ml PBS and centrifuged again. PBS was removed and 0.5 ml collagenase B (1 mg/ml)+Deoxyribonuclease I (final concentration 2 mg/ml) and incubated for 20 minutes at 37° C., during which the cells were mixed periodically. To stop Collagenase reaction, EBs medium (which includes serum) was added and the cells were centrifuged for 10 minutes at 1200 rpm. Cells (which were in aggregates containing about 10-30 cells/aggregate) were resuspended with EBs medium overnight. Then the medium was switched to BHK medium for further culturing of about 2-3 days. After this period the cells were recollected and dissociated by 0.1% Trypsin for 5-10 minutes at 37° C. Single cells suspension was filtered through Mesh such that only single cells (and not cell clusters) were isolated and further centrifuged. Cells were resuspended with 2 ml BHK medium and counted using Triphan-blue. Cells were seeded at concentration of $5\times10^5$ cells/$cm^2$ and cultured with BHK medium, the cultured cells are considered MPCs at passage 2-3 when they show homogenous morphology of mesenchymal cells. MPCs were routinely passages every 3-4 days up to passages 12-15.

Generation of Extracellular Matrix (ECM) from MPCs—

For ECM generation, MPCs were cultured for 3-4 weeks in the presence of BHK medium, with no subsequent passaging, such that high density cell cultures are cultured for a long time.

Adipose Derived (AD) MSC Isolation—

AD MSCs were Obtained from Raw human abdomen or thigh lipoaspirates. Lipoaspirates were washed extensively with sterile phosphate-buffer saline (PBS) to remove contaminating debris. Washed aspirates were treated with 1% collagenase type I (Sigma, Rehovot, Israel) in PBS for 1 hour at 37° C. with agitation. The collagenase was inactivated with an equal volume of DMEM/10% FBS/1 mM Glutamine/1% PenStrep/0.2 mg/ml Kanamycin and then was centrifuged for 10 minutes at 2000 rpm. The cellular pellet was resuspended in 160 mM Ammonium Chloride, incubated in room temperature for 10 minutes to remove red blood cells, neutralized with an equal volume of the BHK medium and filtered through a 100 mm mesh filter to remove large fat tissue debris. The filtrate was centrifuged as detailed above and plated onto conventional tissue culture flasks in BHK medium.

RT-PCR—

Total RNA was isolated using Trizol (Invitrogen, UK), according to the manufacturer's instructions, and cDNA was obtained by reverse transcribing 1 μg (microgram) of total RNA with 200 units of M-MLV Reverse Transcriptase (Promega, USA), using random primers (Promega, USA). PCR conditions were optimized for each set of primers and the number of PCR cycles was confirmed to be in the linear range of amplification. The amplified products were separated on a 2% agarose gel, stained with ethidium bromide and visualized under a UV light. Primer sequences, annealing temperatures and cycle numbers used for PCR reaction are listed at Table 1, hereinbelow.

TABLE 1

RT-PCR primers and conditions

| Gene (GenBank Accession No.; SEQ ID NO:) | Sequence (SEQ ID NO:) | Annealing Temp. | Num. of Cycles | Fragment Size (bp) |
|---|---|---|---|---|
| GAPDH (NM_002046.3) (SEQ ID NO: 37) | F: AGCCACATCGCTCAGACACC (SEQ ID NO: 1) R: GTACTCAGCGGCCAGCATCG (SEQ ID NO: 2) | 60° C. | 30 | 302 |
| Osteonectin (NM_003118; SEQ ID NO: 38) | F: GCAGCAATGACAACAAGACC (SEQ ID NO: 3) R: CTTCTCATTCTCATGGATCTTC (SEQ ID NO: 4) | 58° C. | 35 | 277 |
| Collagen 1 (NM_000089; SEQ ID NO: 39) | F: GCACACAATGGATTGCAAGG (SEQ ID NO: 5) R: TAACCACTGCTCCACTCTGG (SEQ ID NO: 6) | 64° C. | 35 | 476 |
| Collagen 3 (NM_000090; SEQ ID NO: 40) | F: CCTCCAACTGCTCCTACTCG (SEQ ID NO: 7) R: CGGGTCTACCTGATTCTCCA (SEQ ID NO: 8) | 60° C. | 35 | 439 |
| Scleraxis (NM_001008271; (SEQ ID NO: 41) | F: TGCAAGCTTCCCTTTTCAGT (SEQ ID NO: 9) R: CTGCACAGCCGAAATTGTAA (SEQ ID NO: 10) | 60° C. | 40 | 455 |
| Tenascin C (NM_002160; SEQ ID NO: 42) | F: CGTGGAGTACCTTGTCAGCA (SEQ ID NO: 11) R: AGGTAACCGGTGACTGATGC (SEQ ID NO: 12) | 60° C. | 35 | 438 |
| TNMD (NM_022144; SEQ ID NO: 43) | F: CCATGCTGGATGAGAGAGGT (SEQ ID NO: 13) R: CCACCAGTTACAAGGCATGA (SEQ ID NO: 14) | 58° C. | 35 | 158 |
| Elastin (NM_000501) (SEQ ID NO: 44) | F: GCTATGGACTGCCCTACACC (SEQ ID NO: 15) R: AGCTCCTGGGACACCAACTA (SEQ ID NO: 16) | 60° C. | 40 | 371 |
| Decorin (NM_001920; SEQ ID NO: 45) | F: TGAAGAACCTTCACGCATTG (SEQ ID NO: 17) R: GAGCCATTGTCAACAGCAGA (SEQ ID NO: 18) | 60° C. | 35 | 481 |
| BiGlycan (NM_001711; SEQ ID NO: 46) | F: TGCAGAACAACGACATCTCC (SEQ ID NO: 19) R: CCAGGTTCAAAGCCACTGTT (SEQ ID NO: 20) | 60° C. | 35 | 319 |
| Fibronectin (NM_212478; SEQ ID NO: 47) | F: GGAGTCAGCTGCCAAGAGAC (SEQ ID NO: 21) R: ACACACGTGCACCTCATCAT (SEQ ID NO: 22) | 60° C. | 35 | 482 |
| Sox 9 (NM_000346; SEQ ID NO: 48) | F: ATCTGAAGAAGGAGAGCGAG (SEQ ID NO: 23) R: TCAGAAGTCTCCAGAGCTTG (SEQ ID NO: 24) | 58° C. | 35 | 264 |
| Aggrecan (NM_013227; SEQ ID NO: 49) | F: ATCCGAGACACCAACGAGAC (SEQ ID NO: 25) R: GGCTTCACCCTCACTGATGT (SEQ ID NO: 26) | 60° C. | 35 | 477 |
| COMP 2 (NM_000095; SEQ ID NO: 50) | F: CAGGACGACTTTGATGCAGA (SEQ ID NO: 27) R: AAGCTGGAGCTGTCCTGGTA (SEQ ID NO: 28) | 58° C. | 35 | 314 |
| PPARγ (NM_138712; SEQ ID NO: 51) | F: TCATGGCAATTGAATGTCGT (SEQ ID NO: 29) R: GGGGCTGATGTGTTTGAACT (SEQ ID NO: 30) | 60° C. | 35 | 491 |

TABLE 1-continued

| RT-PCR primers and conditions | | | | |
|---|---|---|---|---|
| Gene (GenBank Accession No.; SEQ ID NO:) | Sequence (SEQ ID NO:) | Annealing Temp. | Num. of Cycles | Fragment Size (bp) |
| LPL (NM_000237; SEQ ID NO: 52) | F: GTCCGTGGCTACCTGTCATT (SEQ ID NO: 31) R: GGACCCTCTGGTGAATGTGT (SEQ ID NO: 32) | 60° C. | 35 | 463 |
| Adiponectin (NM_001177800; (SEQ ID NO: 53) | F: CCATCTCCTCCTCACTTCCA (SEQ ID NO: 33) R: CGATGTCTCCCTTAGGACCA (SEQ ID NO: 34) | 60° C. | 35 | 307 |
| Leptin (NM_000230; SEQ ID NO: 54) | F: GGCTTTGGCCCTATCTTTTC (SEQ ID NO: 35) R: GCTCTTAGAGAAGGCCAGCA (SEQ ID NO: 36) | 60° C. | 35 | 297 |

Table 1

Histochemistry—

Paraffin embedded sections were de-paraffinized and stained with hematoxylin and eosin (H&E) for general histomorphology, and with Masson's Trichrome for the detection of matrix collagens.

Cytochemistry—

Cells were fixed with 4% paraformaldehyde in PBS and stained with 2% Alizarin Red (Sigma, Rehovot, Israel) in water for calcium phosphate deposits detection in osteogenic differentiation and with 0.3% Oil Red O (Sigma, Rehovot, Israel) for lipid vacuoles visualization in adipogenic differentiation.

Immunofluorescence—

Immunoassay was done using the Benchmark automated system of Ventana (Ventana Medical Systems, Inc., Arizona, USA), using the following antibodies (at 1:1000 dilutions): Actin (Dako), Fibronectin (DBS), Desmin (Neomarkers), Laminin (Dako), Collagen IV (Dako), and Vimentin (Dako).

Fluorescence-Activated Cell Sorting (FACS) Analysis—

The MPCs or MSCs were detached and dissociated into single cells using 0.1% Trypsin in 0.05% EDTA. The cells were fixed using 4% paraformaldehyde for 15 minutes and were monitored by flow cytofluorometry on a FACScan system using CellQuest software (BD Biosciences, San Jose, Calif., USA). The antibodies used are listed in Table 2 hereinbelow.

TABLE 2

| Antibodies used for FACS analysis | | |
|---|---|---|
| Antibody | Company | Cat No. |
| FITC-Mouse IgG1 Isotype control | eBioscience Inc. San Diego, CA, USA | 11-4714 |
| FITC-CD31 | eBioscience Inc. San Diego, CA, USA | 11-0319 |
| PE-CD29 | eBioscience Inc. San Diego, CA, USA | 12-0297 |
| PE-CD44 | eBioscience Inc. San Diego, CA, USA | 12-0441 |
| PE-CD105 | eBioscience Inc. San Diego, CA, USA | 12-1057 |
| PE CD73 | PharMingen, Becton Dickinson Bio Sciences, San Jose, CA, USA | 550257 |

TABLE 2-continued

| Antibodies used for FACS analysis | | |
|---|---|---|
| Antibody | Company | Cat No. |
| PE-CD45 | eBioscience Inc. San Diego, CA, USA | 12-0459 |
| PE-CD34 | DakoCytomation (Glostrup, Denmark) | M7165 |

Table 2.

Induction of Multi-Lineage Differentiation of MSCs and MPCs

Culture Media—

Cells were cultured in a BHK medium which is described hereinabove.

Osteogenic Differentiation—

$2\times10^5$ cells per well were seeded on a 6-well plate or $5\times10^4$ cells per well on a 24-well plate in BHK medium which was used as the control medium throughout the experiment. On the following day, the cells were induced to differentiate into osteoblasts by enriching BHK medium with 10 mM β-glycerophosphate and $10^{-7}$ M dexamethasone (both from Sigma, Rehovot, Israel). The cells were cultured with this osteogenic medium for 28-30 days, without culture passaging, during which the medium was changed twice a week.

Staining with Alizarine Red—

Following 28 days the cells were fixed and stained with Alizarin Red. Alizarin Red is used to identify calcium in tissue sections. Calcium forms an Alizarin Red S-calcium complex in a chelation process, and the end product is birefringent.

Adipogenic Differentiation—

$2\times10^5$ cells per well were seeded on a 6-well plate or $5\times10^4$ cells per well on a 24-well plate. On the following day, the cells were fed with "Basic medium" composed of (DMEM)/F-12 supplemented with 1% penicillin (10,000 U/mL)-streptomycin (10 mg/mL), 1 mM glutamine (all from biological industries, Beit Haemek, Israel) and 10% lot specific FBS (Hyclone, Logan, Utah, USA). For adipogenesis induction the "basic medium" was enriched with 10 μg/ml insulin, 0.5 mM 3-Isobutyl-1-methylxanthine (IBMX), $10^{-6}$ M dexamethasone and $100\times10^{-6}$ M indomethacin (all from Sigma, Rehovot, Israel). The cells were cultured with this adipogenic medium for 28-30 days, without culture passaging, during which the medium was changed twice a week.

Chondrogenic Differentiation—

$2\times10^5$ cells were centrifuged at 300 g for 5 minutes in 15 ml polypropylene falcon tubes to form a cell pellet. The cells were grown for 6 weeks in DMEM medium supplemented with $10^{-7}$ M dexamethasone 1% ITS (Insulin-Transferin-Selenium, Catalogue No. 41400-045, Gibco, Invitrogen, USA), 50 μg/ml L-ascorbic acid 1 mM sodium pyruvate 4 mM L-proline and 10 ng/ml TGFβ3. Medium was replaced twice a week without disturbing the cell mass. Cell sections were made after fixing the cell pellets with 4% PFA and embedding the cell pellets in low melting point agarose (1.5%). Hematoxylin and eosin (H&E) and Alcian blue stainings were conducted.

Production of Extracellular Matrix—

For ECM production the MPCs were cultured in culture plates or on nanofiber layers (as described below) in the presence of a BHK medium for 3-4 weeks at 37° C., without culture passaging, while changing the BHK medium with fresh BHK medium every 3-4 days. ECM was deposited by the cells to the culture plates or the NFLs.

Nanofiber Layer (NFL) Fabrication and Cell Seeding—

Two types of fiber scaffolds were fabricated: (i) fiber scaffold composed of polycaprolactone (PCL) and (ii) fiber scaffold composed of 7% PCL and 93% poly(lactic-co-glycolic acid) (PLGA).

Preparation of Polymer Solutions—

The polymer solutions composition is described in Table 3, herein below. All polymers were purchased from Sigma-Aldrich.

TABLE 3

NFL polymer solutions composition

| Scaffold type | Polymer solution |
|---|---|
| PCL | 9 wt. % PCL 80K dissolved in a mixture of chloroform and dimethylformamide (DMF), 9:1 weight/weight (w/w) |
| PLGA | 1.4 wt. % PCL 80K + 9.3 wt. % PLGA 85-15 + 9.3 wt. % PLGA 50-50 dissolved in a mixture of chloroform and DMF, 8:2 (w/w) |

Table 3.
"wt. %" = weight percent, i.e., gram per 100 ml solution;
"w/w" = weight per weight ratio.

Electrospinning Set Up—

NFLs were fabricated using an electrospinning process as described in Srouji S. et al. 3-D nanofibrous electrospun multilayered construct is an alternative ECM mimicking scaffold. 2008. Mater Med 19:1249-1255, which is fully incorporated herein by reference in its entirety). All experiments were conducted at room temperature (~25° C.) and a relative humidity of about 50%. The spinning parameters were as follow: the electrostatic field used was approximately 0.7 kV/cm and the distance between the spinneret (metal pipette needle) and aluminum collector plate was 13 cm. The flow rate of the solutions was 3 ml/hour (controlled by a syringe pump). The fibers were collected on microscope cover glasses (diameter 18 mm) that were placed on top of a slowly rotating plate collector.

Seeding of NFL with Cells—

For cell seeding the NFLs were sterilized using either Gas-treatment with ethylene oxide or plasma treatment for 1-2 seconds and then UV treatment for 6-12 hour. The NFLs were incubated for overnight at BHK medium to verify their sterilization.

$2\times10^5$ MPCs were seeded on the NFL. The size of the NFL used was 18 mm in diameter (the coverslip size), and width of 30-100 μm. The NFLs were incubated in a 12 wells plate supplemented with 1-2 ml BHK medium. Cells were cultured for 2-4 weeks and medium was replaced twice a week. Before acellularization treatment MPCs-seeded NFLs were stained using a LIVE/DEAD® Cell Viability Assays (Molecular Probes) according to the manufacturer instructions for live cells staining.

Acellularization Protocol—

Following 3-4 weeks of MPCs culturing on NFL, the hybrid construct was decellularized using the following method: NFL-ECM device was treated with Hypertonic solution (50 mM Tris-Hcl, 1 mM NaCl, 10 mM EDTA) for overnight with gentle agitation. The treatment was followed by PBS wash and then treatment by 1% Triton X-100 for 1-2 hours at room temperature, with gentle agitation, followed by 2×PBS wash, and then treatment with 1 mg/ml DNase1 for 1 hour at 37° C.

Scanning Electron Microscopy (SEM)—

NFL-ECM construct was washed by PBS and then treated with 3% Glutaraldehyde, at least for 30 minutes (which by this time the sample can be sealed tightly and kept in 4° C.). The NFL-ECM construct was dehydrated by the following washes: 25% ethanol for 10 minutes, 50% ethanol for 10 minutes, 70-75% ethanol for 10 minutes, 90-95% ethanol for 10 minutes, 100% ethanol for 10 minutes. The 100% ethanol was then drained and allowed to evaporate in a chemical hood at room temperature.

Preparation of Samples for SEM—

Sample (5×5 mm) were attached to a SEM stud with double sided carbon tape. The samples were coated with a layer of gold for 15 seconds in an Emitech SC7620 sputter coater, following which the gold coated samples were imaged by SEM, model FEI Phenom.

Animal Implant Model—

SCID beige mice (4-weeks-old, 30 gram each) and Sprague-Dawley rats (4 months old, 300 gram each) were used in the experiment. Animals were provided with food and water ad libitum. The light cycle and the room temperature were automatically controlled. Before the experiments, animals were housed in these conditions for 3-4 days to become acclimatized. Animal care was in accordance with the guidelines of the Committee for the Supervision of Animal Experiments, Technion, Israel Institute of Technology Implants containing either synthetic mesh [Prolift™ (Ethicon, Sommerville, N.J., USA], NFL alone or NFL-ECM were implanted subcutaneously on the back of the animals (1 construct per animal) under general anesthesia (Ketamine 100 mg/mL, xylazine 1:1). Upon termination of the experiment (additional 8 week) the implants were carefully removed from adjacent tissues and examined by histology analysis, as described.

Example 1

Derivation of Mesenchymal Progenitor Cells (MSCs) from Pluripotent Stem Cells The present inventors have uncovered a novel method of generating mesenchymal progenitor cells from pluripotent stem cells (hESCs or hiPSCs). The major method steps include:

(1) enzymatic dissociation (e.g., using collagenase B) of EBs (e.g., 10-days old) into small aggregates;

(2) culturing of the cell aggregates as adherent cells to a tissue culture plate (devoid of gelatin or any adhesive material) for 2-3 days with BHK medium which triggers mesenchymal differentiation of the cells;

(3) harvesting the cells and further dissociating them into a single cell suspension using. Trypsin. The cells are allowed again to attach the tissue culture plate surface and cultured with BHK medium.

This protocol is simple and reproducible and can be used for generating mesenchymal progenitor cells which can produce high amounts of ECM for regenerative medicine applications.

Experimental Results

Generation of HFKT-iPSCs—

Recently, a novel method for the derivation of human induced pluripotent stem cells (iPSCs) from human plucked hair follicle keratinocytes (HFKT cells) was described by Novak et al., 2010 [Cell Reprogram. 2010, 12(6): 665-78)] using a single polycistronic STEMCCA lentiviral vector harboring the four reprogramming factors: Oct4, Sox2, c-Myc and Klf4. These iPSCs were further treated with Cre-recombinase for the excision of the lentiviral vector and the generation of transgene-free iPSCs (FIGS. 1A (i-iii)). Specific HFKT-iPSCs clones (labeled as: KTR and KTN, were derived from two different individuals) were subject to cre-recombinase transfection that efficiently excised the lentiviral DNA, leaving a transgene-free hiPSC clones (labeled as: Cre-KTN7.3 or Cre-KTR13.4).

Derivation of MPCs from pluripotent stem cells (hESCs or HFKT-iPSCs)—

To induce differentiation, the cells were cultured in conditions where they begin to form aggregates of spontaneously differentiated embryoid bodies (EBs), which contain derivatives of all three germ layers: ectoderm, mesoderm and endoderm. 10 day-old EBs were enzymatically dissociated into small aggregates of 10-30 cells (e.g., about 20 cells) using Collagenase B and DNAse. The small aggregates were cultured with EBs medium overnight (ON) and then with BHK medium for 2-3 days until cells expanded by at least 2 folds. Then the cells were collected and further dissociated using Trypsin and mesh filtration into a single cell suspension (FIGS. 1A-D). The suspended cells were further cultured in BHK medium to attain typical MPCs formation.

Generation of MPCs from HFKT-iPSCs—

MPCs were generated from the non-excised KTN7 clone as well as from the excised clones Cre-KTN7.3 or Cre-KTR13.4. The iPSCs were spontaneously differentiated into embryoid bodies (EBs), and MPCs were generated as described above and schematically shown in FIGS. 1A-D. Interestingly, MPCs derived from excised HFKT-iPSCs clones could grow faster and attain organized and condense network morphology following 2 weeks culturing (FIG. 1G) while MPCs derived from hESCs (FIG. 1E) or non-excised iPSCs (FIG. 1F) show relatively disorganized and disordered morphology. All MPCs described were able to proliferate efficiently up to passage 12-15, and then to show reduced growth rate and senescence.

These results demonstrate the derivation of MPCs from pluripotent stem cells by the novel method of some embodiments of the invention. In addition, these results show that the use of a transgene-excised HFKT-iPSCs is advantageous over the use of non-excised HFKT-iPSCs or over human ESCs for derivation of MPCs and further ECM.

Example 2

The Mesenchymal Progenitor Cells Derived According to the Method of Some Embodiments of the Invention Express Typical Mesenchymal Cell Surface Markers Experimental Results Characterization of MPCs by FACS Analysis—

To characterize the newly derived MPCs the expression of typical mesenchymal cell surface markers was tested using Flow cytometry analyses and compared to that of mesenchymal stem cells derived from an adipose tissue, which is used as a gold-standard. The FACS analysis revealed that adipose-derived MSCs are positive for expression of CD29 (FIG. 2A, 94.98%), CD44 (FIG. 2B, 99.8%), CD105 (FIG. 2C, 98.56%), CD73 (FIG. 2D, 100%) and CD90 (FIG. 2E, 91.5%) and were almost completely negative for expression of CD34 (FIG. 2F, 1.27%) and CD45 (FIG. 2G, 0.84%). FIG. 2H shows that MPCs derived from excised HFKT-iPSCs clones (Cre-KTN7.3 or Cre-KTR13.4) were 90-100% positive for all tested MSCs markers (CD29, CD44, CD105, CD73 and CD90). MPCs derived from non-excised HFKT-iPSC clone (KTN7) and hESC (H9.2 cell line) show a reduced expression of CD105 marker (~80% are CD105+). KTN7-MPCs shows reduced expression also for CD73 and CD29 markers (~80% are CD73+/CD29+). The hematopoietic markers CD34 and CD45 were almost negative (less than 20% of positive cells) in the MPCs clones that were tested. These results demonstrate that the mesenchymal progenitor cells exhibit a similar expression patter to that of adipose derived mesenchymal stem cells.

Example 3

The Mesenchymal Progenitor Cells Derived According to the Method of Some Embodiments of the Invention Exhibit a Significantly Reduced Ability to Differentiate into an Adipogenic Lineage Experimental Results The MPCs of Some Embodiments of the Invention are Capable of Forming a mineralized matrix—

The mesenchymal progenitor cells isolated according to the method of some embodiments of the invention were cultured in an osteogenic medium for 28-30 days and at the end of the culturing period the cells were stain with Alizarin Red (which tests presence of a mineralized matrix). As shown by Alizarin Red (AZR) staining calcium deposits and bone nodule formation was visible in both hESC-derived MPCs and iPSc-derived MPCs (FIGS. 3A-D). Thus, all the lines of mesenchymal progenitor cells were capable of forming mineralization in the culture at day 30 of culturing in an osteogenic medium.

The MPCs of Some Embodiments of the Invention Exhibit Low or No Differentiation Capacity into an Adipogenic Lineage—

As shown in FIGS. 3E-H, while adipogenic differentiation was well established from adipose-derived MSCs by Oil-Red-O (O-R-O) staining (FIG. 3E), there were only traces of adipogenic differentiation in hESCs-MPCs (FIG. 3F) and absence of any fat drops in iPSC-MPCs derived from both excised and non-excised HFKT-iPSCs clones (FIGS. 3G and 3H). These results demonstrate that the MPCs generated by the method of some embodiments of the invention have a significantly reduced ability to differentiate into the adipogenic lineage, and suggest that these cells have a more limited differentiation potential as compared to mesenchymal stem cells isolated from adult tissues.

The MPCs of Some Embodiments of the Invention Exhibit a Reduced Adipogenic Potential as Compared to Adult Mesenchymal Stem Cells (e.g., AD5T) Under Identical Assay Conditions (e.g., RT-PCR)—

Further RT-PCR analyses of the cultured cells using various adipogenic markers revealed that while the PPARγ transcription factor, known to regulate the primary adipogenic differentiation phase, was expressed in all cells type cultured in adipogenic medium (FIG. 13A), the adipogenic markers expressed by adipose cells such as leptin (FIG. 13B), adiponectin (FIG. 13C), Adipocyte protein 2 (AP2) (FIG. 13D) and Lipoprotein lipase (LPL) (FIG. 13E) were mostly expressed by adult MSCs (AD5T), while a significantly less expression or absence of expression was shown with MPCs derived from hair-follicle derived iPSCs or from hESC. These data indicate that functional adipocytes were not derived from the pluripotent stem cells derived-MPCs following adipogenic differentiation, as was also shown by Oil-R-O staining (FIGS. 3E-H).

The MPCs of Some Embodiments of the Invention are Capable of Differentiation into a Chondrogenic Differentiation—

Chondrogenic differentiation was well observed in the excised HFKT-iPSCs clones by Alciane Blue (AB) staining (FIGS. 3K and 3L), but could less efficiently generated by the adipose derived MSCs (FIG. 31) and hESCs derived MPCs (FIG. 3J).

The MPCs of Some Embodiments of the Invention Exhibit Increased Differentiation Potential into the Osteogenic Lineage—

The differentiation potential of the mesenchymal progenitor cells (MPCs) generated according to some embodiments of the invention into the osteogenic lineage was tested in vitro by culturing the cells in an osteogenic medium and staining the cells contained in the culture plates with Alizarin-red. As shown in FIGS. 4A-J, bone differentiation is highly elevated in MPCs derived from the excised HFKT-iPSCs clones relative to MPCs derived from hESCs clones or from adipose MSCs.

These differentiation assays demonstrate that MPCs are different from adipose-derived MSCs, especially in their significantly reduced ability to differentiate into the adipogenic lineage, and increased expression of osteogenic markers (e.g., calcium deposits which is stained with Alizarin red) when induced into the osteogenic lineage.

Example 4

Characterization of MPCS-Derived Extracellular Matrix (ECM)

For ECM generation the MPCs were cultured for long period (3-4 weeks) at high density in BHK medium without culture passaging. The long culturing triggers their differentiation into more compact and organized cell layers composed mainly of various types of collagens and other structural proteins as actin, fibronectin, vimentin and laminin FIGS. 5A-L represent the expression of the ECM main proteins in long-term matrix formation obtained from 4 weeks cultured MPCs derived from either hESCs or HFKT-iPSCs in comparison with matrix obtained from adipose derived MSCs.

Collagens are the Main Proteins Expressed in the ECM Derived from the MPCs of Some Embodiments of the Invention—

Trichrome staining indicates that collagens are the main proteins expressed for all derived matrixes. The collagen to structure is particularly condensed and organized in matrix obtained from Cre-KTN7.3 MPCs (FIG. 5D), while cells to collagen ratio is relatively reduced at this matrix (FIG. 5L).

Specific structures of actin can be observed at Cre-KTN7.3 matrix as well (FIG. 5H), while only few cells were found to express actin in matrixes derived from either hESCs (FIG. 5F) or the non-excised KTN7 clone (FIG. 5G).

The ECM Generated by the MPCs of Some Embodiments of the Invention Include Vimentin, Fibronectin and Laminin—

As shown in FIGS. 5M-X, vimentin, fibronectin and laminin are positively expressed in all tested matrixes but their expression is increased within matrixes derived from either adipose MSCs (FIGS. 5M, 5Q and 5U) and Cre-KTN7.3 MPCs (FIGS. 5P, 5T and 5X). Overall, results show that most significant expression of ECM components could be detected at ECM generated by the excised HFKT-iPSCs clones [results are shown here for Cre-KTN7.3 clone, similar data were found for the other excised clone Cre-KTR13.4 (Data not shown)].

FIGS. 6A-H describe RT-PCR analysis of ECM markers. RT-PCR was done for total RNA samples ECM samples obtained from Adipose derived MSCs, hESCs derived MPCs, KTN7 derived MPCs, Cre-KTN7.3 derived MPCs, and Cre-KTR13.4 derived MPCs. Results show that the RNA levels of ECM proteins can be observed within the ECM matrices derived from various stem cells sources. However, while some ECM proteins show reduced RNA levels at matrices derived from hESCs or KTN7MPCs (such as fibronectin, decorin, tensacin C and elastin), their RNA levels are significantly increased at the ECM samples obtained from the excised HFKT-iPSCs clones Cre-KTN7.3 and Cre-KTR13.4.

Overall, ECM characterization by histology, immunostaining and RT-PCR assays indicates that ECM derived from excised HFKT-iPSCs clones is efficiently secreted as described for ECM matrix derived from adipose-MSCs and have higher expression of ECM proteins relative to other pluripotent sources as hESCs, non-excised HFKT-iPSCs and fibroblasts iPSCs (data not shown). These data suggest that excised HFKT-iPSCs-MPCs might be the best pluripotent source for generating ECM for tissue engineering applications.

It should be noted that iPSCs are a better source relative to adipose MSCs since adipose MSCs need to be harvested from the patients by invasive procedure, while HFKT-iPSCs are derived from plucked hair. Moreover, adipose MSCs are not pluripotent cells and they have reduced proliferation capacity in culture while iPSCs are pluripotent cells that have potentially unlimited capacity to proliferate in culture at their undifferentiated stage. Therefore excised HFKT-iPSCs can be used as unlimited, available and homogeneous ECM source.

Example 5

Generation of Hybrid NfL (Nanofibers Layer)—ECM Device

Tissue acellularization provides ECM free of cellular components that can be transplanted in mammals without inducing acute immune response and host rejection. The generation of high amount of acellular stem cells-derived ECM can be used as a shelf product for various surgical applications. However, many efforts to decellularize ECM, generated from either adipose-MSCs or pluripotent sources as hESCs or iPSCs-MPCs, resulted in a too weak matrix that cannot be transplanted using a surgical sutures. Therefore an acellular hybrid device containing nanofibers layer and stem cells-derived ECM was developed.

Experimental Results

The Mesenchymal Progenitor Cells of Some Embodiments of the Invention Efficiently Proliferate all Over the NFL—

Adipose MSCs or Cre-KTN7.3/Cre-KTR13.4—MPCs were seeded on electrospun biodegradable NFL, composed of FDA-approved poly caprolactone (PCL) and Poly lactic glycolic acid (PLGA). Cells were cultured on the NFL for 2-4 weeks in the presence of the BHK medium and were found to well proliferate and secrete ECM within the NFL. Following culturing period, the stem cell-derived-ECM-NFL construct was subject to an acellularization process and the cellular as well as the acellular hybrid devices were analyzed by vital cells staining, scanning electron microscopy (SEM) and histology staining. CFDA (Carboxyfluorescein diacetate) vital staining was used to demonstrate live cells. As shown in FIG. 7A, the cellular hybrid exhibits extensive growth of Cre-KTN7.3-MPCs seeded on PLGA NFL for only 2 weeks, with expansion of cells on the NFL and between the nanofibers. FIG. 7B demonstrates the efficient acellularization treatment which eliminates all live cells from the NFL-ECM device. FIGS. 7C-H show confocal microscopy analysis of both cellular and acellular NFL-ECM devices, indicating that cells were proliferating all over the NFL dimensions and not only on the NFL surface.

MPCs Produce ECM on, Below, and Between the Nano Fibers—

Figure 8F:
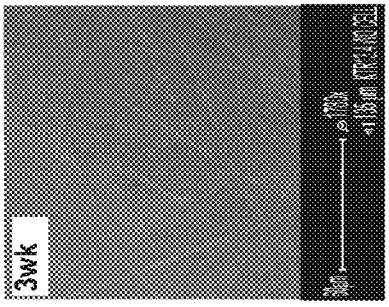

Scanning electron microscopy was used to analyze the ECM quality before and after acellularization treatment. FIGS. 8A-B demonstrate that ECM generated within the NFL is intact and is not damaged by the acellularization treatment. ECM generation and secretion within the NFL, by the excised HFKT-iPSCs derived MPCs (e.g., KTR13.4-MPCs), was analyzed at various culturing periods (FIG. 8C-F). Results show that the cells produce ECM on, below and between the nanofibers (typical morphology of collagen fibers are observed within the fibers following 1-2 culture weeks). The MPCs derived-ECM was found to completely cover the NFL surface following 3 weeks of cells culturing (FIG. 8F).

The Massive ECM Generated within the NFL and the ECM Proteins are not Harmed by the Acellularization Process—

Histology and immunostaining analysis were performed on the cellular and acellular NFL-ECM devices to further confirm the cells removal by acellularization treatment while ECM components remained intact. Hematoxilin and Eosin (HE) staining demonstrate the elimination of viable cells (e.g., FIGS. 9A and 9D), while Trichrom (TC) staining and fibronectin (FN) immunostaining indicate that massive ECM generated within the NFL and the ECM proteins are not harmed by the acellularization treatment (FIGS. 9B, 9C, 9E and 9F).

Example 6

In Vivo Transplantation of NFL-ECM Device

The present inventors have compared the efficiency of the NFL-ECM device of some embodiments of the invention with a surgical synthetic mesh, as follows.

The NFL-ECM hybrid device is a novel biodegradable biological mesh that might better stimulate host cells proliferation and tissue regeneration. This stem cell-derived ECM-NFL construct could be used as a biological support highly suitable to cure PFD disorders.

The in-vivo responses of SCID mice and rats to acellular NFL-ECM implants, relative to NFL alone, as well as to surgical synthetic mesh, were tested. The in-vivo experiment was done by subcutaneously transplantation of 2 identical implants in both neck sides of SCID Beige mice, as well as transplantation of similar implants within the rat two thighs. The present inventors compared the in vivo efficiency of commercially available surgical synthetic meshes (Prolift, Ethicon, N.J.) to two NFL devices: (i) PCL-NFL with no cells; and (ii) NFL-ECM, i.e., an MPC-derived NFL-ECM made from a PCL-NFL which was cultured with Cre-KTN7.3 MPCs for 4 weeks and which was further subjected to an acellularization process.

FIGS. 10A-D demonstrate the subcutaneous transplantation of synthetic mesh, and NFL alone (not shown) or NFL-ECM in SCID beige mice and Sprague-Dawley Rats. The implants are shown here before suturing the incisions. Then, the implants were well subcutaneously transplanted and covered by the animal skin. Nine weeks post transplantation the animals were sacrificed and analyzed. Interestingly, in both SCID mice and rats, 75% of synthetic meshes implants were completely discharged and could be clearly observed externally of the animal skin (FIGS. 10E and 10G). Moreover, the SCID mice transplanted with the synthetic mesh were sick and slim (e.g., the mouse seen in FIG. 10E) compared to the mice transplanted by either NFL (not shown) or NFL-ECM (e.g., the mouse seen in FIG. 10F), indicating a severe host response to the synthetic implants. In contrast, the NFL and the hybrid NFL-ECM implants were not rejected from the animal's body and the transplanted SCID mice exhibit a healthy apparent (FIG. 10F).

Rejection of the Synthetic Mesh Implant by the Recipient Animal—

Histology analyses of the synthetic mesh implants sections by hematoxilin & Eosin (HE) and trichrome (TC) staining revealed rigorous granuloma containing lymphocytes and neutrophils surrounding the synthetic fibers, observed as blue and white ellipsoids which are not stained by the histochemistry reagents (FIG. 11A-D).

Integration of the Hybrid NFL-ECM Implant within the Host Tissue of the Recipient Animal—

Figure 12F:

FIGS. 12A-F demonstrate the histology results of the rats and SCID mice following 9 weeks of transplantation with NFL alone (NFL only, FIGS. 12A and 12D) relative to the hybrid NFL-ECM implant in SCID mice (FIGS. 12B and 12E) and in rats (FIGS. 12C and 12F). Results indicate that NFL, composed of PCL material, significantly induced the animal immune response (FIGS. 12A and 12D). A granulomas, particularly containing macrophages, are observed within the NFL region, surrounding the PCL nanofibers that were not yet degraded following 9 weeks in vivo.

In contrast, the immune response against the hybrid NFL-ECM implant is reduced in both SCID mice and rats (FIGS. 12B, 12C, 12E and 12F). Although granuloma regions could be observed within the NFL-ECM hybrid, better integration with the host tissue was occurred, new blood vessels were emerged and strong collagen structures were generated around and within the hybrid device. The collagen structures indicating for desirable fibrosis formation that will ultimately replace the biodegradable implant and be used as the host reconstructed tissue.

These results demonstrate the contribution of the stem cells derived ECM, which is integrated on, below and between the NFL, in tissue reconstruction relative to NFL alone or to currently available synthetic meshes, and suggest an optional alternative for the displeasing surgical synthetic mesh.

Example 7

In Vivo Transplantation of PLGA NFL with ECM Generated by Mesenchymal Progenitor Cells According to Some Embodiments of the Invention NFLs, made of PLGA, were tested in vivo since PLGA has rapid degradation properties, and therefore might be less immunogenic as compared to the PCL-NFL.

Nanofiber layer (NFL) composed of either PLGA alone (FIGS. 14A, D and G), or of PLGA with live HFKT-iPSCs Cre KTN7.3 MPCs (before acellularization, FIGS. 14B, E and H) or of PLGA-ECM (made of HFKT-iPSCs Cre KTN7.3 MPCs cells after acellularization; FIGS. 14C, F and I) were used for transplantation in Sprague-Dawley Rats. The rats were sutured and well covered by the animal skin. Two identical implants were transplanted within the rat's two thighs. Eight weeks post transplantation the animals were sacrificed and implants were subjected to histology analysis on paraffin sections. As shown in FIGS. 14A and D, PLGA-NFL with no ECM retains its original structure and shows no integration with the host tissue, as well as a significant granuloma response, similarly to the findings observed using the PCL-NFL with no ECM (FIGS. 12A and D). A much better integration and a reduced host immune response was shown following implantation of PLGA-ECM. Following acellularization, the PLGA-ECM device shows better integration into the host tissue and high degradation rate (FIGS. 14C and F). Moreover, many new and large blood vessels were emerged at the implant site (FIG. 14F). These results demonstrate the good biocompatibility of the developed hybrid device composed of NFL-ECM following acellularization, particularly, when PLGA-NFL is used in combination with acellular ECM. This hybrid device suggests an optional construct for soft tissues regeneration.

Example 8

In Vivo Transplantation of Net-PCL NFL with ECM Generated By Mesenchymal Progenitor Cells According to Some Embodiments of the Invention Generation of a Composite Device Made of a Net, Electrospun Nanofibers and Extracellular Matrix—

The present inventors have generated a composite device made of a commercially available Net, Prolift net (Ethicon), which was further coated with electrospun nanofibers made of PCL, PLGA or a combination of PCL/PLGA nanofibers (FIG. 15B). The coated Net was used as a substrate for MPC culturing and ECM secretion during 4 weeks in the presence of BHK medium. The hybrid device was further subjected to acellularization process and then to lyophilization (FIG. 15C). SEM analysis of the hybrid NET-NFL-ECM device shows that the ECM fully covers the NFL (FIG. 15D), similarly to the results obtained with the NFL-ECM alone (FIGS. 8A-F), demonstrating that the net (mesh) below the NFL does not affect this process.

Superiority of NFL Over a Synthetic Net In Vivo—

Rats were transplanted with either a synthetic Net (Prolift Net) or with NFL PCL (both were devoid of ECM), and following 8 weeks the rats were sacrificed, the implant area was exposed and a sample from the implant surrounding tissue was subjected to histological analysis. As shown in FIG. 16A-D, while the Net implant was extruded out of the transplantation site to below the skin (FIG. 16C), the NFL implant was in the right tissue position, nicely coated with fibrotic tissue (FIG. 16D). Further histological analysis revealed that while the Net implant was located within the fat tissue and external to the muscle tissue, the NFL implant is well located along the muscle tissue (the original implantation site) (FIG. 17C).

In Vivo Effect of the Net-NFL-ECM Device of Some Embodiments of the Invention—

Hybrid devices were prepared using a Prolift™ (Ethicon, Sommerville, N.J., USA) Net coated with 30 μm PCL nanofibers, which was used as a substrate for culturing either adult adipose derived MSCs-AD5T or HFKT-iPSCs-Cre KTN7.3 MPCs, or without ECM. Following 4 weeks of culturing, the hybrid devices were subjected to an acellularization procedure and transplanted into the rat abdominal wall. Two duplicates were transplanted from each scaffold type. Eight weeks post transplantation the implants were removed along with the surrounding tissue, stained with H&E and photographed. As shown in FIGS. 18D-F, a significant generation of new blood vessels was observed in implants made of NET-NFL-ECM derived from HFKT-iPSCs-Cre KTN7.3 MPCs (FIG. 18F), as compared to implants made of NET-NFL-ECM derived from AD5T cells (FIG. 18E). In contrast, no blood vessels were shown in tissues implanted with the Net-NFL devoid of ECM (FIG. 18D).

Further histological analyses revealed that while the Net-NFL implant was located at the external fat tissue (FIG. 18H), the Net-NFL-ECM implants were located at their original site near the rat's muscle tissue (FIGS. 18K and N). In addition, while no significant immune response occurred around any of the implants (FIGS. 18I, L and O), a massive fibrous collagen structure was generated within the ECM-derived implants (FIGS. 18L and O). These results demonstrate that implants made of ECM derived from stem cells sources significantly affect tissue regeneration in vivo, while ECM derived from HFKT-iPSCs-Cre KTN7.3 MPCs also contributes to angiogenesis and integration of the implant within the rat tissues.

Analysis and Discussion

The Derivation of MPCs from HFKT-iPSCs and their Increased Capability to Secrete ECM and to Differentiate into Cartilage Lineage—

For the first time the present inventors generated MPCs from iPSCs. Moreover, the present inventors generated MPCs from various pluripotent sources such as H9.2-hESCs, human foreskin fibroblasts (HFF) derived iPSCs, HFKT-iPSCs and transgene-free HFKT-iPSCs.

The development of the NFL-ECM device: For the first time the present inventors developed a massive and stable device that can carry the stem cell-derived ECM components following acellularization. The acellularization procedure was found to mostly eliminate the live cells, leaving the matrix components intact.

Robust and Optimized "Off-the-Shelf" Device for Regenerative Medicine Applications:

The combined NFL-ECM acellular device is a stable and handy product that can be used as an "off-the-shelf" mesh with specific advantages of homogeneity, availability, bioactivity, biocompatibility and safety for surgical tissue reconstruction applications. To generate "off-the-shelf" biological scaffolds suitable to several surgical applications the present inventors developed a device including electrospun biodegradable nanofiber layer (NFL) composed of FDA-approved poly caprolactone to (PCL) and Poly lactic glycolic acid (PLGA), seeded with either adult MSCs or HFKT-Cre-iPSCs-MPCs. These mesenchymal progenitors extensively proliferate on the NFL for ~3 weeks at BHK medium, and efficiently secrete ECM components within the NFL. Following 3 weeks of culturing, the stem cell-derived-ECM-NFL construct underwent an acellularization treatment to eliminate live cells. This humanized acellular ECM-NFL device could serve as a robust clinical off-the-shelf product, providing the mechanical cues and the biological factors needed to support tissue reconstruction. In contrast to the currently used synthetic foreign mesh, this stem cell-derived NFL-ECM device triggers the regeneration of the native tissue and prevents undesired inflammation and further rejection. Human pluripotent stem cells are a practically unlimited, standardized and uniform human source for ECM generation. The matrix derived from these most early progenitors therefore displays excellent bioactivity, biocompatibility and safety qualities.

Synthetic scaffolds can perform superior mechanical characteristics, but they can never be integrated into the host tissue. Their biocompatibility is very poor and causes numerous long-term complications, such as severe infections, chronic immune response and potential toxic byproducts.

Several in-vivo assays were performed using acellular as well as cellular NFL-ECM devices, including subcutaneous transplantation in mice and rats.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of isolating an extracellular matrix, comprising:

(a) obtaining induced pluripotent stem cells (iPSCs) derived from plucked human hair follicle keratinocytes (HFKTs);

(b) generating embryoid bodies (EBs) from said iPSCs;

(c) generating single cells from adherent cells of said EBs, and (d) culturing said single cells in a culture medium which comprises ascorbic acid and does not comprise dexamethasone to thereby obtain a population of mesenchymal progenitor cells which comprises at least 70% CD105+ cells, wherein said mesenchymal progenitor cells exhibit at least 70% reduced differentiation potential into an adipogenic lineage as compared to differentiation of mesenchymal stem cells from an adult adipose source under identical assay conditions as analyzed after 28-30 days of culturing in a medium which comprises $10^{-6}$ M dexamethasone and indomethacin; and subsequently, (e) culturing said mesenchymal progenitor cells produced in step (d) under conditions which induce production of extracellular matrix from said mesenchymal progenitor cells, and subsequently, (f) isolating the extracellular matrix produced by said mesenchymal progenitor cells, thereby isolating the extracellular matrix.

2. The method of claim 1, further comprising decellularizing said extracellular matrix.

3. The method of claim 1, wherein said single cells from adherent cells of said EBs are obtained by:

(a) dissociating the EBs to cell aggregates, (b) culturing said cell aggregates on a low-adhesive surface so as to select a population of adherent cells, and (c) dissociating said adherent cells to single cells.

4. The method of claim 1, wherein said EBs are 8-14 day-old human EBs.

5. The method of claim 3, wherein each of said aggregates comprises about 10-30 cells.

6. The method of claim 3, wherein said dissociating said EBs into said aggregates is effected using Collagenase B.

7. The method of claim 3, wherein said adherent cells are expanded by at least 2 fold within 2-3 days of culturing in said culture medium.

8. The method of claim 1, wherein differentiation into an osteogenic lineage of said mesenchymal progenitor cells is increased by at least 50% as compared to differentiation of mesenchymal stem cells from an adult adipose source under identical assay conditions.

9. The method of claim 1, wherein said culturing in step (e) is performed on an electrospun element.

10. The method of claim 1, wherein at least 70% of said population of mesenchymal progenitor cells are CD105+/CD90+.

11. The method of claim 1, wherein at least 70% of said population of mesenchymal progenitor cells are characterized by a CD105+/CD90+/CD73+/CD44+/CD29+ signature.

12. The method of claim 1, wherein at least 70% of said population of mesenchymal progenitor cells are characterized by a CD105+/CD45−/CD34− signature.

13. The method of claim 1, wherein said mesenchymal progenitor cells maintain the ability to form extracellular matrix for at least 8 passages.

14. The method of claim 1, wherein said culturing in step (d) is performed for 1-15 passages.

15. The method of claim 1, wherein said iPSCs are lentiviral vector-free iPSCs.

* * * * *

SEQUENCE LISTING

```
<160> NUMBER OF SEQ ID NOS: 63

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1

agccacatcg ctcagacacc                                          20


<210> SEQ ID NO 2
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 2

gtactcagcg gccagcatcg                                          20


<210> SEQ ID NO 3
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 3

gcagcaatga caacaagacc                                          20


<210> SEQ ID NO 4
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 4

cttctcattc tcatggatct tc                                       22


<210> SEQ ID NO 5
<211> LENGTH: 20
```

<212> TYPE: DNA
<213> ORGANISM: Artificial sequence
<220> FEATURE:
<223> OTHER INFORMATION: Single strand DNA oligonucleotide

<400> SEQUENCE: 5
gcacacaatg gattgcaagg 20

<210> SEQ ID NO 6
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 6
taaccactgc tccactctgg 20

<210> SEQ ID NO 7
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 7
cctccaactg ctcctactcg 20

<210> SEQ ID NO 8
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 8
cgggtctacc tgattctcca 20

<210> SEQ ID NO 9
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 9
tgcaagcttc ccttttcagt 20

<210> SEQ ID NO 10
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 10
ctgcacagcc gaaattgtaa 20

<210> SEQ ID NO 11
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 11
cgtggagtac cttgtcagca 20

<210> SEQ ID NO 12
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 12
aggtaaccgg tgactgatgc 20

<210> SEQ ID NO 13
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 13
ccatgctgga tgagagaggt 20

<210> SEQ ID NO 14
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 14
ccaccagtta caaggcatga 20

<210> SEQ ID NO 15
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 15
gctatggact gccctacacc 20

<210> SEQ ID NO 16
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 16
agctcctggg acaccaacta 20

<210> SEQ ID NO 17
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 17
tgaagaacct tcacgcattg 20

<210> SEQ ID NO 18
<211> LENGTH: 20
<212> TYPE: DNA
<213> ORGANISM: Artificial sequence

```
<220> FEATURE:
<223> OTHER INFORMATION: Single strand DNA oligonucleotide

<400> SEQUENCE: 18

gagccattgt caacagcaga                                                20


<210> SEQ ID NO 19
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 19

tgcagaacaa cgacatctcc                                                20


<210> SEQ ID NO 20
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 20

ccaggttcaa agccactgtt                                                20


<210> SEQ ID NO 21
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 21

ggagtcagct gccaagagac                                                20


<210> SEQ ID NO 22
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 22

acacacgtgc acctcatcat                                                20


<210> SEQ ID NO 23
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 23

atctgaagaa ggagagcgag                                                20


<210> SEQ ID NO 24
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 24

tcagaagtct ccagagcttg                                                20
```

<210> SEQ ID NO 25
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 25
atccgagaca ccaacgagac 20

<210> SEQ ID NO 26
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 26
ggcttcaccc tcactgatgt 20

<210> SEQ ID NO 27
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 27
caggacgact ttgatgcaga 20

<210> SEQ ID NO 28
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 28
aagctggagc tgtcctggta 20

<210> SEQ ID NO 29
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 29
tcatggcaat tgaatgtcgt 20

<210> SEQ ID NO 30
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 30
ggggctgatg tgtttgaact 20

<210> SEQ ID NO 31
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 31
gtccgtggct acctgtcatt 20

<210> SEQ ID NO 32
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 32
ggaccctctg gtgaatgtgt 20

<210> SEQ ID NO 33
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 33
ccatctcctc ctcacttcca 20

<210> SEQ ID NO 34
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 34
cgatgtctcc cttaggacca 20

<210> SEQ ID NO 35
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 35
ggctttggcc ctatcttttc 20

<210> SEQ ID NO 36
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 36
gctcttagag aaggccagca 20

<210> SEQ ID NO 37
<211> LENGTH: 1310
<212> TYPE: DNA
<213> ORGANISM: Homo sapiens

<400> SEQUENCE: 37
aaattgagcc cgcagcctcc cgcttcgctc tctgctcctc ctgttcgaca gtcagccgca 60
tcttcttttg cgtcgccagc cgagccacat cgctcagaca ccatggggaa ggtgaaggtc 120
ggagtcaacg gatttggtcg tattgggcgc ctggtcacca gggctgcttt taactctggt 180

-continued

```
aaagtggata ttgttgccat caatgacccc ttcattgacc tcaactacat ggtttacatg    240

ttccaatatg attccaccca tggcaaattc catggcaccg tcaaggctga gaacgggaag    300

cttgtcatca atggaaatcc catcaccatc ttccaggagc gagatccctc caaaatcaag    360

tggggcgatg ctggcgctga gtacgtcgtg gagtccactg gcgtcttcac caccatggag    420

aaggctgggg ctcatttgca ggggggagcc aaaagggtca tcatctctgc cccctctgct    480

gatgccccca tgttcgtcat gggtgtgaac catgagaagt atgacaacag cctcaagatc    540

atcagcaatg cctcctgcac caccaactgc ttagcacccc tggccaaggt catccatgac    600

aactttggta tcgtggaagg actcatgacc acagtccatg ccatcactgc cacccagaag    660

actgtggatg gcccctccgg gaaactgtgg cgtgatggcc gcggggctct ccagaacatc    720

atccctgcct ctactggcgc tgccaaggct gtgggcaagg tcatccctga gctgaacggg    780

aagctcactg gcatggcctt ccgtgtcccc actgccaacg tgtcagtggt ggacctgacc    840

tgccgtctag aaaaacctgc caaatatgat gacatcaaga aggtggtgaa gcaggcgtcg    900

gagggccccc tcaagggcat cctgggctac actgagcacc aggtggtctc ctctgacttc    960

aacagcgaca cccactcctc cacctttgac gctggggctg gcattgccct caacgaccac   1020

tttgtcaagc tcatttcctg gtatgacaac gaatttggct acagcaacag ggtggtggac   1080

ctcatggccc acatggcctc caaggagtaa gacccctgga ccaccagccc cagcaagagc   1140

acaagaggaa gagagagacc ctcactgctg gggagtccct gccacactca gtcccccacc   1200

acactgaatc tcccctcctc acagttgcca tgtagacccc ttgaagaggg gaggggccta   1260

gggagccgca ccttgtcatg taccatcaat aaagtaccct gtgctcaacc              1310
```

<210> SEQ ID NO 38
<211> LENGTH: 3178
<212> TYPE: DNA
<213> ORGANISM: Homo sapiens

<400> SEQUENCE: 38

```
gttgcctgtc tctaaacccc tccacattcc cgcggtcctt cagactgccc ggagagcgcg     60

ctctgcctgc cgcctgcctg cctgccactg agggttccca gcaccatgag ggcctggatc    120

ttctttctcc tttgcctggc cgggagggcc ttggcagccc ctcagcaaga agccctgcct    180

gatgagacag aggtggtgga agaaactgtg gcagaggtga ctgaggtatc tgtgggagct    240

aatcctgtcc aggtggaagt aggagaattt gatgatggtg cagaggaaac cgaagaggag    300

gtggtggcgg aaaatccctg ccagaaccac cactgcaaac acggcaaggt gtgcgagctg    360

gatgagaaca acacccccat gtgcgtgtgc caggacccca ccagctgccc agcccccatt    420

ggcgagtttg agaaggtgtg cagcaatgac aacaagacct tcgactcttc ctgccacttc    480

tttgccacaa agtgcaccct ggagggcacc aagaagggcc acaagctcca cctggactac    540

atcgggcctt gcaaatacat ccccccttgc ctggactctg agctgaccga attccccctg    600

cgcatgcggg actggctcaa gaacgtcctg gtcaccctgt atgagaggga tgaggacaac    660

aaccttctga ctgagaagca gaagctgcgg gtgaagaaga tccatgagaa tgagaagcgc    720

ctggaggcag gagaccaccc cgtggagctg ctggcccggg acttcgagaa gaactataac    780

atgtacatct tccctgtaca ctggcagttc ggccagctgg accagcaccc cattgacggg    840

tacctctccc acaccgagct ggctccactg cgtgctcccc tcatccccat ggagcattgc    900

accacccgct tttcgagac ctgtgacctg gacaatgaca agtacatcgc cctggatgag    960

tgggccggct gcttcggcat caagcagaag gatatcgaca aggatcttgt gatctaaatc   1020
```

```
cactccttcc acagtaccgg attctctctt taaccctccc cttcgtgttt cccccaatgt   1080
ttaaaatgtt tggatggttt gttgttctgc ctggagacaa ggtgctaaca tagatttaag   1140
tgaatacatt aacggtgcta aaaatgaaaa ttctaaccca agacatgaca ttcttagctg   1200
taacttaact attaaggcct tttccacacg cattaatagt cccatttttc tcttgccatt   1260
tgtagctttg cccattgtct tattggcaca tgggtggaca cggatctgct gggctctgcc   1320
ttaaacacac attgcagctt caacttttct ctttagtgtt ctgtttgaaa ctaatactta   1380
ccgagtcaga ctttgtgttc atttcatttc agggtcttgg ctgcctgtgg gcttccccag   1440
gtggcctgga ggtgggcaaa gggaagtaac agacacacga tgttgtcaag gatggttttg   1500
ggactagagg ctcagtggtg ggagagatcc ctgcagaacc caccaaccag aacgtggttt   1560
gcctgaggct gtaactgaga gaaagattct ggggctgtgt tatgaaaata tagacattct   1620
cacataagcc cagttcatca ccatttcctc ctttaccttt cagtgcagtt tcttttcaca   1680
ttaggctgtt ggttcaaact tttgggagca cggactgtca gttctctggg aagtggtcag   1740
cgcatcctgc agggcttctc ctcctctgtc ttttggagaa ccagggctct tctcaggggc   1800
tctagggact gccaggctgt ttcagccagg aaggccaaaa tcaagagtga gatgtagaaa   1860
gttgtaaaat agaaaaagtg gagttggtga atcggttgtt ctttcctcac atttggatga   1920
ttgtcataag gtttttagca tgttcctcct tttcttcacc ctcccctttt ttcttctatt   1980
aatcaagaga aacttcaaag ttaatgggat ggtcggatct cacaggctga gaactcgttc   2040
acctccaagc atttcatgaa aaagctgctt cttattaatc atacaaactc tcaccatgat   2100
gtgaagagtt tcacaaatcc ttcaaaataa aaagtaatga cttagaaact gccttcctgg   2160
gtgatttgca tgtgtcttag tcttagtcac cttattatcc tgacacaaaa acacatgagc   2220
atacatgtct acacatgact acacaaatgc aaacctttgc aaacacatta tgcttttgca   2280
cacacacacc tgtacacaca caccggcatg tttatacaca gggagtgtat ggttcctgta   2340
agcactaagt tagctgtttt catttaatga cctgtggttt aaccctttttg atcactacca   2400
ccattatcag caccagactg agcagctata tccttttatt aatcatggtc attcattcat   2460
tcattcattc acaaaatatt tatgatgtat ttactctgca ccaggtccca tgccaagcac   2520
tggggacaca gttatggcaa agtagacaaa gcatttgttc atttggagct tagagtccag   2580
gaggaataca ttagataatg acacaatcaa atataaattg caagatgtca caggtgtgat   2640
gaagggagag taggagagac catgagtatg tgtaacagga ggacacagca ttattctagt   2700
gctgtactgt tccgtacggc agccactacc cacatgtaac tttttaagat ttaaatttaa   2760
attagttaac attcaaaacg cagctcccca atcacactag caacatttca agtgcttgag   2820
agccatgcat gattagtggt taccctattg aataggtcag aagtagaatc ttttcatcat   2880
cacagaaagt tctattggac agtgctcttc tagatcatca taagactaca gagcactttt   2940
caaagctcat gcatgttcat catgttagtg tcgtattttg agctggggtt ttgagactcc   3000
ccttagagat agagaaacag acccaagaaa tgtgctcaat tgcaatgggc cacataccta   3060
gatctccaga tgtcatttcc cctctcttat tttaagttat gttaagatta ctaaaacaat   3120
aaaagctcct aaaaaatcaa aaaaaaaaaa aaaaaaaaaa aaaaaaaaaa aaaaaaaa     3178
```

<210> SEQ ID NO 39
<211> LENGTH: 5411
<212> TYPE: DNA
<213> ORGANISM: Homo sapiens

<400> SEQUENCE: 39

```
gtgtcccata gtgtttccaa acttggaaag ggcgggggag ggcgggagga tgcggagggc     60
ggaggtatgc agacaacgag tcagagtttc cccttgaaag cctcaaaagt gtccacgtcc    120
tcaaaaagaa tggaaccaat ttaagaagcc agccccgtgg ccacgtccct tcccccattc    180
gctccctcct ctgcgccccc gcaggctcct cccagctgtg gctgcccggg cccccagccc    240
cagccctccc attggtggag gcccttttgg aggcacccta gggccaggga aacttttgcc    300
gtataaatag ggcagatccg ggctttatta ttttagcacc acggcagcag gaggtttcgg    360
ctaagttgga ggtactggcc acgactgcat gcccgcgccc gccaggtgat acctccgccg    420
gtgacccagg ggctctgcga cacaaggagt ctgcatgtct aagtgctaga catgctcagc    480
tttgtggata cgcggacttt gttgctgctt gcagtaacct tatgcctagc aacatgccaa    540
tctttacaag aggaaactgt aagaaagggc ccagccggag atagaggacc acgtggagaa    600
aggggtccac caggcccccc aggcagagat ggtgaagatg gtcccacagg ccctcctggt    660
ccacctggtc ctcctggccc ccctggtctc ggtgggaact ttgctgctca gtatgatgga    720
aaaggagttg gacttggccc tggaccaatg ggcttaatgg gacctagagg cccacctggt    780
gcagctggag ccccaggccc tcaaggtttc caaggacctg ctggtgagcc tggtgaacct    840
ggtcaaactg gtcctgcagg tgctcgtggt ccagctggcc ctcctggcaa ggctggtgaa    900
gatggtcacc ctggaaaacc cggacgacct ggtgagagag gagttgttgg accacagggt    960
gctcgtggtt tccctggaac tcctggactt cctggcttca aaggcattag ggacacaat    1020
ggtctggatg gattgaaggg acagcccggt gctcctggtg tgaagggtga acctggtgcc   1080
cctggtgaaa atggaactcc aggtcaaaca ggagcccgtg ggcttcctgg tgagagagga   1140
cgtgttggtg cccctggccc agctggtgcc cgtggcagtg atggaagtgt gggtcccgtg   1200
ggtcctgctg gtcccattgg gtctgctggc cctccaggct tcccaggtgc ccctggcccc   1260
aagggtgaaa ttggagctgt tggtaacgct ggtcctgctg gtcccgccgg tccccgtggt   1320
gaagtgggtc ttccaggcct ctccggcccc gttggacctc ctggtaatcc tggagcaaac   1380
ggccttactg gtgccaaggg tgctgctggc cttcccggcg ttgctggggc tcccggcctc   1440
cctggacccc gcggtattcc tggccctgtt ggtgctgccg gtgctactgg tgccagagga   1500
cttgttggtg agcctggtcc agctggctcc aaaggagaga gcggtaacaa gggtgagccc   1560
ggctctgctg ggccccaagg tcctcctggt cccagtggtg aagaaggaaa gagaggccct   1620
aatggggaag ctggatctgc cggccctcca ggacctcctg ggctgagagg tagtcctggt   1680
tctcgtggtc ttcctggagc tgatggcaga gctggcgtca tgggccctcc tggtagtcgt   1740
ggtgcaagtg gccctgctgg agtccgagga cctaatggag atgctggtcg ccctggggag   1800
cctggtctca tgggacccag aggtcttcct ggttcccctg gaaatatcgg ccccgctgga   1860
aaagaaggtc ctgtcggcct ccctggcatc gacggcaggc ctggcccaat tggcccagct   1920
ggagcaagag gagagcctgg caacattgga ttccctggac ccaaaggccc cactggtgat   1980
cctggcaaaa acggtgataa aggtcatgct ggtcttgctg gtgctcgggg tgctccaggt   2040
cctgatggaa acaatggtgc tcagggacct cctggaccac agggtgttca aggtggaaaa   2100
ggtgaacagg gtccccctgg tcctccaggc ttccagggtc tgcctggccc ctcaggtccc   2160
gctggtgaag ttggcaaacc aggagaaagg ggtctccatg gtgagtttgg tctccctggt   2220
cctgctggtc caagagggga acgcggtccc ccaggtgaga gtggtgctgc cggtcctact   2280
ggtcctattg gaagccgagg tccttctgga cccccagggc ctgatggaaa caagggtgaa   2340
```

-continued

```
cctggtgtgg ttggtgctgt gggcactgct ggtccatctg gtcctagtgg actcccagga   2400
gagaggggtg ctgctggcat acctggaggc aagggagaaa agggtgaacc tggtctcaga   2460
ggtgaaattg gtaaccctgg cagagatggt gctcgtggtg ctcctggtgc tgtaggtgcc   2520
cctggtcctg ctggagccac aggtgaccgg ggcgaagctg gggctgctgg tcctgctggt   2580
cctgctggtc ctcggggaag ccctggtgaa cgtggtgagg tcggtcctgc tggccccaat   2640
ggatttgctg gtcctgctgg tgctgctggt caacctggtg ctaaaggaga aagaggagcc   2700
aaagggccta agggtgaaaa cggtgttgtt ggtcccacag gccccgttgg agctgctggc   2760
ccagctggtc caaatggtcc ccccggtcct gctggaagtc gtggtgatgg aggcccccct   2820
ggtatgactg gtttccctgg tgctgctgga cggactggtc cccaggacc ctctggtatt   2880
tctggccctc ctggtccccc tggtcctgct gggaaagaag ggcttcgtgg tcctcgtggt   2940
gaccaaggtc cagttggccg aactggagaa gtaggtgcag ttggtccccc tggcttcgct   3000
ggtgagaagg gtccctctgg agaggctggt actgctggac ctcctggcac tccaggtcct   3060
cagggtcttc ttggtgctcc tggtattctg ggtctccctg gctcgagagg tgaacgtggt   3120
ctaccaggtg ttgctggtgc tgtgggtgaa cctggtcctc ttggcattgc cggccctcct   3180
ggggcccgtg gtcctcctgg tgctgtgggt agtcctggag tcaacggtgc tcctggtgaa   3240
gctggtcgtg atggcaaccc tgggaacgat ggtcccccag gtcgcgatgg tcaacccgga   3300
cacaagggag agcgcggtta ccctggcaat attggtcccg ttggtgctgc aggtgcacct   3360
ggtcctcatg gccccgtggg tcctgctggc aaacatggaa accgtggtga aactggtcct   3420
tctggtcctg ttggtcctgc tggtgctgtt ggcccaagag gtcctagtgg cccacaaggc   3480
attcgtggcg ataagggaga gcccggtgaa aaggggccca gaggtcttcc tggcttaaag   3540
ggacacaatg gattgcaagg tctgcctggt atcgctggtc accatggtga tcaaggtgct   3600
cctggctccg tgggtcctgc tggtcctagg ggccctgctg gtccttctgg ccctgctgga   3660
aaagatggtc gcactggaca tcctggtaca gttggacctg ctggcattcg aggccctcag   3720
ggtcaccaag gccctgctgg ccccccctggt cccccctggcc ctcctggacc tccaggtgta   3780
agcggtggtg gttatgactt tggttacgat ggagacttct acagggctga ccagcctcgc   3840
tcagcacctt ctctcagacc caaggactat gaagttgatg ctactctgaa gtctctcaac   3900
aaccagattg agacccttct tactcctgaa ggctctagaa agaacccagc tcgcacatgc   3960
cgtgacttga gactcagcca cccagagtgg agcagtggtt actactggat tgaccctaac   4020
caaggatgca ctatggatgc tatcaaagta tactgtgatt tctctactgg cgaaacctgt   4080
atccgggccc aacctgaaaa catcccagcc aagaactggt ataggagctc caaggacaag   4140
aaacacgtct ggctaggaga aactatcaat gctggcagcc agtttgaata taatgtagaa   4200
ggagtgactt ccaaggaaat ggctacccaa cttgccttca tgcgcctgct ggccaactat   4260
gcctctcaga acatcaccta ccactgcaag aacagcattg catacatgga tgaggagact   4320
ggcaacctga aaaaggctgt cattctacag ggctctaatg atgttgaact tgttgctgag   4380
ggcaacagca ggttcactta cactgttctt gtagatggct gctctaaaaa gacaaatgaa   4440
tggggaaaga caatcattga atacaaaaca aataagccat cacgcctgcc cttccttgat   4500
attgcacctt tggacatcgg tggtgctgac caggaattct ttgtggacat tggcccagtc   4560
tgtttcaaat aaatgaactc aatctaaatt aaaaaagaaa gaaatttgaa aaaactttct   4620
ctttgccatt tcttcttctt cttttttaac tgaaagctga atccttccat ttcttctgca   4680
```

catctacttg cttaaattgt gggcaaaaga gaaaaagaag gattgatcag agcattgtgc 4740
aatacagttt cattaactcc ttccccccgct cccccaaaaa tttgaatttt tttttcaaca 4800
ctcttacacc tgttatggaa aatgtcaacc tttgtaagaa aaccaaaata aaaattgaaa 4860
aataaaaacc ataaacattt gcaccacttg tggcttttga atatcttcca cagagggaag 4920
tttaaaaccc aaacttccaa aggtttaaac tacctcaaaa cactttccca tgagtgtgat 4980
ccacattgtt aggtgctgac ctagacagag atgaactgag gtccttgttt tgttttgttc 5040
ataatacaaa ggtgctaatt aatagtattt cagatacttg aagaatgttg atggtgctag 5100
aagaatttga gaagaaatac tcctgtattg agttgtatcg tgtggtgtat tttttaaaaa 5160
atttgattta gcattcatat tttccatctt attcccaatt aaaagtatgc agattatttg 5220
cccaaatctt cttcagattc agcatttgtt ctttgccagt ctcattttca tcttcttcca 5280
tggttccaca gaagctttgt ttcttgggca agcagaaaaa ttaaattgta cctattttgt 5340
atatgtgaga tgtttaaata aattgtgaaa aaaatgaaat aaagcatgtt tggttttcca 5400
aaagaacata t 5411

<210> SEQ ID NO 40
<211> LENGTH: 5490
<212> TYPE: DNA
<213> ORGANISM: Homo sapiens

<400> SEQUENCE: 40
ggctgagttt tatgacgggc ccggtgctga agggcaggga acaacttgat ggtgctactt 60
tgaactgctt ttcttttctc ctttttgcac aaagagtctc atgtctgata tttagacatg 120
atgagctttg tgcaaaaggg gagctggcta cttctcgctc tgcttcatcc cactattatt 180
ttggcacaac aggaagctgt tgaaggagga tgttcccatc ttggtcagtc ctatgcggat 240
agagatgtct ggaagccaga accatgccaa atatgtgtct gtgactcagg atccgttctc 300
tgcgatgaca taatatgtga cgatcaagaa ttagactgcc ccaacccaga aattccattt 360
ggagaatgtt gtgcagtttg cccacagcct ccaactgctc ctactcgccc tcctaatggt 420
caaggacctc aaggccccaa gggagatcca ggccctcctg gtattcctgg gagaaatggt 480
gaccctggta ttccaggaca accagggtcc cctggttctc ctggcccccc tggaatctgt 540
gaatcatgcc ctactggtcc tcagaactat tctccccagt atgattcata tgatgtcaag 600
tctggagtag cagtaggagg actcgcaggc tatcctggac cagctggccc cccaggccct 660
cccggtcccc ctggtacatc tggtcatcct ggttcccctg gatctccagg ataccaagga 720
ccccctggtg aacctgggca agctggtcct tcaggccctc caggacctcc tggtgctata 780
ggtccatctg gtcctgctgg aaaagatgga gaatcaggta gacccggacg acctggagag 840
cgaggattgc ctggacctcc aggtatcaaa ggtccagctg ggatacctgg attccctggt 900
atgaaaggac acagaggctt cgatggacga aatggagaaa agggtgaaac aggtgctcct 960
ggattaaagg gtgaaaatgg tcttccaggc gaaaatggag ctcctggacc catgggtcca 1020
agaggggctc ctggtgagcg aggacggcca ggacttcctg gggctgcagg tgctcggggt 1080
aatgacggtg ctcgaggcag tgatggtcaa ccaggccctc ctggtcctcc tggaactgcc 1140
ggattccctg gatcccctgg tgctaagggt gaagttggac ctgcagggtc tcctggttca 1200
aatggtgccc ctggacaaag aggagaacct ggacctcagg gacacgctgg tgctcaaggt 1260
cctcctggcc ctcctgggat taatggtagt cctggtggta aaggcgaaat gggtcccgct 1320
ggcattcctg gagctcctgg actgatggga gcccggggtc ctccaggacc agccggtgct 1380

-continued

```
aatggtgctc ctggactgcg aggtggtgca ggtgagcctg gtaagaatgg tgccaaagga   1440
gagcccggac cacgtggtga acgcggtgag gctggtattc caggtgttcc aggagctaaa   1500
ggcgaagatg gcaaggatgg atcacctgga gaacctggtg caaatgggct tccaggagct   1560
gcaggagaaa ggggtgcccc tgggttccga ggacctgctg gaccaaatgg catcccagga   1620
gaaaagggtc ctgctggaga gcgtggtgct ccaggccctg cagggcccag aggagctgct   1680
ggagaacctg gcagagatgg cgtccctgga ggtccaggaa tgaggggcat gcccggaagt   1740
ccaggaggac caggaagtga tgggaaacca gggcctcccg gaagtcaagg agaaagtggt   1800
cgaccaggtc ctcctgggcc atctggtccc cgaggtcagc ctggtgtcat gggcttcccc   1860
ggtcctaaag gaaatgatgg tgctcctggt aagaatggag aacgaggtgg ccctggagga   1920
cctggccctc agggtcctcc tggaaagaat ggtgaaactg gacctcaggg acccccaggg   1980
cctactgggc ctggtggtga caaaggagac acaggacccc ctggtccaca aggattacaa   2040
ggcttgcctg gtacaggtgg tcctccagga gaaaatggaa aacctgggga accaggtcca   2100
aagggtgatg ccggtgcacc tggagctcca ggaggcaagg gtgatgctgg tgcccctggt   2160
gaacgtggac ctcctggatt ggcaggggcc ccaggactta gaggtggagc tggtcccccct   2220
ggtcccgaag gaggaaaggg tgctgctggt cctcctgggc cacctggtgc tgctggtact   2280
cctggtctgc aaggaatgcc tggagaaaga ggaggtcttg gaagtcctgg tccaaagggt   2340
gacaagggtg aaccaggcgg tccaggtgct gatggtgtcc cagggaaaga tggcccaagg   2400
ggtcctactg gtcctattgg tcctcctggc ccagctggcc agcctggaga taagggtgaa   2460
ggtggtgccc ccggacttcc aggtatagct ggacctcgtg gtagccctgg tgagagaggt   2520
gaaactggcc ctccaggacc tgctggtttc cctggtgctc ctggacagaa tggtgaacct   2580
ggtggtaaag gagaaagagg ggctccgggt gagaaaggtg aaggaggccc tcctggagtt   2640
gcaggacccc ctggaggttc tggacctgct ggtcctcctg gtccccaagg tgtcaaaggt   2700
gaacgtggca gtcctggtgg acctggtgct gctggcttcc ctggtgctcg tggtcttcct   2760
ggtcctcctg gtagtaatgg taacccagga cccccaggtc ccagcggttc tccaggcaag   2820
gatgggcccc caggtcctgc gggtaacact ggtgctcctg gcagccctgg agtgtctgga   2880
ccaaaaggtg atgctggcca accaggagag aagggatcgc ctggtgccca gggcccacca   2940
ggagctccag gcccacttgg gattgctggg atcactggag cacggggtct tgcaggacca   3000
ccaggcatgc caggtcctag gggaagccct ggccctcagg gtgtcaaggg tgaaagtggg   3060
aaaccaggag ctaacggtct cagtggagaa cgtggtcccc ctggacccca gggtcttcct   3120
ggtctggctg gtacagctgg tgaacctgga agagatggaa accctggatc agatggtctt   3180
ccaggccgag atggatctcc tggtggcaag ggtgatcgtg gtgaaaatgg ctctcctggt   3240
gcccctggcg ctcctggtca tccaggccca cctggtcctg tcggtccagc tggaaagagt   3300
ggtgacagag gagaaagtgg ccctgctggc cctgctggtg ctcccggtcc tgctggttcc   3360
cgaggtgctc ctggtcctca aggcccacgt ggtgacaaag gtgaaacagg tgaacgtgga   3420
gctgctggca tcaaaggaca tcgaggattc cctggtaatc caggtgcccc aggttctcca   3480
ggccctgctg gtcagcaggg tgcaatcggc agtccaggac ctgcaggccc cagaggacct   3540
gttggaccca gtggacctcc tggcaaagat ggaaccagtg gacatccagg tcccattgga   3600
ccaccagggc ctcgaggtaa cagaggtgaa agaggatctg agggctcccc aggccaccca   3660
gggcaaccag gccctcctgg acctcctggt gcccctggtc cttgctgtgg tggtgttgga   3720
```

```
gccgctgcca ttgctgggat tggaggtgaa aaagctggcg gttttgcccc gtattatgga   3780
gatgaaccaa tggatttcaa aatcaacacc gatgagatta tgacttcact caagtctgtt   3840
aatggacaaa tagaaagcct cattagtcct gatggttctc gtaaaaaccc cgctagaaac   3900
tgcagagacc tgaaattctg ccatcctgaa ctcaagagtg gagaatactg ggttgaccct   3960
aaccaaggat gcaaattgga tgctatcaag gtattctgta atatggaaac tggggaaaca   4020
tgcataagtg ccaatccttt gaatgttcca cggaaacact ggtggacaga ttctagtgct   4080
gagaagaaac acgtttggtt tggagagtcc atggatggtg gttttcagtt tagctacggc   4140
aatcctgaac ttcctgaaga tgtccttgat gtgcagctgg cattccttcg acttctctcc   4200
agccgagctt cccagaacat cacatatcac tgcaaaaata gcattgcata catggatcag   4260
gccagtggaa atgtaaagaa ggccctgaag ctgatggggt caaatgaagg tgaattcaag   4320
gctgaaggaa atagcaaatt cacctacaca gttctggagg atggttgcac gaaacacact   4380
ggggaatgga gcaaaacagt ctttgaatat cgaacacgca aggctgtgag actacctatt   4440
gtagatattg caccctatga cattggtggt cctgatcaag aatttggtgt ggacgttggc   4500
cctgtttgct tttataaac caaactctat ctgaaatccc aacaaaaaaa atttaactcc   4560
atatgtgttc ctcttgttct aatcttgtca accagtgcaa gtgaccgaca aaattccagt   4620
tatttatttc caaaatgttt ggaaacagta taatttgaca aagaaaaatg atacttctct   4680
ttttttgctg ttccaccaaa tacaattcaa atgcttttg ttttattttt ttaccaattc   4740
caatttcaaa atgtctcaat ggtgctataa taaataaact tcaacactct ttatgataac   4800
aacactgtgt tatattcttt gaatcctagc ccatctgcag agcaatgact gtgctcacca   4860
gtaaaagata acctttcttt ctgaaatagt caaatacgaa attagaaaag ccctccctat   4920
tttaactacc tcaactggtc agaaacacag attgtattct atgagtccca gaagatgaaa   4980
aaaattttat acgttgataa aacttataaa tttcattgat taatctcctg gaagattggt   5040
ttaaaaagaa aagtgtaatg caagaattta aagaaatatt tttaaagcca caattatttt   5100
aatattggat atcaactgct tgtaaaggtg ctcctctttt ttcttgtcat tgctggtcaa   5160
gattactaat atttgggaag gctttaaaga cgcatgttat ggtgctaatg tactttcact   5220
tttaaactct agatcagaat tgttgacttg cattcagaac ataaatgcac aaaatctgta   5280
catgtctccc atcagaaaga ttcattggca tgccacaggg gattctcctc cttcatcctg   5340
taaaggtcaa caataaaaac caaattatgg ggctgctttt gtcacactag catagagaat   5400
gtgttgaaat ttaactttgt aagcttgtat gtggttgttg atcttttttt tccttacaga   5460
cacccataat aaaatatcat attaaaattc                                     5490
```

<210> SEQ ID NO 41
<211> LENGTH: 606
<212> TYPE: DNA
<213> ORGANISM: Homo sapiens

<400> SEQUENCE: 41

```
atgtccttcg ccacgctgcg cccggcgccg ccgggccgct acctgtaccc cgaggtgagc     60
ccgctgtcgg aggacgagga ccgcggcagc gacagctcgg gctccgacga gaaaccctgt    120
cgcgtgcacg cggcgcgctg cggcctccag ggcgcccggc ggagggcggg gggccggcgg    180
gccgggggcg gggggccagg gggccggcca ggccgtgagc cccggcagcg gcacacggcg    240
aacgcgcgcg agcgagaccg caccaacagc gtgaacacgg ccttcacggc gctgcgcacg    300
ctgatcccca ccgagcccgc cgaccgcaag ctctccaaga ttgagacgct gcgcctggcc    360
```

```
tccagctaca tctcgcacct gggcaacgtg ctgctggcgg gcgaggcctg cggcgacgga    420
cagccctgcc actccgggcc cgccttcttc cacgcggcgc gcgccggcag ccccccgccg    480
ccgcccccgc cgcctcccgc ccgcgacggc gagaacaccc agcccaaaca gatctgcacc    540
ttctgcctca gcaaccagag aaagttgagc aaggaccgcg acagaaagac agcgattcgc    600
agttag                                                               606
```

<210> SEQ ID NO 42
<211> LENGTH: 7616
<212> TYPE: DNA
<213> ORGANISM: Homo sapiens

<400> SEQUENCE: 42

```
attacagagg aaggagctcg ctatataagc cagccaaagt tggctgcacc ggccacagcc     60
tgcctactgt cacccgcctc tcccgcgcgc agatacacgc ccccgcctcc gtgggcacaa    120
aggcagcgct gctggggaac tcgggggaac gcgcacgtgg gaaccgccgc agctccacac    180
tccaggtact tcttccaagg acctaggtct ctcgcccatc ggaaagaaaa taattctttc    240
aagaagatca gggacaactg atttgaagtc tactctgtgc ttctaaatcc ccaattctgc    300
tgaaagtgag ataccctaga gccctagagc cccagcagca cccagccaaa cccacctcca    360
ccatgggggc catgactcag ctgttggcag gtgtctttct tgctttcctt gccctcgcta    420
ccgaaggtgg ggtcctcaag aaagtcatcc ggcacaagcg acagagtggg gtgaacgcca    480
ccctgccaga agagaaccag ccagtggtgt ttaaccacgt ttacaacatc aagctgccag    540
tgggatccca gtgttcggtg gatctggagt cagccagtgg ggagaaagac ctggcaccgc    600
cttcagagcc cagcgaaagc tttcaggagc acacagtgga tggggaaaac cagattgtct    660
tcacacatcg catcaacatc cccccgccggg cctgtggctg tgccgcagcc cctgatgtta    720
aggagctgct gagcagactg gaggagctgg agaacctggt gtcttccctg agggagcaat    780
gtactgcagg agcaggctgc tgtctccagc ctgccacagg ccgcttggac accaggccct    840
tctgtagcgg tcggggcaac ttcagcactg aaggatgtgg ctgtgtctgc gaacctggct    900
ggaaaggccc caactgctct gagcccgaat gtccaggcaa ctgtcacctt cgaggccggt    960
gcattgatgg gcagtgcatc tgtgacgacg gcttcacggg cgaggactgc agccagctgg   1020
cttgccccag cgactgcaat gaccagggca agtgcgtaaa tggagtctgc atctgtttcg   1080
aaggctacgc cggggctgac tgcagccgtg aaatctgccc agtgccctgc agtgaggagc   1140
acggcacatg tgtagatggc ttgtgtgtgt gccacgatgg ctttgcaggc gatgactgca   1200
acaagcctct gtgtctcaac aattgctaca accgtggacg atgcgtggag aatgagtgcg   1260
tgtgtgatga gggtttcacg ggcgaagact gcagtgagct catctgcccc aatgactgct   1320
tcgaccgggg ccgctgcatc aatggcacct gctactgcga agaaggcttc acaggtgaag   1380
actgcgggaa acccacctgc ccacatgcct gccacaccca gggccggtgt gaggaggggc   1440
agtgtgtatg tgatgagggc tttgccggtg tggactgcag cgagaagagg tgtcctgctg   1500
actgtcacaa tcgtggccgc tgtgtagacg ggcggtgtga gtgtgatgat ggtttcactg   1560
gagctgactg tggggagctc aagtgtccca atggctgcag tggccatggc cgctgtgtca   1620
atgggcagtg tgtgtgtgat gagggctata ctggggagga ctgcagccag ctacggtgcc   1680
ccaatgactg tcacagtcgg ggccgctgtg tcgagggcaa atgtgtatgt gagcaaggct   1740
tcaagggcta tgactgcagt gacatgagct gccctaatga ctgtcaccag cacggccgct   1800
```

-continued

```
gtgtgaatgg catgtgtgtt tgtgatgacg gctacacagg ggaagactgc cgggatcgcc   1860
aatgccccag ggactgcagc aacaggggcc tctgtgtgga cggacagtgc gtctgtgagg   1920
acggcttcac cggccctgac tgtgcagaac tctcctgtcc aaatgactgc catggccagg   1980
gtcgctgtgt gaatgggcag tgcgtgtgcc atgaaggatt tatgggcaaa gactgcaagg   2040
agcaaagatg tcccagtgac tgtcatggcc agggccgctg cgtggacggc cagtgcatct   2100
gccacgaggg cttcacaggc ctggactgtg gccagcactc ctgccccagt gactgcaaca   2160
acttaggaca atgcgtctcg ggccgctgca tctgcaacga gggctacagc ggagaagact   2220
gctcagaggt gtctcctccc aaagacctcg ttgtgacaga agtgacggaa gagacggtca   2280
acctggcctg ggacaatgag atgcgggtca cagagtacct tgtcgtgtac acgcccaccc   2340
acgagggtgg tctggaaatg cagttccgtg tgcctgggga ccagacgtcc accatcatcc   2400
aggagctgga gcctggtgtg gagtacttta tccgtgtatt tgccatcctg gagaacaaga   2460
agagcattcc tgtcagcgcc agggtggcca cgtacttacc tgcacctgaa ggcctgaaat   2520
tcaagtccat caaggagaca tctgtggaag tggagtggga tcctctagac attgcttttg   2580
aaacctggga gatcatcttc cggaatatga ataaagaaga tgagggagag atcaccaaaa   2640
gcctgaggag gccagagacc tcttaccggc aaactggtct agctcctggg caagagtatg   2700
agatatctct gcacatagtg aaaaacaata cccggggccc tggcctgaag agggtgacca   2760
ccacacgctt ggatgccccc agccagatcg aggtgaaaga tgtcacagac accactgcct   2820
tgatcacctg gttcaagccc ctggctgaga tcgatggcat tgagctgacc tacggcatca   2880
aagacgtgcc aggagaccgt accaccatcg atctcacaga ggacgagaac cagtactcca   2940
tcgggaacct gaagcctgac actgagtacg aggtgtccct catctcccgc agaggtgaca   3000
tgtcaagcaa cccagccaaa gagaccttca caacaggcct cgatgctccc aggaatcttc   3060
gacgtgtttc ccagacagat aacagcatca ccctggaatg gaggaatggc aaggcagcta   3120
ttgacagtta cagaattaag tatgccccca tctctggagg ggaccacgct gaggttgatg   3180
ttccaaagag ccaacaagcc acaaccaaaa ccacactcac aggtctgagg ccgggaactg   3240
aatatgggat tggagtttct gctgtgaagg aagacaagga gagcaatcca gcgaccatca   3300
acgcagccac agagttggac acgcccaagg accttcaggt ttctgaaact gcagagacca   3360
gcctgaccct gctctggaag acaccgttgg ccaaatttga ccgctaccgc ctcaattaca   3420
gtctccccac aggccagtgg gtgggagtgc agcttccaag aaacaccact tcctatgtcc   3480
tgagaggcct ggaaccagga caggagtaca atgtcctcct gacagccgag aaaggcagac   3540
acaagagcaa gcccgcacgt gtgaaggcat ccactgaaca agcccctgag ctggaaaacc   3600
tcaccgtgac tgaggttggc tgggatggcc tcagactcaa ctggaccgca gctgaccagg   3660
cctatgagca ctttatcatt caggtgcagg aggccaacaa ggtggaggca gctcggaacc   3720
tcaccgtgcc tggcagcctt cgggctgtgg acataccggg cctcaaggct gctacgcctt   3780
atacagtctc catctatggg gtgatccagg gctatagaac accagtgctc tctgctgagg   3840
cctccacagg ggaaactccc aatttgggag aggtcgtggt ggccgaggtg ggctgggatg   3900
ccctcaaact caactggact gctccagaag ggcctatga gtacttttttc attcaggtgc   3960
aggaggctga cacagtagag gcagcccaga acctcaccgt cccaggagga ctgaggtcca   4020
cagacctgcc tgggctcaaa gcagccactc attataccat caccatccgc ggggtcactc   4080
aggacttcag cacaacccct ctctctgttg aagtcttgac agaggaggtt ccagatatgg   4140
gaaacctcac agtgaccgag gttagctggg atgctctcag actgaactgg accacgccag   4200
```

atggaaccta tgaccagttt actattcagg tccaggaggc tgaccaggtg gaagaggctc 4260
acaatctcac ggttcctggc agcctgcgtt ccatggaaat cccaggcctc agggctggca 4320
ctccttacac agtcaccctg cacggcgagg tcaggggcca cagcactcga ccccttgctg 4380
tagaggtcgt cacagaggat ctcccacagc tgggagattt agccgtgtct gaggttggct 4440
gggatggcct cagactcaac tggaccgcag ctgacaatgc ctatgagcac tttgtcattc 4500
aggtgcagga ggtcaacaaa gtggaggcag cccagaacct cacgttgcct ggcagcctca 4560
gggctgtgga catcccgggc ctcgaggctg ccacgcctta tagagtctcc atctatgggg 4620
tgatccgggg ctatagaaca ccagtactct ctgctgaggc ctccacagcc aaagaacctg 4680
aaattggaaa cttaaatgtt tctgacataa ctcccgagag cttcaatctc tcctggatgg 4740
ctaccgatgg gatcttcgag acctttacca ttgaaattat tgattccaat aggttgctgg 4800
agactgtgga atataatatc tctggtgctg aacgaactgc ccatatctca gggctacccc 4860
ctagtactga ttttattgtc tacctctctg gacttgctcc cagcatccgg accaaaacca 4920
tcagtgccac agccacgaca gaggccctgc cccttctgga aaacctaacc atttccgaca 4980
ttaatcccta cgggttcaca gtttcctgga tggcatcgga gaatgccttt gacagctttc 5040
tagtaacggt ggtggattct gggaagctgc tggaccccca ggaattcaca ctttcaggaa 5100
cccagaggaa gctggagctt agaggcctca taactggcat tggctatgag gttatggtct 5160
ctggcttcac ccaagggcat caaaccaagc ccttgagggc tgagattgtt acagaagccg 5220
aaccggaagt tgacaacctt ctggtttcag atgccacccc agacggtttc cgtctgtcct 5280
ggacagctga tgaaggggtc ttcgacaatt ttgttctcaa aatcagagat accaaaaagc 5340
agtctgagcc actggaaata accctacttg cccccgaacg taccagggac ataacaggtc 5400
tcagagaggc tactgaatac gaaattgaac tctatggaat aagcaaagga aggcgatccc 5460
agacagtcag tgctatagca acaacagcca tgggctcccc aaaggaagtc attttctcag 5520
acatcactga aaattcggct actgtcagct ggagggcacc cacagcccaa gtggagagct 5580
tccggattac ctatgtgccc attacaggag gtacaccctc catggtaact gtggacggaa 5640
ccaagactca gaccaggctg gtgaaactca tacctggcgt ggagtacctt gtcagcatca 5700
tcgccatgaa gggctttgag gaaagtgaac ctgtctcagg gtcattcacc acagctctgg 5760
atggcccatc tggcctggtg acagccaaca tcactgactc agaagccttg gccaggtggc 5820
agccagccat tgccactgtg gacagttatg tcatctccta cacaggcgag aaagtgccag 5880
aaattacacg cacggtgtcc gggaacacag tggagtatgc tctgaccgac ctcgagcctg 5940
ccacggaata cacactgaga atctttgcag agaaagggcc ccagaagagc tcaaccatca 6000
ctgccaagtt cacaacagac ctcgattctc caagagactt gactgctact gaggttcagt 6060
cggaaactgc cctccttacc tggcgacccc cccgggcatc agtcaccggt tacctgctgg 6120
tctatgaatc agtggatggc acagtcaagg aagtcattgt gggtccagat accacctcct 6180
acagcctggc agacctgagc ccatccaccc actacacagc caagatccag gcactcaatg 6240
ggcccctgag gagcaatatg atccagacca tcttcaccac aattggactc ctgtacccct 6300
tccccaagga ctgctcccaa gcaatgctga atggagacac gacctctggc ctctacacca 6360
tttatctgaa tggtgataag gctgaggcgc tggaagtctt ctgtgacatg acctctgatg 6420
gggtggatg gattgtgttc ctgagacgca aaaacggacg cgagaacttc taccaaaact 6480
ggaaggcata tgctgctgga tttggggacc gcagagaaga attctggctt gggctggaca 6540

```
acctgaacaa aatcacagcc caggggcagt acgagctccg ggtggacctg cgggaccatg   6600
gggagacagc ctttgctgtc tatgacaagt tcagcgtggg agatgccaag actcgctaca   6660
agctgaaggt ggaggggtac agtgggacag caggtgactc catggcctac cacaatggca   6720
gatccttctc cacctttgac aaggacacag attcagccat caccaactgt gctctgtcct   6780
acaaaggggc tttctggtac aggaactgtc accgtgtcaa cctgatgggg agatatgggg   6840
acaataacca cagtcagggc gttaactggt tccactggaa gggccacgaa cactcaatcc   6900
agtttgctga gatgaagctg agaccaagca acttcagaaa tcttgaaggc aggcgcaaac   6960
gggcataaat tccagggacc actgggtgag agaggaataa ggcccagagc gaggaaagga   7020
ttttaccaaa gcatcaatac aaccagccca accatcggtc cacacctggg catttggtga   7080
gagtcaaagc tgaccatgga tccctggggc caacggcaac agcatgggcc tcacctcctc   7140
tgtgatttct ttctttgcac caaagacatc agtctccaac atgtttctgt tttgttgttt   7200
gattcagcaa aaatctccca gtgacaacat cgcaatagtt ttttacttct cttaggtggc   7260
tctgggaatg ggagaggggt aggatgtaca ggggtagttt gttttagaac cagccgtatt   7320
ttacatgaag ctgtataatt aattgtcatt atttttgtta gcaaagatta aatgtgtcat   7380
tggaagccat cccttttttt acatttcata caacagaaac cagaaaagca atactgtttc   7440
cattttaagg atatgattaa tattattaat ataataatga tgatgatgat gatgaaaact   7500
aaggattttt caagagatct ttctttccaa aacatttctg gacagtacct gattgtattt   7560
ttttttaaa taaaagcaca agtacttttg agtttgttaa aaaaaaaaaa aaaaaa      7616
```

```
<210> SEQ ID NO 43
<211> LENGTH: 1360
<212> TYPE: DNA
<213> ORGANISM: Homo sapiens

<400> SEQUENCE: 43

atggaattct gtgcacagaa gttatataca tatatgggta tatctatgta acaaatcgca     60
gcacaggagt cccctgggct ccctcaggct ctggtatgac atatttgagc catataaatt    120
cagcttctcc tctggcatct gttagccgac tcacttgcaa ctccacctca gcagtggtct    180
ctcagtcctc tcaaagcaag gaaagagtac tgtgtgctga gagaccatgg caaagaatcc    240
tccagagaat tgtgaagact gtcacattct aaatgcagaa gcttttaaat ccaagaaaat    300
atgtaaatca cttaagattt gtggactggt gtttggtatc ctggccctaa ctctaattgt    360
cctgttttgg gggagcaagc acttctggcc ggaggtaccc aaaaaagcct atgacatgga    420
gcacactttc tacagcaatg gagagaagaa gaagatttac atggaaattg atcctgtgac    480
cagaactgaa atattcagaa gcggaaatgg cactgatgaa acattggaag tgcacgactt    540
taaaaacgga tacactggca tctacttcgt gggtcttcaa aaatgtttta tcaaaactca    600
gattaaagtg attcctgaat tttctgaacc agaagaggaa atagatgaga atgaagaaat    660
taccacaact ttctttgaac agtcagtgat ttgggtccca gcagaaaagc ctattgaaaa    720
ccgagatttt cttaaaaatt ccaaaattct ggagatttgt gataacgtga ccatgtattg    780
gatcaatccc actctaatat cagtttctga gttacaagac tttgaggagg agggagaaga    840
tcttcacttt cctgccaacg aaaaaaaagg gattgaacaa aatgaacagt gggtggtccc    900
tcaagtgaaa gtagagaaga cccgtcacgc cagacaagca agtgaggaag aacttccaat    960
aaatgactat actgaaaatg gaatagaatt tgatcccatg ctggatgaga gaggttattg   1020
ttgtatttac tgccgtcgag gcaaccgcta ttgccgccgc gtctgtgaac ctttactagg   1080
```

ctactaccca tatccatact gctaccaagg aggacgagtc atctgtcgtg tcatcatgcc 1140
ttgtaactgg tgggtggccc gcatgctggg gagggtctaa taggaggttt gagctcaaat 1200
gcttaaactg ctggcaacat ataataaatg catgctattc aatgaatttc tgcctatgag 1260
gcatctggcc cctggtagcc agctctccag aattacttgt aggtaattcc tctcttcatg 1320
ttctaataaa cttctacatt atcaccaaaa aaaaaaaaaa 1360

<210> SEQ ID NO 44
<211> LENGTH: 3480
<212> TYPE: DNA
<213> ORGANISM: Homo sapiens

<400> SEQUENCE: 44
ctccctcttt ccctcacagc cgacgaggca acaattaggc tttggggata aaacgaggtg 60
cggagagcgg gctggggcat ttctccccga gatggcgggt ctgacggcgg cggccccgcg 120
gcccggagtc ctcctgctcc tgctgtccat cctccacccc tctcggcctg gaggggtccc 180
tggggccatt cctggtggag ttcctggagg agtcttttat ccaggggctg gtctcggagc 240
ccttggagga ggagcgctgg ggcctggagg caaacctctt aagccagttc ccggagggct 300
tgcgggtgct ggccttgggg cagggctcgg cgccttcccc gcagttacct ttccgggggc 360
tctggtgcct ggtggagtgg ctgacgctgc tgcagcctat aaagctgcta aggctggcgc 420
tgggcttggt ggtgtcccag gagttggtgg cttaggagtg tctgcaggtg cggtggttcc 480
tcagcctgga gccggagtga agcctgggaa agtgccgggt gtggggctgc caggtgtata 540
cccaggtggc gtgctcccag gagctcggtt ccccggtgtg gggtgctcc ctggagttcc 600 cactggagca ggagttaagc ccaaggctcc aggtgtaggt ggagcttttg ctggaatccc 660
aggagttgga ccctttgggg gaccgcaacc tggagtccca ctggggtatc ccatcaaggc 720
ccccaagctg cctggtggct atggactgcc ctacaccaca gggaaactgc cctatggcta 780
tgggcccgga ggagtggctg gtgcagcggg caaggctggt tacccaacag ggacaggggt 840
tggcccccag gcagcagcag cagcggcagc taaagcagca gcaaagttcg gtgctggagc 900
agccggagtc ctccctggtg ttggaggggc tggtgttcct ggcgtgcctg gggcaattcc 960
tggaattgga ggcatcgcag gcgttgggac tccagctgca gctgcagctg cagcagcagc 1020
cgctaaggca gccaagtatg gagctgctgc aggcttagtg cctggtgggc caggctttgg 1080
cccgggagta gttggtgtcc caggagctgg cgttccaggt gttggtgtcc caggagctgg 1140
gattccagtt gtcccaggtg ctgggatccc aggtgctgcg gttccagggg ttgtgtcacc 1200
agaagcagct gctaaggcag ctgcaaaggc agccaaatac ggggccaggc ccggagtcgg 1260
agttggaggc attcctactt acggggttgg agctgggggc tttcccggct ttggtgtcgg 1320
agtcggaggt atccctggag tcgcaggtgt ccctggtgtc ggaggtgttc ccggagtcgg 1380
aggtgtcccg ggagttggca tttcccccga agctcaggca gcagctgccg ccaaggctgc 1440
caagtacgga gtggggaccc cagcagctgc agctgctaaa gcagccgcca aagccgccca 1500
gtttgggtta gttcctggtg tcggcgtggc tcctggagtt ggcgtggctc ctggtgtcgg 1560
tgtggctcct ggagttggct tggctcctgg agttggcgtg gctcctggag ttggtgtggc 1620
tcctggcgtt ggcgtggctc ccggcattgg ccctggtgga gttgcagctg cagcaaaatc 1680
cgctgccaag gtggctgcca aagcccagct ccgagctgca gctgggcttg gtgctggcat 1740
ccctggactt ggagttggtg tcggcgtccc tggacttgga gttggtgctg gtgttcctgg 1800
acttggagtt ggtgctggtg ttcctggctt cggggcagta cctggagccc tggctgccgc 1860
taaagcagcc aaatatggag cagcagtgcc tggggtcctt ggagggctcg ggctctcgg 1920 tggagtaggc atcccaggcg gtgtggtggg agccggaccc gccgccgccg ctgccgcagc 1980
caaagctgct gccaaagccg cccagtttgg cctagtggga gccgctgggc tcggaggact 2040
cggagtcgga gggcttggag ttccaggtgt tgggggcctt ggaggtatac ctccagctgc 2100
agccgctaaa gcagctaaat acggtgctgc tggccttgga ggtgtcctag gggtgccgg 2160 gcagttccca cttggaggag tggcagcaag acctggcttc ggattgtctc ccatttttccc 2220 aggtggggcc tgcctgggga aagcttgtgg ccggaagaga aaatgagctt cctaggaccc 2280
ctgactcacg acctcatcaa cgttggtgct actgcttggt ggagaatgta aaccctttgt 2340
aaccccatcc catgcccctc cgactcccca ccccaggagg gaacgggcag gccgggcggc 2400
cttgcagatc cacagggcaa ggaaacaaga ggggagcggc caagtgcccc gaccaggagg 2460
ccccctactt cagaggcaag ggccatgtgg tcctggcccc ccaccccatc ccttcccacc 2520
taggagctcc ccctccacac agcctccatc tccaggggaa cttggtgcta cacgctggtg 2580
ctcttatctt cctgggggga gggaggaggg aagggtggcc cctcggggaa ccccctacct 2640
ggggctcctc taaagatggt gcagacactt cctgggcagt cccagctccc cctgcccacc 2700
aggacccacc gttggctgcc atccagttgg tacccaagca cctgaagcct caaagctgga 2760
ttcgctctag catccctcct ctcctgggtc cacttggccg tctcctcccc accgatcgct 2820
gttccccaca tctggggcgc ttttgggttg gaaaaccacc ccacactggg aatagccacc 2880
ttgcccttgt agaatccatc cgcccatccg tccattcatc catcggtccg tccatccatg 2940
tccccagttg accgcccggc accactagct ggctgggtgc acccaccatc aacctggttg 3000
acctgtcatg gccgcctgtg ccctgcctcc acccccatcc tacactcccc cagggcgtgc 3060
ggggctgtgc agactggggt gccaggcatc tcctccccac ccggggtgtc cccacatgca 3120
gtactgtata ccccccatcc ctccctcggt ccactgaact tcagagcagt tcccattcct 3180
gccccgccca tctttttgtg tctcgctgtg atagatcaat aaatatttta ttttttgtcc 3240
tggatatttg gggattattt ttgattgttg atattctctt ttggttttat tgttgtggtt 3300
cattgaaaaa aaaagataat tttttttttct gatccgggga gctgtatccc cagtagaaaa 3360
aacattttaa tcactctaat ataactctgg atgaaacaca cctttttttt taataagaaa 3420
agagaattaa ctgcttcaga aatgactaat aaatgaaaaa cctttaaagg aaaaaaaaaa 3480

<210> SEQ ID NO 45
<211> LENGTH: 2305
<212> TYPE: DNA
<213> ORGANISM: Homo sapiens

<400> SEQUENCE: 45
gaatctacaa taagacaaat ttcaaatcaa gttgctccac tatactgcat aagcagttta 60
gaatcttaag cagatgcaaa aagaataaag caaatgggag gaaaaaaaag gccgataaag 120
tttctggcta caatacaaga gacatatcat taccatatga tctaatgtgg gtgtcagccg 180
gattgtgttc attgagggaa accttatttt ttaactgtgc tatggagtag aagcaggagg 240
ttttcaacct agtcacagag cagcacctac cccctcctcc tttccacacc tgcaaactct 300
tttacttggg ctgaatattt agtgtaatta catctcagct ttgagggctc ctgtggcaaa 360
ttcccggatt aaaaggttcc ctggttgtga aaatacatga gataaatcat gaaggccact 420
atcatcctcc ttctgcttgc acaagtttcc tgggctggac cgtttcaaca gagaggctta 480

```
tttgacttta tgctagaaga tgaggcttct gggataggcc cagaagttcc tgatgaccgc    540
gacttcgagc cctccctagg cccagtgtgc cccttccgct gtcaatgcca tcttcgagtg    600
gtccagtgtt ctgatttggg tctggacaaa gtgccaaagg atcttccccc tgacacaact    660
ctgctagacc tgcaaaacaa caaaataacc gaaatcaaag atggagactt taagaacctg    720
aagaaccttc acgcattgat tcttgtcaac aataaaatta gcaaagttag tcctggagca    780
tttacacctt tggtgaagtt ggaacgactt tatctgtcca agaatcagct gaaggaattg    840
ccagaaaaaa tgcccaaaac tcttcaggag ctgcgtgccc atgagaatga gatcaccaaa    900
gtgcgaaaag ttactttcaa tggactgaac cagatgattg tcatagaact gggcaccaat    960
ccgctgaaga gctcaggaat tgaaaatggg gctttccagg gaatgaagaa gctctcctac   1020
atccgcattg ctgataccaa tatcaccagc attcctcaag gtcttcctcc ttcccttacg   1080
gaattacatc ttgatggcaa caaaatcagc agagttgatg cagctagcct gaaaggactg   1140
aataatttgg ctaagttggg attgagtttc aacagcatct ctgctgttga caatggctct   1200
ctggccaaca cgcctcatct gagggagctt cacttggaca acaacaagct taccagagta   1260
cctggtgggc tggcagagca taagtacatc caggttgtct accttcataa caacaatatc   1320
tctgtagttg gatcaagtga cttctgccca cctggacaca acaccaaaaa ggcttcttat   1380
tcgggtgtga gtcttttcag caacccggtc cagtactggg agatacagcc atccaccttc   1440
agatgtgtct acgtgcgctc tgccattcaa ctcggaaact ataagtaatt ctcaagaaag   1500
ccctcatttt tataacctgg caaaatcttg ttaatgtcat tgctaaaaaa taaataaaag   1560
ctagatactg gaaacctaac tgcaatgtgg atgttttacc cacatgactt attatgcata   1620
aagccaaatt tccagtttaa gtaattgcct acaataaaaa gaaattttgc ctgccatttt   1680
cagaatcatc ttttgaagct ttctgttgat gttaactgag ctactagaga tattcttatt   1740
tcactaaatg taaaatttgg agtaaatata tatgtcaata tttagtaaag cttttctttt   1800
ttaatttcca ggaaaaaata aaaagagtat gagtcttctg taattcattg agcagttagc   1860
tcatttgaga taaagtcaaa tgccaaacac tagctctgta ttaatcccca tcattactgg   1920
taaagcctca tttgaatgtg tgaattcaat acaggctatg taaaattttt actaatgtca   1980
ttattttgaa aaaataaatt taaaaataca ttcaaaatta ctattgtata caagcttaat   2040
tgttaatatt ccctaaacac aattttatga agggagaaga cattggtttg ttgacaataa   2100
cagtacatct tttcaagttc tcagctattt cttctacctc tccctatctt acatttgagt   2160
atggtaactt atgtcatcta tgttgaatgt aagcttataa agcacaaagc atacatttcc   2220
tgactggtct agagaactga tgtttcaatt taccccctctg ctaaataaat attaaaacta   2280
tcatgtgaaa aaaaaaaaaa aaaaa                                         2305
```

<210> SEQ ID NO 46
<211> LENGTH: 2465
<212> TYPE: DNA
<213> ORGANISM: Homo sapiens

<400> SEQUENCE: 46

```
cctttcctcc ctccccgccc tctccccgct gtcccctccc cgtcggcccg cctgcccagc     60
ctttagcctc ccgcccgccg cctctgtctc cctctctcca caaactgccc aggagtgagt    120
agctgctttc ggtccgccgg acacaccgga cagatagacg tgcggacggc ccaccacccc    180
agcccgccaa ctagtcagcc tgcgcctggc gcctcccctc tccaggtcca tccgccatgt    240
```

-continued

```
ggcccctgtg gcgcctcgtg tctctgctgg ccctgagcca ggccctgccc tttgagcaga    300
gaggcttctg ggacttcacc ctggacgatg ggccattcat gatgaacgat gaggaagctt    360
cgggcgctga cacctcgggc gtcctggacc cggactctgt cacacccacc tacagcgcca    420
tgtgtccttt cggctgccac tgccacctgc gggtggttca gtgctccgac ctgggtctga    480
agtctgtgcc caaagagatc tcccctgaca ccacgctgct ggacctgcag aacaacgaca    540
tctccgagct ccgcaaggat gacttcaagg gtctccagca cctctacgcc ctcgtcctgg    600
tgaacaacaa gatctccaag atccatgaga aggccttcag cccactgcgg aagctgcaga    660
agctctacat ctccaagaac cacctggtgg agatcccgcc caacctaccc agctccctgg    720
tggagctccg catccacgac aaccgcatcc gcaaggtgcc caagggagtg ttcagcgggc    780
tccggaacat gaactgcatc gagatgggcg ggaacccact ggagaacagt ggctttgaac    840
ctggagcctt cgatggcctg aagctcaact acctgcgcat ctcagaggcc aagctgactg    900
gcatccccaa agacctccct gagaccctga atgaactcca cctagaccac aacaaaatcc    960
aggccatcga actggaggac ctgcttcgct actccaagct gtacaggctg ggcctaggcc   1020
acaaccagat caggatgatc gagaacggga gcctgagctt cctgcccacc ctccgggagc   1080
tccacttgga caacaacaag ttggccaggg tgccctcagg gctcccagac ctcaagctcc   1140
tccaggtggt ctatctgcac tccaacaaca tcaccaaagt gggtgtcaac gacttctgtc   1200
ccatgggctt cggggtgaag cgggcctact acaacggcat cagcctcttc aacaaccccg   1260
tgccctactg ggaggtgcag ccggccactt tccgctgcgt cactgaccgc ctggccatcc   1320
agtttggcaa ctacaaaaag tagaggcagc tgcagccacc gcggggcctc agtgggggtc   1380
tctggggaac acagccagac atcctgatgg ggaggcagag ccaggaagct aagccagggc   1440
ccagctgcgt ccaacccagc cccccacctc gggtccctga ccccagctcg atgccccatc   1500
accgcctctc cctggctccc aagggtgcag gtgggcgcaa ggcccggccc ccatcacatg   1560
ttcccttggc ctcagagctg cccctgctct cccaccacag ccacccagag gcaccccatg   1620
aagctttttt ctcgttcact cccaaaccca agtgtccaag gctccagtcc taggagaaca   1680
gtccctgggt cagcagccag gaggcggtcc ataagaatgg ggacagtggg ctctgccagg   1740
gctgccgcac ctgtccagac acacatgttc tgttcctcct cctcatgcat ttccagcctt   1800
tcaaccctcc ccgactctgc ggctcccctc agcccccttg caagttcatg gcctgtccct   1860
cccagacccc tgctccactg gcccttcgac cagtcctccc ttctgttctc tctttccccg   1920
tccttcctct ctctctctct ctctctctct ctctctttct gtgtgtgtgt gtgtgtgtgt   1980
gtgtgtgtgt gtgtgtgtgt gtgtcttgtg cttcctcaga cctttctcgc ttctgagctt   2040
ggtggcctgt tccctccatc tctccgaacc tggcttcgcc tgtccctttc actccacacc   2100
ctctggcctt ctgccttgag ctgggactgc tttctgtctg tccggcctgc acccagcccc   2160
tgcccacaaa accccaggga cagcagtctc cccagcctgc cctgctcagg ccttgccccc   2220
aaacctgtac tgtcccggag gaggttggga ggtggaggcc cagcatcccg cgcagatgac   2280
accatcaacc gccagagtcc cagacaccgg ttttcctaga agcccctcac ccccactggc   2340
ccactggtgg ctaggtctcc ccttatcctt ctggtccagc gcaaggaggg gctgcttctg   2400
aggtcggtgg ctgtctttcc attaaagaaa caccgtgcaa cgtgaaaaaa aaaaaaaaaa   2460
aaaaa                                                               2465
```

<210> SEQ ID NO 47
<211> LENGTH: 8374

<212> TYPE: DNA
<213> ORGANISM: Homo sapiens

<400> SEQUENCE: 47
gcccgcgccg gctgtgctgc acagggggag gagagggaac cccaggcgcg agcgggaaga 60
ggggacctgc agccacaact tctctggtcc tctgcatccc ttctgtccct ccacccgtcc 120
ccttccccac cctctggccc ccaccttctt ggaggcgaca acccccggga ggcattagaa 180
gggatttttc ccgcaggttg cgaagggaag caaacttggt ggcaacttgc ctcccggtgc 240
gggcgtctct cccccaccgt ctcaacatgc ttaggggtcc ggggcccggg ctgctgctgc 300
tggccgtcca gtgcctgggg acagcggtgc cctccacggg agcctcgaag agcaagaggc 360
aggctcagca aatggttcag ccccagtccc cggtggctgt cagtcaaagc aagcccggtt 420
gttatgacaa tggaaaacac tatcagataa atcaacagtg ggagcggacc tacctaggca 480
atgcgttggt ttgtacttgt tatggaggaa gccgaggttt taactgcgag agtaaacctg 540
aagctgaaga gacttgcttt gacaagtaca ctgggaacac ttaccgagtg ggtgacactt 600
atgagcgtcc taaagactcc atgatctggg actgtacctg catcggggct gggcgaggga 660
gaataagctg taccatcgca aaccgctgcc atgaaggggg tcagtcctac aagattggtg 720
acacctggag gagaccacat gagactggtg gttacatgtt agagtgtgtg tgtcttggta 780
atggaaaagg agaatggacc tgcaagccca tagctgagaa gtgttttgat catgctgctg 840
ggacttccta tgtggtcgga gaaacgtggg agaagcccta ccaaggctgg atgatggtag 900
attgtacttg cctgggagaa ggcagcggac gcatcacttg cacttctaga aatagatgca 960
acgatcagga cacaaggaca tcctatagaa ttggagacac ctggagcaag aaggataatc 1020
gaggaaacct gctccagtgc atctgcacag gcaacggccg aggagagtgg aagtgtgaga 1080
ggcacacctc tgtgcagacc acatcgagcg gatctggccc cttcaccgat gttcgtgcag 1140
ctgtttacca accgcagcct cacccccagc ctcctcccta tggccactgt gtcacagaca 1200
gtggtgtggt ctactctgtg gggatgcagt ggctgaagac acaaggaaat aagcaaatgc 1260
tttgcacgtg cctgggcaac ggagtcagct gccaagagac agctgtaacc cagacttacg 1320
gtggcaactc aaatggagag ccatgtgtct taccattcac ctacaatggc aggacgttct 1380
actcctgcac cacagaaggg cgacaggacg gacatctttg gtgcagcaca acttcgaatt 1440
atgagcagga ccagaaatac tctttctgca cagaccacac tgttttggtt cagactcgag 1500
gaggaaattc caatggtgcc ttgtgccact tccccttcct atacaacaac cacaattaca 1560
ctgattgcac ttctgagggc agaagagaca acatgaagtg gtgtgggacc acacagaact 1620
atgatgccga ccagaagttt gggttctgcc ccatggctgc ccacgaggaa atctgcacaa 1680
ccaatgaagg ggtcatgtac cgcattggag atcagtggga taagcagcat gacatgggtc 1740
acatgatgag gtgcacgtgt gttgggaatg gtcgtgggga atggacatgc attgcctact 1800
cgcagcttcg agatcagtgc attgttgatg acatcactta caatgtgaac gacacattcc 1860
acaagcgtca tgaagagggg cacatgctga actgtacatg cttcggtcag ggtcggggca 1920
ggtggaagtg tgatcccgtc gaccaatgcc aggattcaga gactgggacg ttttatcaaa 1980
ttggagattc atgggagaag tatgtgcatg gtgtcagata ccagtgctac tgctatggcc 2040
gtggcattgg ggagtggcat tgccaacctt tacagaccta tccaagctca agtggtcctg 2100
tcgaagtatt tatcactgag actccgagtc agcccaactc ccaccccatc cagtggaatg 2160
caccacagcc atctcacatt tccaagtaca ttctcaggtg gagacctaaa aattctgtag 2220

-continued

```
gccgttggaa ggaagctacc ataccaggcc acttaaactc ctacaccatc aaaggcctga   2280
agcctggtgt ggtatacgag ggccagctca tcagcatcca gcagtacggc caccaagaag   2340
tgactcgctt tgacttcacc accaccagca ccagcacacc tgtgaccagc aacaccgtga   2400
caggagagac gactcccttt tctcctcttg tggccacttc tgaatctgtg accgaaatca   2460
cagccagtag ctttgtggtc tcctgggtct cagcttccga caccgtgtcg ggattccggg   2520
tggaatatga gctgagtgag gagggagatg agccacagta cctggatctt ccaagcacag   2580
ccacttctgt gaacatccct gacctgcttc ctggccgaaa atacattgta aatgtctatc   2640
agatatctga ggatggggag cagagtttga tcctgtctac ttcacaaaca acagcgcctg   2700
atgcccctcc tgacccgact gtggaccaag ttgatgacac ctcaattgtt gttcgctgga   2760
gcagacccca ggctcccatc acagggtaca gaatagtcta ttcgccatca gtagaaggta   2820
gcagcacaga actcaacctt cctgaaactg caaactccgt caccctcagt gacttgcaac   2880
ctggtgttca gtataacatc actatctatg ctgtggaaga aaatcaagaa agtacacctg   2940
ttgtcattca acaagaaacc actggcaccc cacgctcaga tacagtgccc tctcccaggg   3000
acctgcagtt tgtggaagtg acagacgtga aggtcaccat catgtggaca ccgcctgaga   3060
gtgcagtgac cggctaccgt gtggatgtga tccccgtcaa cctgcctggc gagcacgggc   3120
agaggctgcc catcagcagg aacacctttg cagaagtcac cgggctgtcc cctggggtca   3180
cctattactt caaagtcttt gcagtgagcc atgggaggga gagcaagcct ctgactgctc   3240
aacagacaac caaactggat gctcccacta acctccagtt tgtcaatgaa actgattcta   3300
ctgtcctggt gagatggact ccacctcggg cccagataac aggataccga ctgaccgtgg   3360
gccttacccg aagaggacag cccaggcagt acaatgtggg tccctctgtc tccaagtacc   3420
cactgaggaa tctgcagcct gcatctgagt acaccgtatc cctcgtggcc ataaagggca   3480
accaagagag ccccaaagcc actggagtct ttaccacact gcagcctggg agctctattc   3540
caccttacaa caccgaggtg actgagacca ccattgtgat cacatggacg cctgctccaa   3600
gaattggttt taagctgggt gtacgaccaa gccagggagg agaggcacca cgagaagtga   3660
cttcagactc aggaagcatc gttgtgtccg gcttgactcc aggagtagaa tacgtctaca   3720
ccatccaagt cctgagagat ggacaggaaa gagatgcgcc aattgtaaac aaagtggtga   3780
caccattgtc tccaccaaca aacttgcatc tggaggcaaa ccctgacact ggagtgctca   3840
cagtctcctg ggagaggagc accaccccag acattactgg ttatagaatt accacaaccc   3900
ctacaaacgg ccagcaggga aattctttgg aagaagtggt ccatgctgat cagagctcct   3960
gcacttttga taacctgagt cccggcctgg agtacaatgt cagtgtttac actgtcaagg   4020
atgacaagga aagtgtccct atctctgata ccatcatccc agctgttcct cctcccactg   4080
acctgcgatt caccaacatt ggtccagaca ccatgcgtgt cacctgggct ccacccccat   4140
ccattgattt aaccaacttc ctggtgcgtt actcacctgt gaaaaatgag gaagatgttg   4200
cagagttgtc aatttctcct tcagacaatg cagtggtctt aacaaatctc ctgcctggta   4260
cagaatatgt agtgagtgtc tccagtgtct acgaacaaca tgagagcaca cctcttagag   4320
gaagacagaa aacaggtctt gattccccaa ctggcattga cttttctgat attactgcca   4380
actcttttac tgtgcactgg attgctcctc gagccaccat cactggctac aggatccgcc   4440
atcatcccga gcacttcagt gggagacctc gagaagatcg ggtgccccac tctcggaatt   4500
ccatcaccct caccaacctc actccaggca cagagtatgt ggtcagcatc gttgctctta   4560
atggcagaga ggaaagtccc ttattgattg gccaacaatc aacagtttct gatgttccga   4620
```

-continued

```
gggacctgga agttgttgct gcgaccccca ccagcctact gatcagctgg gatgctcctg   4680
ctgtcacagt gagatattac aggatcactt acggagagac aggaggaaat agccctgtcc   4740
aggagttcac tgtgcctggg agcaagtcta cagctaccat cagcggcctt aaacctggag   4800
ttgattatac catcactgtg tatgctgtca ctggccgtgg agacagcccc gcaagcagca   4860
agccaatttc cattaattac cgaacagaaa ttgacaaacc atcccagatg caagtgaccg   4920
atgttcagga caacagcatt agtgtcaagt ggctgccttc aagttcccct gttactggtt   4980
acagagtaac caccactccc aaaaatggac caggaccaac aaaaactaaa actgcaggtc   5040
cagatcaaac agaaatgact attgaaggct tgcagcccac agtggagtat gtggttagtg   5100
tctatgctca gaatccaagc ggagagagtc agcctctggt tcagactgca gtaaccaaca   5160
ttgatcgccc taaaggactg gcattcactg atgtggatgt cgattccatc aaaattgctt   5220
gggaaagccc acaggggcaa gtttccaggt acagggtgac ctactcgagc cctgaggatg   5280
gaatccatga gctattccct gcacctgatg gtgaagaaga cactgcagag ctgcaaggcc   5340
tcagaccggg ttctgagtac acagtcagtg tggttgcctt gcacgatgat atggagagcc   5400
agcccctgat tggaacccag tccacagcta ttcctgcacc aactgacctg aagttcactc   5460
aggtcacacc cacaagcctg agcgcccagt ggacaccacc caatgttcag ctcactggat   5520
atcgagtgcg ggtgaccccc aaggagaaga ccggaccaat gaaagaaatc aaccttgctc   5580
ctgacagctc atccgtggtt gtatcaggac ttatggtggc caccaaatat gaagtgagtg   5640
tctatgctct taaggacact ttgacaagca gaccagctca gggagttgtc accactctgg   5700
agaatgtcag cccaccaaga agggctcgtg tgacagatgc tactgagacc accatcacca   5760
ttagctggag aaccaagact gagacgatca ctggcttcca agttgatgcc gttccagcca   5820
atggccagac tccaatccag agaaccatca agccagatgt cagaagctac accatcacag   5880
gtttacaacc aggcactgac tacaagatct acctgtacac cttgaatgac aatgctcgga   5940
gctcccctgt ggtcatcgac gcctccactg ccattgatgc accatccaac ctgcgtttcc   6000
tggccaccac acccaattcc ttgctggtat catggcagcc gccacgtgcc aggattaccg   6060
gctacatcat caagtatgag aagcctgggt ctcctcccag agaagtggtc cctcggcccc   6120
gccctggtgt cacagaggct actattactg gcctggaacc gggaaccgaa tatacaattt   6180
atgtcattgc cctgaagaat aatcagaaga gcgagcccct gattggaagg aaaaagacag   6240
ttcaaaagac ccctttcgtc acccaccctg ggtatgacac tggaaatggt attcagcttc   6300
ctggcacttc tggtcagcaa cccagtgttg ggcaacaaat gatctttgag gaacatggtt   6360
ttaggcggac cacaccgccc acaacggcca cccccataag gcataggcca agaccatacc   6420
cgccgaatgt aggacaagaa gctctctctc agacaaccat ctcatgggcc ccattccagg   6480
acacttctga gtacatcatt tcatgtcatc ctgttggcac tgatgaagaa cccttacagt   6540
tcagggttcc tggaacttct accagtgcca ctctgacagg cctcaccaga ggtgccacct   6600
acaacatcat agtggaggca ctgaaagacc agcagaggca taaggttcgg gaagaggttg   6660
ttaccgtggg caactctgtc aacgaaggct tgaaccaacc tacggatgac tcgtgctttg   6720
acccctacac agtttcccat tatgccgttg gagatgagtg ggaacgaatg tctgaatcag   6780
gctttaaact gttgtgccag tgcttaggct ttggaagtgg tcatttcaga tgtgattcat   6840
ctagatggtg ccatgacaat ggtgtgaact acaagattgg agagaagtgg gaccgtcagg   6900
gagaaaatgg ccagatgatg agctgcacat gtcttgggaa cggaaaagga gaattcaagt   6960
```

gtgaccctca tgaggcaacg tgttatgatg atgggaagac ataccacgta ggagaacagt 7020
ggcagaagga atatctcggt gccatttgct cctgcacatg ctttggaggc cagcggggct 7080
ggcgctgtga caactgccgc agacctgggg gtgaacccag tcccgaaggc actactggcc 7140
agtcctacaa ccagtattct cagagatacc atcagagaac aaacactaat gttaattgcc 7200
caattgagtg cttcatgcct ttagatgtac aggctgacag agaagattcc cgagagtaaa 7260
tcatctttcc aatccagagg aacaagcatg tctctctgcc aagatccatc taaactggag 7320
tgatgttagc agacccagct tagagttctt ctttctttct taagcccttt gctctggagg 7380
aagttctcca gcttcagctc aactcacagc ttctccaagc atcaccctgg gagtttcctg 7440
agggttttct cataaatgag ggctgcacat tgcctgttct gcttcgaagt attcaatacc 7500
gctcagtatt ttaaatgaag tgattctaag atttggtttg ggatcaatag gaaagcatat 7560
gcagccaacc aagatgcaaa tgttttgaaa tgatatgacc aaaattttaa gtaggaaagt 7620
cacccaaaca cttctgcttt cacttaagtg tctggcccgc aatactgtag gaacaagcat 7680
gatcttgtta ctgtgatatt ttaaatatcc acagtactca ctttttccaa atgatcctag 7740
taattgccta gaaatatctt tctcttacct gttatttatc aatttttccc agtattttta 7800
tacggaaaaa attgtattga aaacacttag tatgcagttg ataagaggaa tttggtataa 7860
ttatggtggg tgattatttt ttatactgta tgtgccaaag ctttactact gtggaaagac 7920
aactgtttta ataaaagatt tacattccac aacttgaagt tcatctattt gatataagac 7980
accttcgggg gaaataattc ctgtgaatat tctttttcaa ttcagcaaac atttgaaaat 8040
ctatgatgtg caagtctaat tgttgatttc agtacaagat tttctaaatc agttgctaca 8100
aaaactgatt ggtttttgtc acttcatctc ttcactaatg gagatagctt tacactttct 8160
gctttaatag atttaagtgg accccaatat ttattaaaat tgctagttta ccgttcagaa 8220
gtataataga aataatcttt agttgctctt ttctaaccat tgtaattctt cccttcttcc 8280
ctccaccttt ccttcattga ataaacctct gttcaaagag attgcctgca agggaaataa 8340
aaatgactaa gatattaaaa aaaaaaaaaa aaaa 8374

<210> SEQ ID NO 48
<211> LENGTH: 3963
<212> TYPE: DNA
<213> ORGANISM: Homo sapiens

<400> SEQUENCE: 48
ggagagccga aagcggagct cgaaactgac tggaaacttc agtggcgcgg agactcgcca 60
gtttcaaccc cggaaacttt tctttgcagg aggagaagag aaggggtgca agcgccccca 120
cttttgctct tttcctccc ctcctcctcc tctccaattc gcctcccccc acttggagcg 180
ggcagctgtg aactggccac cccgcgcctt cctaagtgct cgccgcggta gccggccgac 240
gcgccagctt ccccgggagc cgcttgctcc gcatccgggc agccgagggg agaggagccc 300
gcgcctcgag tccccgagcc gccgcggctt ctcgcctttc ccggccacca gccccctgcc 360
ccgggcccgc gtatgaatct cctggacccc ttcatgaaga tgaccgacga gcaggagaag 420
ggcctgtccg gcgcccccag ccccaccatg tccgaggact ccgcgggctc gccctgcccg 480
tcgggctccg gctcggacac cgagaacacg cggccccagg agaacacgtt ccccaagggc 540
gagcccgatc tgaagaagga gagcgaggag gacaagttcc ccgtgtgcat ccgcgaggcg 600
gtcagccagg tgctcaaagg ctacgactgg acgctggtgc ccatgccggt gcgcgtcaac 660
ggctccagca agaacaagcc gcacgtcaag cggcccatga acgccttcat ggtgtgggcg 720

-continued

```
caggcggcgc gcaggaagct cgcggaccag tacccgcact tgcacaacgc cgagctcagc    780
aagacgctgg gcaagctctg gagacttctg aacgagagcg agaagcggcc cttcgtggag    840
gaggcggagc ggctgcgcgt gcagcacaag aaggaccacc cggattacaa gtaccagccg    900
cggcggagga agtcggtgaa gaacgggcag gcggaggcag aggaggccac ggagcagacg    960
cacatctccc ccaacgccat cttcaaggcg ctgcaggccg actcgccaca ctcctcctcc   1020
ggcatgagcg aggtgcactc ccccggcgag cactcggggc aatcccaggg cccaccgacc   1080
ccacccacca cccccaaaac cgacgtgcag ccgggcaagg ctgacctgaa gcgagagggg   1140
cgcccccttgc cagagggggg cagacagccc cctatcgact tccgcgacgt ggacatcggc   1200
gagctgagca gcgacgtcat ctccaacatc gagaccttcg atgtcaacga gtttgaccag   1260
tacctgccgc ccaacggcca cccgggggtg ccggccacgc acggccaggt cacctacacg   1320
ggcagctacg gcatcagcag caccgcggcc accccggcga gcgcgggcca cgtgtggatg   1380
tccaagcagc aggcgccgcc gccacccccg cagcagcccc cacaggcccc gccggccccg   1440
caggcgcccc cgcagccgca ggcggcgccc ccacagcagc cggcggcacc cccgcagcag   1500
ccacaggcgc acacgctgac cacgctgagc agcgagccgg gccagtccca gcgaacgcac   1560
atcaagacgg agcagctgag ccccagccac tacagcgagc agcagcagca ctcgccccaa   1620
cagatcgcct acagcccctt caacctccca cactacagcc cctcctaccc gcccatcacc   1680
cgctcacagt acgactacac cgaccaccag aactccagct cctactacag ccacgcggca   1740
ggccagggca ccggcctcta ctccaccttc acctacatga accccgctca gcgccccatg   1800
tacaccccca tcgccgacac ctctggggtc ccttccatcc cgcagaccca cagcccccag   1860
cactgggaac aacccgtcta cacacagctc actcgacctt gaggaggcct cccacgaagg   1920
gcgaagatgg ccgagatgat cctaaaaata accgaagaaa gagaggacca accagaattc   1980
cctttggaca tttgtgtttt tttgtttttt tattttgttt tgtttttttct tcttcttctt   2040
cttccttaaa gacatttaag ctaaaggcaa ctcgtaccca aatttccaag acacaaacat   2100
gacctatcca agcgcattac ccacttgtgg ccaatcagtg gccaggccaa ccttggctaa   2160
atggagcagc gaaatcaacg agaaactgga ctttttaaac cctcttcaga gcaagcgtgg   2220
aggatgatgg agaatcgtgt gatcagtgtg ctaaatctct ctgcctgttt ggactttgta   2280
attatttttt tagcagtaat taaagaaaaa agtcctctgt gaggaatatt ctctatttta   2340
aatattttta gtatgtactg tgtatgattc attaccattt tgaggggatt tatacatatt   2400
tttagataaa attaaatgct cttatttttc caacagctaa actactctta gttgaacagt   2460
gtgccctagc ttttcttgca accagagtat ttttgtacag atttgctttc tcttacaaaa   2520
agaaaaaaaa aatcctgttg tattaacatt taaaaacaga attgtgttat gtgatcagtt   2580
ttgggggtta actttgctta attcctcagg ctttgcgatt taaggaggag ctgccttaaa   2640
aaaaaataaa ggccttattt tgcaattatg ggagtaaaca atagtctaga gaagcatttg   2700
gtaagcttta tcatatatat attttttaaa gaagagaaaa acaccttgag ccttaaaacg   2760
gtgctgctgg gaaacatttg cactctttta gtgcatttcc tcctgccttt gcttgttcac   2820
tgcagtctta agaaagaggt aaaaggcaag caaaggagat gaaatctgtt ctgggaatgt   2880
ttcagcagcc aataagtgcc cgagcacact gcccccggtt gcctgcctgg gccccatgtg   2940
gaaggcagat gcctgctcgc tctgtcacct gtgcctctca gaacaccagc agttaacctt   3000
caagacattc cacttgctaa aattatttat tttgtaagga gaggttttaa ttaaaacaaa   3060
```

```
aaaaaattct tttttttttt tttttccaat tttaccttct ttaaaatagg ttgttggagc   3120
tttcctcaaa gggtatggtc atctgttgtt aaattatgtt cttaactgta accagttttt   3180
ttttatttat ctctttaatc ttttttttatt attaaaagca agtttctttg tattcctcac   3240
cctagatttg tataaatgcc tttttgtcca tcccttttttt ctttgttgtt tttgttgaaa   3300
acaaactgga aacttgtttc tttttttgta taaatgagag attgcaaatg tagtgtatca   3360
ctgagtcatt tgcagtgttt tctgccacag acctttgggc tgccttatat tgtgtgtgtg   3420
tgtgggtgtg tgtgtgtttt gacacaaaaa caatgcaagc atgtgtcatc catatttctc   3480
tgcatcttct cttggagtga gggaggctac ctggagggga tcagcccact gacagacctt   3540
aatcttaatt actgctgtgg ctagagagtt tgaggattgc tttttaaaaa agacagcaaa   3600
cttttttttt tatttaaaaa aagatatatt aacagtttta gaagtcagta gaataaaatc   3660
ttaaagcact cataatatgg catccttcaa tttctgtata aaagcagatc tttttaaaaa   3720
gatacttctg taacttaaga aacctggcat ttaaatcata ttttgtcttt aggtaaaagc   3780
tttggtttgt gttcgtgttt tgtttgtttc acttgtttcc ctcccagccc caaacctttt   3840
gttctctccg tgaaacttac ctttcccttt ttctttctct tttttttttt tgtatattat   3900
tgtttacaat aaatatacat tgcattaaaa agaaaaaaaa aaaaaaaaaa aaaaaaaaaa   3960
aaa                                                                 3963
```

<210> SEQ ID NO 49
<211> LENGTH: 8840
<212> TYPE: DNA
<213> ORGANISM: Homo sapiens

<400> SEQUENCE: 49

```
cacctacctc cccgccgctc cagagggggc tcgcagagct gaggacgcgc gcagcgctgc     60
tcaaggtctc tctctctcag caccctcgcc ggccggcgtc tgacgcgggt gccagggtct    120
ccgggcacct ttcagtgtcc attccctcag ccagccagga ctccgcaacc cagcagttgc    180
cgctgcggcc acagcccgag gggacctgcg gacaggacgc cggcaggagg aggggtgcgc    240
agcgcccgcg cagagcgtct ccctcgctac gcagcgagac ccgggcctcc cggccccagg    300
agcccccagc tgcctcgcca ggtgtgtggg actgaagttc ttggagaagg gagtccaact    360
cttcaaggtg aactatgacc actttactct gggttttcgt gactctgagg gtcatcactg    420
cagctgtcac tgtagaaact tcagaccatg acaactcgct gagtgtcagc atccccccaac   480
cgtccccgct gagggtcctc ctggggacct ccctcaccat cccctgctat ttcatcgacc    540
ccatgcaccc tgtgaccacc gccccttcta ccgccccact ggccccaaga atcaagtgga    600
gccgtgtgtc caaggagaag gaggtagtgc tgctggtggc cactgaaggg cgcgtgcggg    660
tcaacagtgc ctatcaggac aaggtctcac tgcccaacta cccggccatc cccagtgacg    720
ccaccttgga agtccagagc ctgcgctcca atgactctgg ggtctaccgc tgcgaggtga    780
tgcatggcat cgaggacagc gaggccaccc tggaagtcgt ggtgaaaggc atcgtgttcc    840
attacagagc catctctaca cgctacaccc tcgactttga cagggcgcag cgggcctgcc    900
tgcagaacag tgccatcatt gccacgcctg agcagctgca ggccgcctac gaagacggct    960
tccaccagtg tgacgccggc tggctggctg accagactgt cagatacccc atccacactc   1020
cccgggaagg ctgctatgga gacaaggatg agtttcctgg tgtgaggacg tatggcatcc   1080
gagacaccaa cgagacctat gatgtgtact gcttcgccga ggagatggag ggtgaggtct   1140
tttatgcaac atctccagag aagttcacct tccaggaagc agccaatgag tgccggcggc   1200
```

-continued

```
tgggtgcccg gctggccacc acgggccagc tctacctggc ctggcaggct ggcatggaca   1260
tgtgcagcgc cggctggctg gccgaccgca gcgtgcgcta ccccatctcc aaggcccggc   1320
ccaactgcgg tggcaacctc ctgggcgtga ggaccgtcta cgtgcatgcc aaccagacgg   1380
gctaccccga cccctcatcc cgctacgacg ccatctgcta cacaggtgaa gactttgtgg   1440
acatcccaga aaacttcttt ggagtggggg gtgaggagga catcaccgtc cagacagtga   1500
cctggcctga catggagctg ccactgcctc gaaacatcac tgagggtgaa gcccgaggca   1560
gcgtgatcct taccgtaaag cccatcttcg aggtctcccc cagtcccctg gaacccgagg   1620
agcccttcac gtttgcccct gaaatagggg ccactgcctt cgctgaggtt gagaatgaga   1680
ctggagaggc caccaggccc tggggctttc ccacacctgg cctgggccct gccacggcat   1740
tcaccagtga ggacctcgtc gtgcaggtga ccgctgtccc tgggcagccg catttgccag   1800
ggggggtcgt cttccactac cgcccgggac ccacccgcta ctcgctgacc tttgaggagg   1860
cacagcaggc ctgcctgcgc acgggggcgg tcattgcctc gccggagcag ctccaggccg   1920
cctacgaagc aggctatgag cagtgtgacg ccggctggct gcgggaccag accgtcagat   1980
accccattgt gagcccccgg accccatgcg tgggtgacaa ggacagcagc ccaggggtca   2040
ggacctatgg cgtgcgccca tcaacagaga cctacgatgt ctactgcttt gtagacagac   2100
ttgaggggga ggtgttcttc gccacacgcc ttgagcagtt caccttccag gaagcactgg   2160
agttctgtga atctcacaat gctacgctgg ccaccacggg ccagctctac gccgcctgga   2220
gccgcggcct ggacaagtgc tatgccggct ggctggccga cggcagcctc cgctacccca   2280
tcgtcacccc aaggcctgcc tgcggtgggg acaagccagg cgtgagaacg gtctacctct   2340
accctaacca gacgggcctc ccagacccac tgtcccggca ccatgccttc tgcttccgag   2400
gcatttcagc ggttccttct ccaggagaag aagagggtgg cacacccaca tcaccctctg   2460
gtgtggagga gtggatcgtg acccaagtgg ttcctggtgt ggctgctgtc cccgtagaag   2520
aggagacaac tgctgtaccc tcaggggaga ctactgccat cctagagttc accaccgagc   2580
cagaaaacca gacagaatgg gaaccagcct ataccccagt gggcacatcc ccgctgccag   2640
ggatccttcc tacttggcct cccactggcg cagcaacaga ggaaagtaca gaaggccctt   2700
ctgcaactga agtgccctct gcctcagagg aaccatcccc ctcagaggtg ccattcccct   2760
cagaggagcc atccccctca gaggaaccat tcccctcagt gaggccattc ccctcagtgg   2820
agctgttccc ctcagaggag ccattcccct ccaaggagcc atccccctca gaggaaccat   2880
cagcctcgga agagccgtat acaccttcac cccccgtgcc cagctggact gagctgccca   2940
gctctgggga ggaatctggg gcccctgatg tcagtggtga cttcacaggc agtggagatg   3000
tttcaggaca ccttgacttc agtgggcagc tgtcagggga cagggcaagt ggactgccct   3060
ctggagacct ggactccagt ggtcttactt ccacagtggg ctcaggcctg cctgtggaaa   3120
gtggactacc ctcaggggat gaagagagaa ttgagtggcc cagcactcct acggttggtg   3180
aactgccctc tggagctgag atcctagagg gctctgcctc tggagttggg gatctcagtg   3240
gacttccttc tggagaagtt ctagagacct ctgcctctgg agtaggagac ctcagtgggc   3300
ttccttctgg agaagttcta gagaccactg cccctggagt agaggacatc agcgggcttc   3360
cttctggaga agttctagag accactgccc ctggagtaga ggacatcagc gggcttcctt   3420
ctggagaagt tctagagacc actgcccctg gagtagagga catcagcggg cttccttctg   3480
gagaagttct agagaccact gcccctggag tagaggacat cagcgggctt ccttctggag   3540
```

-continued

```
aagttctaga gaccactgcc cctggagtag aggacatcag cgggcttcct tctggagaag   3600
ttctagagac cactgcccct ggagtagagg acatcagcgg gcttccttct ggagaagttc   3660
tagagaccgc tgcccctgga gtagaggaca tcagcgggct tccttctgga gaagttctag   3720
agaccgctgc ccctggagta gaggacatca gcgggcttcc ttctggagaa gttctagaga   3780
ccgctgcccc tggagtagag gacatcagcg ggcttccttc tggagaagtt ctagagaccg   3840
ctgcccctgg agtagaggac atcagcgggc ttccttctgg agaagttcta gagaccgctg   3900
cccctggagt agaggacatc agcgggcttc cttctggaga agttctagag accgctgccc   3960
ctggagtaga ggacatcagc gggcttcctt ctggagaagt tctagagacc gctgcccctg   4020
gagtagagga catcagcggg cttccttctg gagaagttct agagactgct gcccctggag   4080
tagaggacat cagcgggctt ccttctggag aagttctaga gactgctgcc cctggagtag   4140
aggacatcag cgggcttcct tctggagaag ttctagagac tgctgcccct ggagtagagg   4200
acatcagcgg gcttccttct ggagaagttc tagagactgc tgcccctgga gtagaggaca   4260
tcagcgggct tccttctgga gaagttctag agactgctgc ccctggagta gaggacatca   4320
gcgggcttcc ttctggagaa gttctagaga ctgctgcccc tggagtagag gacatcagcg   4380
ggcttccttc tggagaagtt ctagagactg ctgcccctgg agtagaggac atcagcgggc   4440
ttccttctgg agaagttcta gagactgctg cccctggagt agaggacatc agcgggcttc   4500
cttctggaga agttctagag actgctgccc ctggagtaga ggacatcagc gggcttcctt   4560
ctggagaagt tctagagact actgcccctg gagtagagga gatcagcggg cttccttctg   4620
gagaagttct agagactact gcccctggag tagatgagat cagtgggctt ccttctggag   4680
aagttctaga gactactgcc cctggagtag aggagatcag cgggcttcct tctggagaag   4740
ttctagagac ttctacctct gcggtagggg acctcagtgg acttccttct ggaggagaag   4800
ttctagagat ttctgtctct ggagtagagg acatcagtgg gcttccttct ggagaggttg   4860
tagagacttc tgcctctgga atagaggatg tcagtgaact tccttcagga gaaggtctag   4920
agacctctgc ttctggagta gaggacctca gcaggctccc ttctggagaa gaagttctag   4980
agatttctgc ctctggattt ggggacctca gtggacttcc ttctggagga gaaggtctag   5040
agacctctgc ttctgaagta gggactgacc tcagtgggct tccttctgga agggagggtc   5100
tagagacttc agcttctgga gctgaggacc tcagtgggtt gccttctgga aaagaagact   5160
tggtggggtc agcttctgga gacttggact tgggcaaact gccttctgga actctaggaa   5220
gtgggcaagc tccagaaaca agtggtcttc cctctggatt tagtggtgag tattctgggg   5280
tggaccttgg aagtggccca ccctctggcc tgcctgactt tagtggactt ccatctggat   5340
tcccaactgt ttccctagtg gattctacat tggtggaagt ggtcacagcc tccactgcaa   5400
gtgaactgga agggagggga accattggca tcagtggtgc aggagaaata tctggactgc   5460
cctccagtga gctggacatt agtgggagag ctagtggact cccttcagga actgaactca   5520
gtggccaagc atctgggtct cctgatgtca gtggggaaat acctggactc tttggtgtca   5580
gtggacagcc atcagggttt cctgacacta gtggggaaac atctggagtg actgagctta   5640
gcgggctgtc ctctggacaa ccaggtatta gtggagaagc atctggagtt ctttatggca   5700
ctagtcaacc ctttggcata actgatctga gtggagaaac atctggggtc cctgatctca   5760
gtgggcagcc ttcagggtta ccagggttca gtggggcaac atcaggagtc cctgacctgg   5820
tttctggtac cacgagtggc agcggtgaat cttctgggat tacatttgtg gacaccagtt   5880
tggttgaagt ggcccctact acatttaaag aagaagaagg cttagggtct gtggaactca   5940
```

-continued

```
gtggcctccc ttccggagag gcagatctgt caggcaaatc tgggatggtg gatgtcagtg   6000
gacagttttc tggaacagtc gattccagtg ggtttacatc ccagactccg gaattcagtg   6060
gcctaccaag tggcatagct gaggtcagtg gagaatcctc cagagctgag attgggagca   6120
gcctgccctc gggagcatat tatggcagtg gaactccatc tagtttcccc actgtctctc   6180
ttgtagacag aactttggtg gaatctgtaa cccaggctcc aacagcccaa gaggcaggag   6240
aagggccttc tggcatttta gaactcagtg gtgctcattc tggagcacca gacatgtctg   6300
gggagcattc tggatttctg gacctaagtg ggctgcagtc cgggctgata gagcccagcg   6360
gagagccacc aggtactcca tattttagtg gggattttgc cagcaccacc aatgtaagtg   6420
gagaatcctc tgtagccatg ggcaccagtg gagaggcctc aggacttcca gaagttactt   6480
taatcacttc tgagttcgtg gagggtgtta ctgaaccaac tatttctcag gaactaggcc   6540
aaaggccccc tgtgacacac acaccccagc tttttgagtc cagtggaaaa gtctccacag   6600
ctggggacat tagtggagct accccagtgc tccctgggtc tggagtagaa gtatcatcag   6660
tcccagaatc tagcagtgag acgtccgcct atcctgaagc tgggttcggg gcatctgccg   6720
cccctgaggc cagcagagaa gattctgggt cccctgatct gagtgaaacc acctctgcat   6780
tccacgaagc taaccttgag agatcctctg gcctaggagt gagcggcagc actttgacat   6840
ttcaagaagg cgaggcgtcc gctgccccag aagtgagtgg agaatccacc accaccagtg   6900
atgtggggac agaggcacca ggcttgcctt cagccactcc cacggcttct ggagacagga   6960
ctgaaatcag cggagacctg tctggtcaca cctcgcagct gggcgttgtc atcagcacca   7020
gcatcccaga gtctgagtgg acccagcaga cccagcgccc tgcagagacg catctagaaa   7080
ttgagtcctc aagcctcctg tactcaggag aagagactca cacagtcgaa acagccacct   7140
ccccaacaga tgcttccatc ccagcttctc cggaatggaa acgtgaatca gaatcaactg   7200
ctgcagcccc cgccaggtcc tgtgcagagg agccctgtgg agctgggacc tgcaaggaga   7260
cagagggaca cgtcatatgc ctgtgccccc ctggctacac tggcgagcac tgtaacatag   7320
accaggaggt atgtgaggag ggctggaaca agtaccaggg ccactgttac cgccacttcc   7380
cggaccgcga gacctgggtg gatgctgagc gccggtgtcg ggagcagcag tcacacctga   7440
gcagcatcgt caccccccgag gagcaggagt ttgtcaacaa caatgcccaa gactaccagt   7500
ggatcggcct gaacgacagg accatcgaag gggacttccg ctggtcagat ggacacccca   7560
tgcaatttga gaactggcgc cccaaccagc ctgacaactt ttttgccgct ggagaggact   7620
gtgtggtgat gatctggcac gagaagggcg agtggaatga tgttccctgc aattaccacc   7680
tccccttcac gtgtaaaaag ggcacagtgg cctgcggaga gccccctgtg gtggagcatg   7740
ccaggacctt cgggcagaag aaggaccggt atgagatcaa ttccctggtg cggtaccagt   7800
gcacagaggg gtttgtccag cgccacatgc ccaccatccg gtgccagccc agcgggcact   7860
gggaggagcc tcagatcacc tgcacagacc ccaccaccta caaacgcaga ctacagaagc   7920
ggagctcacg gcaccctcgg aggagccgcc ccagcacagc ccactgagaa gagcttccag   7980
gacgcaccca ggacgctgag cccaggagcc tgccaggctg acgtgcatcc cacccagacg   8040
gtgtcctctt cttgtcgctt tttgtcatat aaggaatccc attaaagaag gaaaaaaata   8100
aatcccacat ttgtgtatgc acccactcac ccctccaaat cagcaaaacc gcatctaatt   8160
tgtccgccga atgccaaagc aaagcaaact tattataacc cttggactga gtttagagac   8220
atttcttcaa tttcccatcg tgcctttcca gggaccagtg cagggacagg gggagaaggg   8280
```

```
gaggggttaa gttaaataaa gaagattatt tttgtttcct gactttatcc aagagcagtg   8340

caatcgttgg ttatttcacc tccagggaga gctagggagg agggaggagg gctccaaagg   8400

agctggaagg agcagaggcc tgagagcagg aagaactcgg aaccgcagct gaatgtattg   8460

gatgagaagg agccaggagg gctacaccat ctgtatgagg gaaaagcctt gggggagagg   8520

ggtgggttcc tgcctcctgc cgagggtaag ccggcaggag agagccatca gagggacctc   8580

cgctgcctgg gagttgggtt ccctccaagg gtccctcttt cagtgtcctc tctctcacct   8640

gggtctgcca ccctaacagg tggcaactcg gcagggctgc tgggggcact tcctgcccag   8700

tggggggtgc cgcccaacct tctcccctcc ccaccccccgc ccccgggacc gtgcaggcac   8760

cagggttccg tgcacctatt tatatttttg aaaactgaag attataatat tataataata   8820

ataaagacat tggaagagat                                               8840
```

<210> SEQ ID NO 50
<211> LENGTH: 2471
<212> TYPE: DNA
<213> ORGANISM: Homo sapiens

<400> SEQUENCE: 50

```
agaaagcgag cagccaccca gctccccgcc accgccatgg tccccgacac cgcctgcgtt     60

cttctgctca ccctggctgc cctcggcgcg tccggacagg gccagagccc gttgggctca    120

gacctgggcc cgcagatgct tcgggaactg caggaaacca acgcggcgct gcaggacgtg    180

cgggagctgc tgcggcagca ggtcagggag atcacgttcc tgaaaaacac ggtgatggag    240

tgtgacgcgt gcgggatgca gcagtcagta cgcaccggcc tacccagcgt gcggcccctg    300

ctccactgcg cgcccggctt ctgcttcccc ggcgtggcct gcatccagac ggagagcggc    360

gcgcgctgcg gcccctgccc cgcgggcttc acgggcaacg gctcgcactg caccgacgtc    420

aacgagtgca acgcccaccc ctgcttcccc cgagtccgct gtatcaacac cagcccgggg    480

ttccgctgcg aggcttgccc gccggggtac agcggcccca cccaccaggg cgtggggctg    540

gctttcgcca aggccaacaa gcaggtttgc acggacatca acgagtgtga gaccgggcaa    600

cataactgcg tccccaactc cgtgtgcatc aacacccggg gctccttcca gtgcggcccg    660

tgccagcccg gcttcgtggg cgaccaggcg tccggctgcc agcggcgcgc acagcgcttc    720

tgccccgacg gctcgcccag cgagtgccac gagcatgcag actgcgtcct agagcgcgat    780

ggctcgcggt cgtgcgtgtg tgccgttggc tgggccggca acgggatcct ctgtggtcgc    840

gacactgacc tagacggctt cccggacgag aagctgcgct gcccggagcg ccagtgccgt    900

aaggacaact gcgtgactgt gcccaactca gggcaggagg atgtggaccg cgatggcatc    960

ggagacgcct gcgatccgga tgccgacggg gacggggtcc ccaatgaaaa ggacaactgc   1020

ccgctggtgc ggaacccaga ccagcgcaac acggacgagg acaagtgggg cgatgcgtgc   1080

gacaactgcc ggtcccagaa gaacgacgac caaaaggaca cagaccagga cggccggggc   1140

gatgcgtgcg acgacgacat cgacggcgac cggatccgca accaggccga caactgccct   1200

agggtaccca actcagacca gaaggacagt gatggcgatg gtatagggga tgcctgtgac   1260

aactgtcccc agaagagcaa cccggatcag gcggatgtgg accacgactt tgtgggagat   1320

gcttgtgaca gcgatcaaga ccaggatgga gacggacatc aggactctcg ggacaactgt   1380

cccacggtgc ctaacagtgc ccaggaggac tcagaccacg atggccaggg tgatgcctgc   1440

gacgacgacg acgacaatga cggagtccct gacagtcggg acaactgccg cctggtgcct   1500

aaccccggcc aggaggacgc ggacagggac ggcgtgggcg acgtgtgcca ggacgacttt   1560
```

```
gatgcagaca aggtggtaga caagatcgac gtgtgtccgg agaacgctga agtcacgctc   1620

accgacttca gggccttcca gacagtcgtg ctggacccgg agggtgacgc gcagattgac   1680

cccaactggg tggtgctcaa ccagggaagg gagatcgtgc agacaatgaa cagcgaccca   1740

ggcctggctg tgggttacac tgccttcaat ggcgtggact tcgagggcac gttccatgtg   1800

aacacggtca cggatgacga ctatgcgggc ttcatctttg gctaccagga cagctccagc   1860

ttctacgtgg tcatgtggaa gcagatggag caaacgtatt ggcaggcgaa ccccttccgt   1920

gctgtggccg agcctggcat ccaactcaag gctgtgaagt cttccacagg ccccggggaa   1980

cagctgcgga acgctctgtg gcatacagga gacacagagt cccaggtgcg gctgctgtgg   2040

aaggacccgc gaaacgtggg ttggaaggac aagaagtcct atcgttggtt cctgcagcac   2100

cggccccaag tgggctacat cagggtgcga ttctatgagg gccctgagct ggtggccgac   2160

agcaacgtgg tcttggacac aaccatgcgg ggtggccgcc tgggggtctt ctgcttctcc   2220

caggagaaca tcatctgggc caacctgcgt taccgctgca atgacaccat cccagaggac   2280

tatgagaccc atcagctgcg gcaagcctag ggaccagggt gaggacccgc cggatgacag   2340

ccaccctcac cgcggctgga tgggggctct gcacccagcc ccaaggggtg gccgtcctga   2400

gggggaagtg agaagggctc agagaggaca aaataaagtg tgtgtgcagg gaaaaaaaaa   2460

aaaaaaaaaa a                                                         2471
```

<210> SEQ ID NO 51
<211> LENGTH: 1892
<212> TYPE: DNA
<213> ORGANISM: Homo sapiens

<400> SEQUENCE: 51

```
ggcgcccgcg cccgcccccg cgccgggccc ggctcggccc gacccggctc cgccgcgggc     60

aggcggggcc cagcgcactc ggagcccgag cccgagccgc agccgccgcc tggggcgctt    120

gggtcggcct cgaggacacc ggagaggggc gccacgccgc cgtggccgca gatttgaaag    180

aagccaacac taaaccacaa atatacaaca aggccatttt ctcaaacgag agtcagcctt    240

taacgaaatg accatggttg acacagagat gccattctgg cccaccaact ttgggatcag    300

ctccgtggat ctctccgtaa tggaagacca ctcccactcc tttgatatca agcccttcac    360

tactgttgac ttctccagca tttctactcc acattacgaa gacattccat tcacaagaac    420

agatccagtg gttgcagatt acaagtatga cctgaaactt caagagtacc aaagtgcaat    480

caaagtggag cctgcatctc caccttatta ttctgagaag actcagctct acaataagcc    540

tcatgaagag ccttccaact ccctcatggc aattgaatgt cgtgtctgtg gagataaagc    600

ttctggattt cactatggag ttcatgcttg tgaaggatgc aagggtttct tccggagaac    660

aatcagattg aagcttatct atgacagatg tgatcttaac tgtcggatcc acaaaaaaag    720

tagaaataaa tgtcagtact gtcggtttca gaaatgcctt gcagtgggga tgtctcataa    780

tgccatcagg tttgggcgga tgccacaggc cgagaaggag aagctgttgg cggagatctc    840

cagtgatatc gaccagctga atccagagtc cgctgacctc cgggccctgg caaaacattt    900

gtatgactca tacataaagt ccttcccgct gaccaaagca aaggcgaggg cgatcttgac    960

aggaaagaca acagacaaat caccattcgt tatctatgac atgaattcct taatgatggg   1020

agaagataaa atcaagttca aacacatcac ccccctgcag gagcagagca aagaggtggc   1080

catccgcatc tttcagggct gccagtttcg ctccgtggag gctgtgcagg agatcacaga   1140
```

```
gtatgccaaa agcattcctg gttttgtaaa tcttgacttg aacgaccaag taactctcct   1200
caaatatgga gtccacgaga tcatttacac aatgctggcc tccttgatga ataaagatgg   1260
ggttctcata tccgagggcc aaggcttcat gacaagggag tttctaaaga gcctgcgaaa   1320
gccttttggt gactttatgg agcccaagtt tgagtttgct gtgaagttca atgcactgga   1380
attagatgac agcgacttgg caatatttat tgctgtcatt attctcagtg gagaccgccc   1440
aggtttgctg aatgtgaagc ccattgaaga cattcaagac aacctgctac aagccctgga   1500
gctccagctg aagctgaacc accctgagtc ctcacagctg tttgccaagc tgctccagaa   1560
aatgacagac ctcagacaga ttgtcacgga acacgtgcag ctactgcagg tgatcaagaa   1620
gacggagaca gacatgagtc ttcacccgct cctgcaggag atctacaagg acttgtacta   1680
gcagagagtc ctgagccact gccaacattt cccttcttcc agttgcacta ttctgaggga   1740
aaatctgaca cctaagaaat ttactgtgaa aaagcatttt aaaaagaaaa ggttttagaa   1800
tatgatctat tttatgcata ttgtttataa agacacattt acaatttact tttaatatta   1860
aaaattacca tattatgaaa ttgctgatag ta                                 1892
```

<210> SEQ ID NO 52
<211> LENGTH: 3747
<212> TYPE: DNA
<213> ORGANISM: Homo sapiens

<400> SEQUENCE: 52

```
aaatttttcc gtctgccctt tccccctctt ctcgttggca gggttgatcc tcattactgt     60
ttgctcaaac gtttagaagt gaatttaggt ccctcccccc aacttatgat tttatagcca    120
ataggtgatg aggtttattt gcatatttcc agtcacataa gcagccttgg cgtgaaaaca    180
gtgtcagact cgattccccc tcttcctcct cctcaaggga aagctgccca cttctagctg    240
ccctgccatc ccctttaaag ggcgacttgc tcagcgccaa accgcggctc cagccctctc    300
cagcctccgg ctcagccggc tcatcagtcg gtccgcgcct tgcagctcct ccagagggac    360
gcgccccgag atggagagca aagccctgct cgtgctgact ctggccgtgt ggctccagag    420
tctgaccgcc tcccgcggag gggtggccgc cgccgaccaa agaagagatt ttatcgacat    480
cgaaagtaaa tttgccctaa ggacccctga agacacagct gaggacactt gccacctcat    540
tcccggagta gcagagtccg tggctacctg tcatttcaat cacagcagca aaaccttcat    600
ggtgatccat ggctggacgg taacaggaat gtatgagagt tgggtgccaa aacttgtggc    660
cgccctgtac aagagagaac cagactccaa tgtcattgtg gtggactggc tgtcacgggc    720
tcaggagcat tacccagtgt ccgcgggcta caccaaactg gtgggacagg atgtggcccg    780
gtttatcaac tggatggagg aggagtttaa ctaccctctg gacaatgtcc atctcttggg    840
atacagcctt ggagcccatg ctgctggcat tgcaggaagt ctgaccaata agaaagtcaa    900
cagaattact ggcctcgatc cagctggacc taactttgag tatgcagaag ccccgagtcg    960
tctttctcct gatgatgcag attttgtaga cgtcttacac acattcacca gagggtcccc   1020
tggtcgaagc attggaatcc agaaaccagt tgggcatgtt gacatttacc cgaatggagg   1080
tacttttcag ccaggatgta acattggaga agctatccgc gtgattgcag agagaggact   1140
tggagatgtg gaccagctag tgaagtgctc ccacgagcgc tccattcatc tcttcatcga   1200
ctctctgttg aatgaagaaa atccaagtaa ggcctacagg tgcagttcca aggaagcctt   1260
tgagaaaggg ctctgcttga gttgtagaaa gaaccgctgc aacaatctgg gctatgagat   1320
caataaagtc agagccaaaa gaagcagcaa aatgtacctg aagactcgtt ctcagatgcc   1380
```

-continued

```
ctacaaagtc ttccattacc aagtaaagat tcatttttct gggactgaga gtgaaaccca   1440
taccaatcag gcctttgaga tttctctgta tggcaccgtg gccgagagtg agaacatccc   1500
attcactctg cctgaagttt ccacaaataa gacctactcc ttcctaattt acacagaggt   1560
agatattgga gaactactca tgttgaagct caaatggaag agtgattcat actttagctg   1620
gtcagactgg tggagcagtc ccggcttcgc cattcagaag atcagagtaa aagcaggaga   1680
gactcagaaa aaggtgatct tctgttctag ggagaaagtg tctcatttgc agaaaggaaa   1740
ggcacctgcg gtatttgtga aatgccatga caagtctctg aataagaagt caggctgaaa   1800
ctgggcgaat ctacagaaca aagaacggca tgtgaattct gtgaagaatg aagtggagga   1860
agtaactttt acaaaacata cccagtgttt ggggtgtttc aaaagtggat tttcctgaat   1920
attaatccca gccctaccct tgttagttat tttaggagac agtctcaagc actaaaaagt   1980
ggctaattca atttatgggg tatagtggcc aaatagcaca tcctccaacg ttaaaagaca   2040
gtggatcatg aaaagtgctg ttttgtcctt tgagaaagaa ataattgttt gagcgcagag   2100
taaaataagg ctccttcatg tggcgtattg ggccatagcc tataattggt tagaacctcc   2160
tattttaatt ggaattctgg atctttcgga ctgaggcctt ctcaaacttt actctaagtc   2220
tccaagaata cagaaaatgc ttttccgcgg cacgaatcag actcatctac acagcagtat   2280
gaatgatgtt ttagaatgat tccctcttgc tattggaatg tggtccagac gtcaaccagg   2340
aacatgtaac ttggagaggg acgaagaaag ggtctgataa acacagaggt tttaaacagt   2400
ccctaccatt ggcctgcatc atgacaaagt tacaaattca aggagatata aaatctagat   2460
caattaattc ttaataggct ttatcgttta ttgcttaatc cctctctccc ccttcttttt   2520
tgtctcaaga ttatattata ataatgttct ctgggtaggt gttgaaaatg agcctgtaat   2580
cctcagctga cacataattt gaatggtgca gaaaaaaaaa aagaaaccgt aattttatta   2640
ttagattctc caaatgattt tcatcaattt aaaatcattc aatatctgac agttactctt   2700
cagttttagg cttaccttgg tcatgcttca gttgtacttc cagtgcgtct cttttgttcc   2760
tggctttgac atgaaaagat aggtttgagt tcaaattttg cattgtgtga gcttctacag   2820
attttagaca aggaccgttt ttactaagta aaagggtgga gaggttcctg gggtggattc   2880
ctaagcagtg cttgtaaacc atcgcgtgca atgagccaga tggagtacca tgagggttgc   2940
tatttgttgt ttttaacaac taatcaagag tgagtgaaca actatttata aactagatct   3000
cctatttttc agaatgctct tctacgtata aatatgaaat gataaagatg tcaaatatct   3060
cagaggctat agctgggaac ccgactgtga aagtatgtga tatctgaaca catactagaa   3120
agctctgcat gtgtgttgtc cttcagcata attcggaagg gaaaacagtc gatcaaggga   3180
tgtattggaa catgtcggag tagaaattgt tcctgatgtg ccagaacttc gaccctttct   3240
ctgagagaga tgatcgtgcc tataaatagt aggaccaatg ttgtgattaa catcatcagg   3300
cttggaatga attctctcta aaaataaaat gatgtatgat ttgttgttgg catcccttt   3360
attaattcat taaatttctg gatttgggtt gtgacccagg gtgcattaac ttaaaagatt   3420
cactaaagca gcacatagca ctgggaactc tggctccgaa aaactttgtt atatatatca   3480
aggatgttct ggctttacat tttatttatt agctgtaaat acatgtgtgg atgtgtaaat   3540
ggagcttgta catattggaa aggtcattgt ggctatctgc atttataaat gtgtggtgct   3600
aactgtatgt gtctttatca gtgatggtct cacagagcca actcactctt atgaaatggg   3660
ctttaacaaa acaagaaaga aacgtactta actgtgtgaa gaaatggaat cagcttttaa   3720
```

```
taaaattgac aacattttat taccaca                                        3747


<210> SEQ ID NO 53
<211> LENGTH: 4629
<212> TYPE: DNA
<213> ORGANISM: Homo sapiens

<400> SEQUENCE: 53

aggctgttga ggctgggcca tctcctcctc acttccattc tgactgcagt ctgtggttct      60

gattccatac cagaggagac gggatttcac catgttgtcc aggctggtct gaaactcctg     120

acatcagggc tcaggatgct gttgctggga gctgttctac tgctattagc tctgcccggt     180

catgaccagg aaaccacgac tcaagggccc ggagtcctgc ttcccctgcc caagggggcc     240

tgcacaggtt ggatggcggg catcccaggg catccgggcc ataatggggc cccaggccgt     300

gatggcagag atggcacccc tggtgagaag ggtgagaaag gagatccagg tcttattggt     360

cctaagggag acatcggtga aaccggagta cccggggctg aaggtccccg aggctttccg     420

ggaatccaag gcaggaaagg agaacctgga gaaggtgcct atgtataccg ctcagcattc     480

agtgtgggat tggagactta cgttactatc cccaacatgc ccattcgctt taccaagatc     540

ttctacaatc agcaaaacca ctatgatggc tccactggta aattccactg caacattcct     600

gggctgtact actttgccta ccacatcaca gtctatatga aggatgtgaa ggtcagcctc     660

ttcaagaagg acaaggctat gctcttcacc tatgatcagt accaggaaaa taatgtggac     720

caggcctccg gctctgtgct cctgcatctg gaggtgggcg accaagtctg gctccaggtg     780

tatggggaag gagagcgtaa tggactctat gctgataatg acaatgactc caccttcaca     840

ggctttcttc tctaccatga caccaactga tcaccactaa ctcagagcct cctccaggcc     900

aaacagcccc aaagtcaatt aaaggctttc agtacggtta ggaagttgat tattatttag     960

ttggaggcct ttagatatta ttcattcatt tactcattca tttattcatt cattcatcga    1020

gtaactttaa aaaaatcata tgctatgttc ccagtcctgg ggagcttcac aaacatgacc    1080

agataactga ctagaaagaa gtagttgaca gtgctatttt gtgcccactg tctctcctga    1140

tgctcatatc aatcctataa ggcacaggga acaagcattc tcctgttttt acagattgta    1200

tcctgaggct gagagagtta agtgaatgtc taaggtcaca cagtattaag tgacagtgct    1260

agaaatcaaa cccagagctg tggactttgt tcactagact gtgccctttt atagaggtac    1320

atgttctctt tggagtgttg gtaggtgtct gtttcccacc tcacctgaga gccattgaat    1380

ttgccttcct catgaattaa aacctccccc aagcagagct tcctcagaga aagtggttct    1440

atgatgacgt cctgtcttgg aaggactact actcaatggc ccctgcacta ctctacttcc    1500

tcttacctat gtcccttctc atgcctttcc ctccaacggg gaaagccaac tccatctcta    1560

agtgccgaac tcatccctgt tcctcaaggc cacctggcca ggagcttctc tgatgtgata    1620

tccacttttt tttttttga gatggagtct cactctgtca cccaggctgg agtacagtga    1680

cacgacctcg gctcactgca gcctccttct cctgggtcca agcaattatt gtgcctcagc    1740

ctcccgagta gctgagactt caggtgcatt ccaccacaca tggctaattt ttgtattttt    1800

agtagaaatg gggtttcgtc atgttggcca ggctggtctc gaactcctgg cctaggtgat    1860

ccacccgcct cgacctccca aagtgctggg attacaggca tgagccacca tgcccagtcg    1920

atatctcact ttttattttg ccatggatga gagtcctggg tgtgaggaac acctcccacc    1980

aggctagagg caactgccca ggaaggactg tgcttccgtc acctctaaat cccttgcaga    2040

tccttgataa atgcctcatg aagaccaatc tcttgaatcc catatctacc cagaattaac    2100
```

-continued

```
tccattccag tctctgcatg taatcagttt tatccacaga aacattttca ttttaggaaa   2160
tccctggttt taagtatcaa tccttgttca gctggacaat atgaatcttt tccactgaag   2220
ttagggatga ctgtgatttt cagaacacgt ccagaatttt tcatcaagaa ggtagcttga   2280
gcctgaaatg caaaacccat ggaggaattc tgaagccatt gtctccttga gtaccaacag   2340
ggtcagggaa gactgggcct cctgaattta ttattgttct ttaagaatta caggttgagg   2400
tagttgatgg tggtaaacat tctctcagga gacaataact ccagtgatgt tcttcaaaga   2460
ttttagcaaa aacagagtaa atagcattct ctatcaatat ataaatttaa aaaactatct   2520
ttttgcttac agttttaaat tctgaacaat tctctcttat atgtgtattg ctaatcatta   2580
aggtattatt ttttccacat ataaagcttt gtctttttgt tgttgttgtt gtttttaaga   2640
tggagtttcc ctctgttgcc aggctagagt gcagtggcat gatctcggct tactgcaacc   2700
tttgcctccc aggttcaagc gattcttctg cctcagcctc ccgagtagct gggaccacag   2760
gtgcctacca ccatgccagg ctaatttttg tatttttagt aaagacaggg tttcaccata   2820
ttggccaggc tggtctcgaa ctcctgacct tgtgatctgc ccgcctccat ttttgttgtt   2880
attttttgag aaagatagat atgaggttta gagagggatg aagaggtgag agtaagcctt   2940
gtgttagtca gaactctgtg ttgtgaatgt cattcacaac agaaaaccca aaatattatg   3000
caaactactg taagcaagaa aaataaagga aaaatggaaa catttattcc tttgcataat   3060
agaaattacc agagttgttc tgtctttaga taaggtttga accaaagctc aaaacaatca   3120
agaccctttt ctgtatgtcc ttctgttctg ccttccgcag tgtaggcttt accctcaggt   3180
gctacacagt atagttctag ggtttccctc ccgatatcaa aaagactgtg gcctgcccag   3240
ctctcgtatc cccaagccac accatctggc taaatggaca tcatgttttc tggtgatgcc   3300
caaagaggag agaggaagct ctctttccca gatgccccag caagtgtaac cttgcatctc   3360
attgctctgg ctgagttgtg tgcctgtttc tgaccaatca ctgagtcagg aggatgaaat   3420
attcatattg acttaattgc agcttaagtt aggggtatgt agaggtattt tccctaaagc   3480
aaaattggga cactgttatc agaaatagga gagtggatga tagatgcaaa ataatacctg   3540
tccacaacaa actcttaatg ctgtgtttga gctttcatga gtttcccaga gagacatagc   3600
tggaaaattc ctattgattt tctctaaaat ttcaacaagt agctaaagtc tggctatgct   3660
cacagtctca catctggttg gggtgggctc cttacagaac acgctttcac agttacccta   3720
aactctctgg ggcagggtta ttcctttgtg gaaccagagg cacagagaga gtcaactgag   3780
gccaaaagag gcctgagaga aactgaggtc aagatttcag gattaatggt cctgtgatgc   3840
tttgaagtac aattgtggat ttgtccaatt ctctttagtt ctgtcagctt ttgcttcata   3900
tattttagcg ctctattatt agatatatac atgtttagta ttatgtctta ttggtgcatt   3960
tactctctta tcattatgta atgtccttct ttatctgtga taattttctg tgttctgaag   4020
tctactttgt ctaaaaataa catacgcact caacttcctt ttctttcttc cttcctttct   4080
ttcttccttc ctttctttct ctctctctct ctttccttcc ttccttcctc cttttctttc   4140
tctctctctc tctctctctt tttttgacag actctcgttc tgtggccctg gctggagttc   4200
agtggtgtga tcttggctca ctgctacctc taccatgagc aattctcctg cctcagcctc   4260
ccaagtagct ggaactacag gctcatgcca ctgcgcccag ctaatttttg tatttttcgt   4320
agagacgggg tttcaccaca ttcgtcaggt tggtttcaaa ctcctgactt tgtgatccac   4380
ccgcctcggc ctcccaaagt gctgggatta caggcatgag ccatcacacc tggtcaactt   4440
```

```
tcttttgatt agtgtttttg tggtatatct ttttccatca tgttacttta aatatatcta   4500

tattattgta tttaaaatgt gtttcttaca gactgcatgt agttgggtat aatttttatc   4560

cagtctaaaa atatctgtct tttaattggt gtttagacaa tttatattta ataaaattgt   4620

tgaatttaa                                                          4629


<210> SEQ ID NO 54
<211> LENGTH: 3444
<212> TYPE: DNA
<213> ORGANISM: Homo sapiens

<400> SEQUENCE: 54

gtaggaatcg cagcgccagc ggttgcaagg cccaagaagc ccatcctggg aaggaaaatg     60

cattggggaa ccctgtgcgg attcttgtgg ctttggccct atcttttcta tgtccaagct    120

gtgcccatcc aaaaagtcca agatgacacc aaaaccctca tcaagacaat tgtcaccagg    180

atcaatgaca tttcacacac gcagtcagtc tcctccaaac agaaagtcac cggtttggac    240

ttcattcctg ggctccaccc catcctgacc ttatccaaga tggaccagac actggcagtc    300

taccaacaga tcctcaccag tatgccttcc agaaacgtga tccaaatatc caacgacctg    360

gagaacctcc gggatcttct tcacgtgctg gccttctcta agagctgcca cttgccctgg    420

gccagtggcc tggagacctt ggacagcctg gggggtgtcc tggaagcttc aggctactcc    480

acagaggtgg tggccctgag caggctgcag gggtctctgc aggacatgct gtggcagctg    540

gacctcagcc ctgggtgctg aggccttgaa ggtcactctt cctgcaagga ctacgttaag    600

ggaaggaact ctggcttcca ggtatctcca ggattgaaga gcattgcatg gacacccctt    660

atccaggact ctgtcaattt ccctgactcc tctaagccac tcttccaaag gcataagacc    720

ctaagcctcc ttttgcttga aaccaaagat atatacacag gatcctattc tcaccaggaa    780

gggggtccac ccagcaaaga gtgggctgca tctgggattc ccaccaaggt cttcagccat    840

caacaagagt tgtcttgtcc cctcttgacc catctccccc tcactgaatg cctcaatgtg    900

accaggggtg atttcagaga gggcagaggg gtaggcagag cctttggatg accagaacaa    960

ggttccctct gagaattcca aggagttcca tgaagaccac atccacacac gcaggaactc   1020

ccagcaacac aagctggaag cacatgttta tttattctgc attttattct ggatggattt   1080

gaagcaaagc accagcttct ccaggctctt tggggtcagc cagggccagg ggtctccctg   1140

gagtgcagtt tccaatccca tagatgggtc tggctgagct gaacccattt tgagtgactc   1200

gagggttggg ttcatctgag caagagctgg caaaggtggc tctccagtta gttctctcgt   1260

aactggtttc atttctactg tgactgatgt tacatcacag tgtttgcaat ggtgttgccc   1320

tgagtggatc tccaaggacc aggttatttt aaaaagattt gttttgtcaa gtgtcatatg   1380

taggtgtctg cacccagggg tggggaatgt ttgggcagaa gggagaagga tctagaatgt   1440

gttttctgaa taacatttgt gtggtgggtt ctttggaagg agtgagatca ttttcttatc   1500

ttctgcaatt gcttaggatg tttttcatga aaatagctct ttcagggggg ttgtgaggcc   1560

tggccaggca ccccctggag agaagtttct ggccctggct gaccccaaag agcctggaga   1620

agctgatgct ttgcttcaaa tccatccaga ataaaacgca aagggctgaa agccatttgt   1680

tggggcagtg gtaagctctg gctttctccg actgctaggg agtggtcttt cctatcatgg   1740

agtgacggtc ccacactggt gactgcgatc ttcagagcag ggtccttgg tgtgaccctc   1800

tgaatggtcc agggttgatc acactctggg tttattacat ggcagtgttc ctatttgggg   1860

cttgcatgcc aaattgtagt tcttgtctga ttggctcacc caagcaaggc caaaattacc   1920
```

aaaaatcttg gggggttttt actccagtgg tgaagaaaac tcctttagca ggtggtcctg 1980
agacctgaca agcactgcta ggcgagtgcc aggactcccc aggccaggcc accaggatgg 2040
cccttcccac tggaggtcac attcaggaag atgaaagagg aggtttgggg tctgccacca 2100
tcctgctgct gtgtttttgc tatcacacag tgggtggtgg atctgtccaa ggaaacttga 2160
atcaaagcag ttaactttaa gactgagcac ctgcttcatg ctcagccctg actggtgcta 2220
taggctggag aagctcaccc aataaacatt aagattgagg cctgccctca gggatcttgc 2280
attcccagtg gtcaaaccgc actcacccat gtgccaaggt ggggtattta ccacagcagc 2340
tgaacagcca aatgcatggt gcagttgaca gcaggtggga aatggtatga gctgaggggg 2400
gccgtgccca ggggcccaca gggaaccctg cttgcacttt gtaacatgtt tacttttcag 2460
ggcatcttag cttctattat agccacatcc ctttgaaaca agataactga gaatttaaaa 2520
ataagaaaat acataagacc ataacagcca acaggtggca ggaccaggac tatagcccag 2580
gtcctctgat acccagagca ttacgtgagc caggtaatga gggactggaa ccagggagac 2640
cgagcgcttt ctggaaaaga ggagtttcga ggtagagttt gaaggaggtg agggatgtga 2700
attgcctgca gagagaagcc tgttttgttg gaaggtttgg tgtgtggaga tgcagaggta 2760
aaagtgtgag cagtgagtta cagcgagagg cagagaaaga agagacagga gggcaagggc 2820
catgctgaag ggaccttgaa gggtaaagaa gtttgatatt aaaggagtta agagtagcaa 2880
gttctagaga agaggctggt gctgtggcca gggtgagagc tgctctggaa aatgtgaccc 2940
agatcctcac aaccacctaa tcaggctgag gtgtcttaag ccttttgctc acaaaacctg 3000
gcacaatggc taattcccag agtgtgaaac ttcctaagta taaatggttg tctgtttttg 3060
taacttaaaa aaaaaaaaaa aagtttggcc gggtgcggtg gctcacgcct gtaatcccag 3120
cactttggga ggccaaggtg gggggatcac aaggtcacta gatggcgagc atcctggcca 3180
acatggtgaa accccgtctc tactaaaaac acaaaagtta gctgagcgtg gtggcgggcg 3240
cctgtagtcc cagccactcg ggaggctgag acaggagaat cgcttaaacc tgggaggcgg 3300
agagtacagt gagccaagat cgcgccactg cactccggcc tgatgacaga gcgagattcc 3360
gtcttaaaaa aaaaaaaaaa aaagtttgtt tttaaaaaaa tctaaataaa ataactttgc 3420
cccctgcaaa aaaaaaaaaa aaaa 3444

<210> SEQ ID NO 55
<211> LENGTH: 1818
<212> TYPE: DNA
<213> ORGANISM: Homo sapiens

<400> SEQUENCE: 55
ggcgcccgcg cccgcccccg cgccgggccc ggctcggccc gacccggctc cgccgcgggc 60
aggcggggcc cagcgcactc ggagcccgag cccgagccgc agccgccgcc tggggcgctt 120
gggtcggcct cgaggacacc ggagaggggc gccacgccgc cgtggccgca gaaatgacca 180
tggttgacac agagatgcca ttctggccca ccaactttgg gatcagctcc gtggatctct 240
ccgtaatgga agaccactcc cactcctttg atatcaagcc cttcactact gttgacttct 300
ccagcatttc tactccacat tacgaagaca ttccattcac aagaacagat ccagtggttg 360
cagattacaa gtatgacctg aaacttcaag agtaccaaag tgcaatcaaa gtggagcctg 420
catctccacc ttattattct gagaagactc agctctacaa taagcctcat gaagagcctt 480
ccaactccct catggcaatt gaatgtcgtg tctgtggaga taaagcttct ggatttcact 540
atggagttca tgcttgtgaa ggatgcaagg gtttcttccg gagaacaatc agattgaagc 600
ttatctatga cagatgtgat cttaactgtc ggatccacaa aaaaagtaga aataaatgtc 660
agtactgtcg gtttcagaaa tgccttgcag tggggatgtc tcataatgcc atcaggtttg 720
ggcggatgcc acaggccgag aaggagaagc tgttggcgga gatctccagt gatatcgacc 780
agctgaatcc agagtccgct gacctccggg ccctggcaaa acatttgtat gactcataca 840
taaagtcctt cccgctgacc aaagcaaagg cgagggcgat cttgacagga aagacaacag 900
acaaatcacc attcgttatc tatgacatga attccttaat gatgggagaa gataaaatca 960
agttcaaaca catcaccccc ctgcaggagc agagcaaaga ggtggccatc cgcatctttc 1020
agggctgcca gtttcgctcc gtggaggctg tgcaggagat cacagagtat gccaaaagca 1080
ttcctggttt tgtaaatctt gacttgaacg accaagtaac tctcctcaaa tatggagtcc 1140
acgagatcat ttacacaatg ctggcctcct tgatgaataa agatggggtt ctcatatccg 1200
agggccaagg cttcatgaca agggagtttc taaagagcct gcgaaagcct tttggtgact 1260
ttatggagcc caagtttgag tttgctgtga agttcaatgc actggaatta gatgacagcg 1320
acttggcaat atttattgct gtcattattc tcagtggaga ccgcccaggt ttgctgaatg 1380
tgaagcccat tgaagacatt caagacaacc tgctacaagc cctggagctc cagctgaagc 1440
tgaaccaccc tgagtcctca cagctgtttg ccaagctgct ccagaaaatg acagacctca 1500
gacagattgt cacggaacac gtgcagctac tgcaggtgat caagaagacg gagacagaca 1560
tgagtcttca cccgctcctg caggagatct acaaggactt gtactagcag agagtcctga 1620
gccactgcca acatttccct tcttccagtt gcactattct gagggaaaat ctgacaccta 1680
agaaatttac tgtgaaaaag cattttaaaa agaaaaggtt ttagaatatg atctatttta 1740
tgcatattgt ttataaagac acatttacaa tttactttta atattaaaaa ttaccatatt 1800
atgaaattgc tgatagta 1818

<210> SEQ ID NO 56
<211> LENGTH: 1820
<212> TYPE: DNA
<213> ORGANISM: Homo sapiens

<400> SEQUENCE: 56
ttcaagtctt tttcttttaa cggattgatc ttttgctaga tagagacaaa atatcagtgt 60
gaattacagc aaacccctat tccatgctgt tatgggtgaa actctgggag attctcctat 120
tgacccagaa agcgattcct tcactgatac actgtctgca aacatatcac aagaaatgac 180
catggttgac acagagatgc cattctggcc caccaacttt gggatcagct ccgtggatct 240
ctccgtaatg gaagaccact cccactcctt tgatatcaag cccttcacta ctgttgactt 300
ctccagcatt tctactccac attacgaaga cattccattc acaagaacag atccagtggt 360
tgcagattac aagtatgacc tgaaacttca agagtaccaa agtgcaatca aagtggagcc 420
tgcatctcca ccttattatt ctgagaagac tcagctctac aataagcctc atgaagagcc 480
ttccaactcc ctcatggcaa ttgaatgtcg tgtctgtgga gataaagctt ctggatttca 540
ctatggagtt catgcttgtg aaggatgcaa gggtttcttc cggagaacaa tcagattgaa 600
gcttatctat gacagatgtg atcttaactg tcggatccac aaaaaaagta gaaataaatg 660
tcagtactgt cggtttcaga aatgccttgc agtggggatg tctcataatg ccatcaggtt 720
tgggcggatg ccacaggccg agaaggagaa gctgttggcg gagatctcca gtgatatcga 780
ccagctgaat ccagagtccg ctgacctccg ggccctggca aaacatttgt atgactcata 840

```
cataaagtcc ttcccgctga ccaaagcaaa ggcgagggcg atcttgacag gaaagacaac    900
agacaaatca ccattcgtta tctatgacat gaattcctta atgatgggag aagataaaat    960
caagttcaaa cacatcaccc ccctgcagga gcagagcaaa gaggtggcca tccgcatctt   1020
tcagggctgc cagtttcgct ccgtggaggc tgtgcaggag atcacagagt atgccaaaag   1080
cattcctggt tttgtaaatc ttgacttgaa cgaccaagta actctcctca aatatggagt   1140
ccacgagatc atttacacaa tgctggcctc cttgatgaat aaagatgggg ttctcatatc   1200
cgagggccaa ggcttcatga caagggagtt tctaaagagc ctgcgaaagc cttttggtga   1260
ctttatggag cccaagtttg agtttgctgt gaagttcaat gcactggaat tagatgacag   1320
cgacttggca atatttattg ctgtcattat tctcagtgga gaccgcccag gtttgctgaa   1380
tgtgaagccc attgaagaca ttcaagacaa cctgctacaa gccctggagc tccagctgaa   1440
gctgaaccac cctgagtcct cacagctgtt tgccaagctg ctccagaaaa tgacagacct   1500
cagacagatt gtcacggaac acgtgcagct actgcaggtg atcaagaaga cggagacaga   1560
catgagtctt cacccgctcc tgcaggagat ctacaaggac ttgtactagc agagagtcct   1620
gagccactgc caacatttcc cttcttccag ttgcactatt ctgagggaaa atctgacacc   1680
taagaaattt actgtgaaaa agcattttaa aaagaaaagg ttttagaata tgatctattt   1740
tatgcatatt gtttataaag acacatttac aatttacttt taatattaaa aattaccata   1800
ttatgaaatt gctgatagta                                               1820
```

<210> SEQ ID NO 57
<211> LENGTH: 1919
<212> TYPE: DNA
<213> ORGANISM: Homo sapiens

<400> SEQUENCE: 57

```
ttggtggaag gtgggtgtgt agtcgtggta ctttacgcct cggtgtttag ggaggagcct     60
aaggtaagga gtcagaaacg gggagtaacc gagctgcggc ttttatataa ggtcagtggt    120
aggtaaggaa ggggccttaa cctctgctgg tgaccagaag cctgcatttc tgcattctgc    180
ttaattccct ttccttagat ttgaaagaag ccaacactaa accacaaata tacaacaagg    240
ccattttctc aaacgagagt cagcctttaa cgaaatgacc atggttgaca cagagatgcc    300
attctggccc accaactttg ggatcagctc cgtggatctc tccgtaatgg aagaccactc    360
ccactccttt gatatcaagc ccttcactac tgttgacttc tccagcattt ctactccaca    420
ttacgaagac attccattca caagaacaga tccagtggtt gcagattaca agtatgacct    480
gaaacttcaa gagtaccaaa gtgcaatcaa agtggagcct gcatctccac cttattattc    540
tgagaagact cagctctaca ataagcctca tgaagagcct tccaactccc tcatggcaat    600
tgaatgtcgt gtctgtggag ataaagcttc tggatttcac tatggagttc atgcttgtga    660
aggatgcaag ggtttcttcc ggagaacaat cagattgaag cttatctatg acagatgtga    720
tcttaactgt cggatccaca aaaaaagtag aaataaatgt cagtactgtc ggtttcagaa    780
atgccttgca gtggggatgt ctcataatgc catcaggttt gggcggatgc cacaggccga    840
gaaggagaag ctgttggcgg agatctccag tgatatcgac cagctgaatc cagagtccgc    900
tgacctccgg gccctggcaa aacatttgta tgactcatac ataaagtcct tcccgctgac    960
caaagcaaag gcgagggcga tcttgacagg aaagacaaca gacaaatcac cattcgttat   1020
ctatgacatg aattccttaa tgatgggaga agataaaatc aagttcaaac acatcacccc   1080
```

-continued

```
cctgcaggag cagagcaaag aggtggccat ccgcatcttt cagggctgcc agtttcgctc   1140

cgtggaggct gtgcaggaga tcacagagta tgccaaaagc attcctggtt ttgtaaatct   1200

tgacttgaac gaccaagtaa ctctcctcaa atatggagtc cacgagatca tttacacaat   1260

gctggcctcc ttgatgaata aagatggggt tctcatatcc gagggccaag gcttcatgac   1320

aagggagttt ctaaagagcc tgcgaaagcc ttttggtgac tttatggagc ccaagtttga   1380

gtttgctgtg aagttcaatg cactggaatt agatgacagc gacttggcaa tatttattgc   1440

tgtcattatt ctcagtggag accgcccagg tttgctgaat gtgaagccca ttgaagacat   1500

tcaagacaac ctgctacaag ccctggagct ccagctgaag ctgaaccacc ctgagtcctc   1560

acagctgttt gccaagctgc tccagaaaat gacagacctc agacagattg tcacggaaca   1620

cgtgcagcta ctgcaggtga tcaagaagac ggagacagac atgagtcttc acccgctcct   1680

gcaggagatc tacaaggact tgtactagca gagagtcctg agccactgcc aacatttccc   1740

ttcttccagt tgcactattc tgagggaaaa tctgacacct aagaaattta ctgtgaaaaa   1800

gcattttaaa aagaaaaggt tttagaatat gatctatttt atgcatattg tttataaaga   1860

cacatttaca atttactttt aatattaaaa attaccatat tatgaaattg ctgatagta    1919
```

```
<210> SEQ ID NO 58
<211> LENGTH: 1892
<212> TYPE: DNA
<213> ORGANISM: Homo sapiens

<400> SEQUENCE: 58

ggcgcccgcg cccgcccccg cgccgggccc ggctcggccc gacccggctc cgccgcgggc     60

aggcggggcc cagcgcactc ggagcccgag cccgagccgc agccgccgcc tggggcgctt    120

gggtcggcct cgaggacacc ggagaggggc gccacgccgc cgtggccgca gatttgaaag    180

aagccaacac taaaccacaa atatacaaca aggccatttt ctcaaacgag agtcagcctt    240

taacgaaatg accatggttg acacagagat gccattctgg cccaccaact ttgggatcag    300

ctccgtggat ctctccgtaa tggaagacca ctcccactcc tttgatatca agcccttcac    360

tactgttgac ttctccagca tttctactcc acattacgaa gacattccat tcacaagaac    420

agatccagtg gttgcagatt acaagtatga cctgaaactt caagagtacc aaagtgcaat    480

caaagtggag cctgcatctc caccttatta ttctgagaag actcagctct acaataagcc    540

tcatgaagag ccttccaact ccctcatggc aattgaatgt cgtgtctgtg gagataaagc    600

ttctggattt cactatggag ttcatgcttg tgaaggatgc aagggtttct tccggagaac    660

aatcagattg aagcttatct atgacagatg tgatcttaac tgtcggatcc acaaaaaaag    720

tagaaataaa tgtcagtact gtcggtttca gaaatgcctt gcagtgggga tgtctcataa    780

tgccatcagg tttgggcgga tgccacaggc cgagaaggag aagctgttgg cggagatctc    840

cagtgatatc gaccagctga atccagagtc cgctgacctc cgggccctgg caaaacattt    900

gtatgactca tacataaagt ccttcccgct gaccaaagca aaggcgaggg cgatcttgac    960

aggaaagaca acagacaaat caccattcgt tatctatgac atgaattcct taatgatggg   1020

agaagataaa atcaagttca aacacatcac ccccctgcag gagcagagca aagaggtggc   1080

catccgcatc tttcagggct gccagtttcg ctccgtggag gctgtgcagg agatcacaga   1140

gtatgccaaa agcattcctg gttttgtaaa tcttgacttg aacgaccaag taactctcct   1200

caaatatgga gtccacgaga tcatttacac aatgctggcc tccttgatga ataaagatgg   1260

ggttctcata tccgagggcc aaggcttcat gacaagggag tttctaaaga gcctgcgaaa   1320
```

gccttttggt gactttatgg agcccaagtt tgagtttgct gtgaagttca atgcactgga 1380
attagatgac agcgacttgg caatatttat tgctgtcatt attctcagtg gagaccgccc 1440
aggtttgctg aatgtgaagc ccattgaaga cattcaagac aacctgctac aagccctgga 1500
gctccagctg aagctgaacc accctgagtc ctcacagctg tttgccaagc tgctccagaa 1560
aatgacagac ctcagacaga ttgtcacgga acacgtgcag ctactgcagg tgatcaagaa 1620
gacggagaca gacatgagtc ttcacccgct cctgcaggag atctacaagg acttgtacta 1680
gcagagagtc ctgagccact gccaacattt cccttcttcc agttgcacta ttctgaggga 1740
aaatctgaca cctaagaaat ttactgtgaa aaagcatttt aaaaagaaaa ggttttagaa 1800
tatgatctat tttatgcata ttgtttataa agacacattt acaatttact tttaatatta 1860
aaaattacca tattatgaaa ttgctgatag ta 1892

<210> SEQ ID NO 59
<211> LENGTH: 1837
<212> TYPE: DNA
<213> ORGANISM: Homo sapiens

<400> SEQUENCE: 59
gagccgcgca cgggactggg aaggggaccc acccgagggt ccagccacca gccccctcac 60
taatagcggc caccccggca gcggcggcag cagcagcagc gacgcagcgg cgacagctca 120
gagcagggag gccgcgccac ctgcgggccg gccggagcgg gcagccccag gccccctccc 180
cgggcacccg cgttcatgca acgcctggtg gcctgggacc cagcatgtct ccccctgccg 240
ccgccgccgc ctgcctttaa atccatggaa gtggccaact tctactacga ggcggactgc 300
ttggctgctg cgtacggcgg caaggcggcc cccgcggcgc cccccgcggc cagacccggg 360
ccgcgccccc ccgccggcga gctgggcagc atcggcgacc acgagcgcgc catcgacttc 420
agcccgtacc tggagccgct gggcgcgccg caggccccgg cgcccgccac ggccacggac 480
accttcgagg cggctccgcc cgcgcccgcc cccgcgcccg cctcctccgg gcagcaccac 540
gacttcctct ccgacctctt ctccgacgac tacgggggca agaactgcaa gaagccggcc 600
gagtacggct acgtgagcct ggggcgcctg gggggccgcca agggcgcgct gcaccccggc 660
tgcttcgcgc ccctgcaccc accgccccg ccgccgccgc cgcccgccga gctcaaggcg 720
gagccgggct tcgagcccgc ggactgcaag cggaaggagg aggccggggc gccgggcggc 780
ggcgcaggca tggcggcggg cttcccgtac gcgctgcgcg cttacctcgg ctaccaggcg 840
gtgccgagcg gcagcagcgg gagcctctcc acgtcctcct cgtccagccc gcccggcacg 900
ccgagccccg ctgacgccaa ggcgccccg accgcctgct acgcgggggc cgcgccggcg 960
ccctcgcagg tcaagagcaa ggccaagaag accgtggaca agcacagcga cgagtacaag 1020
atccggcgcg agcgcaacaa catcgccgtg cgcaagagcc gcgacaaggc caagatgcgc 1080
aacctggaga cgcagcacaa ggtcctggag ctcacggccg agaacgagcg gctgcagaag 1140
aaggtggagc agctgtcgcg cgagctcagc accctgcgga acttgttcaa gcagctgccc 1200
gagcccctgc tcgcctcctc cggccactgc tagcgcggcc cccgcgcgcg tccccctgcc 1260
ggccggggct gagactccgg ggagcgcccg cgcccgcgcc ctcgccccg cccccggcgg 1320 cgccggcaaa actttggcac tggggcactt ggcagcgcgg ggagcccgtc ggtaatttta 1380
atattttatt atatatatat atctatattt ttgtccaaac caaccgcaca tgcagatggg 1440
gctcccgccc gtggtgttat ttaaagaaga aacgtctatg tgtacagatg aatgataaac 1500
tctctgcttc tccctctgcc cctctccagg cgccggcggg cgggccggtt tcgaagttga 1560
tgcaatcggt ttaaacatgg ctgaacgcgt gtgtacacgg gactgacgca acccacgtgt 1620
aactgtcagc cgggccctga gtaatcgctt aaagatgttc ctacgggctt gttgctgttg 1680
atgttttgtt ttgttttgtt ttttggtctt tttttgtatt ataaaaaata atctatttct 1740
atgagaaaag aggcgtctgt atattttggg aatcttttcc gtttcaagca ttaagaacac 1800
ttttaataaa cttttttttg agaatggtta caaagcc 1837

<210> SEQ ID NO 60
<211> LENGTH: 4578
<212> TYPE: DNA
<213> ORGANISM: Homo sapiens

<400> SEQUENCE: 60
aggctgttga ggctgggcca tctcctcctc acttccattc tgactgcagt ctgtggttct 60
gattccatac cagaggggct caggatgctg ttgctgggag ctgttctact gctattagct 120
ctgcccggtc atgaccagga aaccacgact caagggcccg gagtcctgct tcccctgccc 180
aagggggcct gcacaggttg gatggcgggc atcccagggc atccgggcca taatggggcc 240
ccaggccgtg atggcagaga tggcacccct ggtgagaagg gtgagaaagg agatccaggt 300
cttattggtc ctaagggaga catcggtgaa accggagtac ccggggctga aggtccccga 360
ggctttccgg gaatccaagg caggaaagga gaacctggag aaggtgccta tgtataccgc 420
tcagcattca gtgtgggatt ggagacttac gttactatcc ccaacatgcc cattcgcttt 480
accaagatct tctacaatca gcaaaaccac tatgatggct ccactggtaa attccactgc 540
aacattcctg ggctgtacta ctttgcctac cacatcacag tctatatgaa ggatgtgaag 600
gtcagcctct tcaagaagga caaggctatg ctcttcacct atgatcagta ccaggaaaat 660
aatgtggacc aggcctccgg ctctgtgctc ctgcatctgg aggtgggcga ccaagtctgg 720
ctccaggtgt atggggaagg agagcgtaat ggactctatg ctgataatga caatgactcc 780
accttcacag gctttcttct ctaccatgac accaactgat caccactaac tcagagcctc 840
ctccaggcca aacagcccca aagtcaatta aaggctttca gtacggttag gaagttgatt 900
attatttagt tggaggcctt tagatattat tcattcattt actcattcat ttattcattc 960
attcatcgag taactttaaa aaaatcatat gctatgttcc cagtcctggg gagcttcaca 1020
aacatgacca gataactgac tagaaagaag tagttgacag tgctattttg tgcccactgt 1080
ctctcctgat gctcatatca atcctataag gcacagggaa caagcattct cctgttttta 1140
cagattgtat cctgaggctg agagagttaa gtgaatgtct aaggtcacac agtattaagt 1200
gacagtgcta gaaatcaaac ccagagctgt ggactttgtt cactagactg tgccctttta 1260
tagaggtaca tgttctcttt ggagtgttgg taggtgtctg tttcccacct cacctgagag 1320
ccattgaatt tgccttcctc atgaattaaa acctccccca agcagagctt cctcagagaa 1380
agtggttcta tgatgacgtc ctgtcttgga aggactacta ctcaatggcc cctgcactac 1440
tctacttcct cttacctatg tcccttctca tgcctttccc tccaacgggg aaagccaact 1500
ccatctctaa gtgccgaact catccctgtt cctcaaggcc acctggccag gagcttctct 1560
gatgtgatat ccactttttt tttttttgag atggagtctc actctgtcac ccaggctgga 1620
gtacagtgac acgacctcgg ctcactgcag cctccttctc ctgggtccaa gcaattattg 1680
tgcctcagcc tcccgagtag ctgagacttc aggtgcattc caccacacat ggctaatttt 1740
tgtattttta gtagaaatgg ggtttcgtca tgttggccag gctggtctcg aactcctggc 1800

```
ctaggtgatc cacccgcctc gacctcccaa agtgctggga ttacaggcat gagccaccat   1860
gcccagtcga tatctcactt tttattttgc catggatgag agtcctgggt gtgaggaaca   1920
cctcccacca ggctagaggc aactgcccag gaaggactgt gcttccgtca cctctaaatc   1980
ccttgcagat ccttgataaa tgcctcatga agaccaatct cttgaatccc atatctaccc   2040
agaattaact ccattccagt ctctgcatgt aatcagtttt atccacagaa acattttcat   2100
tttaggaaat ccctggtttt aagtatcaat ccttgttcag ctggacaata tgaatctttt   2160
ccactgaagt tagggatgac tgtgattttc agaacacgtc cagaattttt catcaagaag   2220
gtagcttgag cctgaaatgc aaaacccatg gaggaattct gaagccattg tctccttgag   2280
taccaacagg gtcagggaag actgggcctc ctgaatttat tattgttctt taagaattac   2340
aggttgaggt agttgatggt ggtaaacatt ctctcaggag acaataactc cagtgatgtt   2400
cttcaaagat tttagcaaaa acagagtaaa tagcattctc tatcaatata taaatttaaa   2460
aaactatctt tttgcttaca gttttaaatt ctgaacaatt ctctcttata tgtgtattgc   2520
taatcattaa ggtattattt tttccacata taaagctttg tctttttgtt gttgttgttg   2580
tttttaagat ggagtttccc tctgttgcca ggctagagtg cagtggcatg atctcggctt   2640
actgcaacct ttgcctccca ggttcaagcg attcttctgc ctcagcctcc cgagtagctg   2700
ggaccacagg tgcctaccac catgccaggc taatttttgt atttttagta aagacagggt   2760
ttcaccatat tggccaggct ggtctcgaac tcctgacctt gtgatctgcc cgcctccatt   2820
tttgttgtta tttttttgaga aagatagata tgaggtttag agagggatga agaggtgaga   2880
gtaagccttg tgttagtcag aactctgtgt tgtgaatgtc attcacaaca gaaaacccaa   2940
aatattatgc aaactactgt aagcaagaaa aataaaggaa aaatggaaac atttattcct   3000
ttgcataata gaaattacca gagttgttct gtctttagat aaggtttgaa ccaaagctca   3060
aaacaatcaa gaccctttc tgtatgtcct tctgttctgc cttccgcagt gtaggcttta   3120
ccctcaggtg ctacacagta tagttctagg gtttccctcc cgatatcaaa aagactgtgg   3180
cctgcccagc tctcgtatcc ccaagccaca ccatctggct aaatggacat catgttttct   3240
ggtgatgccc aaagaggaga gaggaagctc tctttcccag atgccccagc aagtgtaacc   3300
ttgcatctca ttgctctggc tgagttgtgt gcctgtttct gaccaatcac tgagtcagga   3360
ggatgaaata ttcatattga cttaattgca gcttaagtta ggggtatgta gaggtatttt   3420
ccctaaagca aaattgggac actgttatca gaaataggag agtggatgat agatgcaaaa   3480
taatacctgt ccacaacaaa ctcttaatgc tgtgtttgag ctttcatgag tttcccagag   3540
agacatagct ggaaaattcc tattgatttt ctctaaaatt tcaacaagta gctaaagtct   3600
ggctatgctc acagtctcac atctggttgg ggtgggctcc ttacagaaca cgctttcaca   3660
gttaccctaa actctctggg gcagggttat tcctttgtgg aaccagaggc acagagagag   3720
tcaactgagg ccaaaagagg cctgagagaa actgaggtca agatttcagg attaatggtc   3780
ctgtgatgct ttgaagtaca attgtggatt tgtccaattc tctttagttc tgtcagcttt   3840
tgcttcatat attttagcgc tctattatta gatatataca tgtttagtat tatgtcttat   3900
tggtgcattt actctcttat cattatgtaa tgtccttctt tatctgtgat aattttctgt   3960
gttctgaagt ctactttgtc taaaaataac atacgcactc aacttccttt tctttcttcc   4020
ttcctttctt tcttccttcc tttctttctc tctctctctc tttccttcct tccttcctcc   4080
ttttctttct ctctctctct ctctctcttt ttttgacaga ctctcgttct gtggccctgg   4140
```

```
ctggagttca gtggtgtgat cttggctcac tgctacctct accatgagca attctcctgc   4200

ctcagcctcc caagtagctg gaactacagg ctcatgccac tgcgcccagc taatttttgt   4260

atttttcgta gagacggggt ttcaccacat tcgtcaggtt ggtttcaaac tcctgacttt   4320

gtgatccacc cgcctcggcc tcccaaagtg ctgggattac aggcatgagc catcacacct   4380

ggtcaacttt cttttgatta gtgtttttgt ggtatatctt tttccatcat gttactttaa   4440

atatatctat attattgtat ttaaaatgtg tttcttacag actgcatgta gttgggtata   4500

atttttatcc agtctaaaaa tatctgtctt ttaattggtg tttagacaat ttatatttaa   4560

taaaattgtt gaatttaa                                                 4578


<210> SEQ ID NO 61
<211> LENGTH: 658
<212> TYPE: PRT
<213> ORGANISM: Homo sapiens

<400> SEQUENCE: 61

Met Asp Arg Gly Thr Leu Pro Leu Ala Val Ala Leu Leu Leu Ala Ser
1               5                   10                  15

Cys Ser Leu Ser Pro Thr Ser Leu Ala Glu Thr Val His Cys Asp Leu
            20                  25                  30

Gln Pro Val Gly Pro Glu Arg Gly Glu Val Thr Tyr Thr Thr Ser Gln
        35                  40                  45

Val Ser Lys Gly Cys Val Ala Gln Ala Pro Asn Ala Ile Leu Glu Val
    50                  55                  60

His Val Leu Phe Leu Glu Phe Pro Thr Gly Pro Ser Gln Leu Glu Leu
65                  70                  75                  80

Thr Leu Gln Ala Ser Lys Gln Asn Gly Thr Trp Pro Arg Glu Val Leu
                85                  90                  95

Leu Val Leu Ser Val Asn Ser Ser Val Phe Leu His Leu Gln Ala Leu
            100                 105                 110

Gly Ile Pro Leu His Leu Ala Tyr Asn Ser Ser Leu Val Thr Phe Gln
        115                 120                 125

Glu Pro Pro Gly Val Asn Thr Thr Glu Leu Pro Ser Phe Pro Lys Thr
    130                 135                 140

Gln Ile Leu Glu Trp Ala Ala Glu Arg Gly Pro Ile Thr Ser Ala Ala
145                 150                 155                 160

Glu Leu Asn Asp Pro Gln Ser Ile Leu Leu Arg Leu Gly Gln Ala Gln
                165                 170                 175

Gly Ser Leu Ser Phe Cys Met Leu Glu Ala Ser Gln Asp Met Gly Arg
            180                 185                 190

Thr Leu Glu Trp Arg Pro Arg Thr Pro Ala Leu Val Arg Gly Cys His
        195                 200                 205

Leu Glu Gly Val Ala Gly His Lys Glu Ala His Ile Leu Arg Val Leu
    210                 215                 220

Pro Gly His Ser Ala Gly Pro Arg Thr Val Thr Val Lys Val Glu Leu
225                 230                 235                 240

Ser Cys Ala Pro Gly Asp Leu Asp Ala Val Leu Ile Leu Gln Gly Pro
                245                 250                 255

Pro Tyr Val Ser Trp Leu Ile Asp Ala Asn His Asn Met Gln Ile Trp
            260                 265                 270

Thr Thr Gly Glu Tyr Ser Phe Lys Ile Phe Pro Glu Lys Asn Ile Arg
        275                 280                 285

Gly Phe Lys Leu Pro Asp Thr Pro Gln Gly Leu Leu Gly Glu Ala Arg
```

-continued

```
    290                 295                 300

Met Leu Asn Ala Ser Ile Val Ala Ser Phe Val Glu Leu Pro Leu Ala
305                 310                 315                 320

Ser Ile Val Ser Leu His Ala Ser Ser Cys Gly Gly Arg Leu Gln Thr
                325                 330                 335

Ser Pro Ala Pro Ile Gln Thr Thr Pro Pro Lys Asp Thr Cys Ser Pro
            340                 345                 350

Glu Leu Leu Met Ser Leu Ile Gln Thr Lys Cys Ala Asp Asp Ala Met
        355                 360                 365

Thr Leu Val Leu Lys Lys Glu Leu Val Ala His Leu Lys Cys Thr Ile
    370                 375                 380

Thr Gly Leu Thr Phe Trp Asp Pro Ser Cys Glu Ala Glu Asp Arg Gly
385                 390                 395                 400

Asp Lys Phe Val Leu Arg Ser Ala Tyr Ser Ser Cys Gly Met Gln Val
                405                 410                 415

Ser Ala Ser Met Ile Ser Asn Glu Ala Val Val Asn Ile Leu Ser Ser
            420                 425                 430

Ser Ser Pro Gln Arg Lys Lys Val His Cys Leu Asn Met Asp Ser Leu
        435                 440                 445

Ser Phe Gln Leu Gly Leu Tyr Leu Ser Pro His Phe Leu Gln Ala Ser
    450                 455                 460

Asn Thr Ile Glu Pro Gly Gln Gln Ser Phe Val Gln Val Arg Val Ser
465                 470                 475                 480

Pro Ser Val Ser Glu Phe Leu Leu Gln Leu Asp Ser Cys His Leu Asp
                485                 490                 495

Leu Gly Pro Glu Gly Gly Thr Val Glu Leu Ile Gln Gly Arg Ala Ala
            500                 505                 510

Lys Gly Asn Cys Val Ser Leu Leu Ser Pro Ser Pro Glu Gly Asp Pro
        515                 520                 525

Arg Phe Ser Phe Leu Leu His Phe Tyr Thr Val Pro Ile Pro Lys Thr
    530                 535                 540

Gly Thr Leu Ser Cys Thr Val Ala Leu Arg Pro Lys Thr Gly Ser Gln
545                 550                 555                 560

Asp Gln Glu Val His Arg Thr Val Phe Met Arg Leu Asn Ile Ile Ser
                565                 570                 575

Pro Asp Leu Ser Gly Cys Thr Ser Lys Gly Leu Val Leu Pro Ala Val
            580                 585                 590

Leu Gly Ile Thr Phe Gly Ala Phe Leu Ile Gly Ala Leu Leu Thr Ala
        595                 600                 605

Ala Leu Trp Tyr Ile Tyr Ser His Thr Arg Ser Pro Ser Lys Arg Glu
    610                 615                 620

Pro Val Val Ala Val Ala Ala Pro Ala Ser Ser Glu Ser Ser Ser Thr
625                 630                 635                 640

Asn His Ser Ile Gly Ser Thr Gln Ser Thr Pro Cys Ser Thr Ser Ser
                645                 650                 655

Met Ala


<210> SEQ ID NO 62
<211> LENGTH: 625
<212> TYPE: PRT
<213> ORGANISM: Homo sapiens

<400> SEQUENCE: 62

Met Asp Arg Gly Thr Leu Pro Leu Ala Val Ala Leu Leu Leu Ala Ser
```

-continued

```
1               5                   10                  15

Cys Ser Leu Ser Pro Thr Ser Leu Ala Glu Thr Val His Cys Asp Leu
            20                  25                  30

Gln Pro Val Gly Pro Glu Arg Gly Glu Val Thr Tyr Thr Thr Ser Gln
        35                  40                  45

Val Ser Lys Gly Cys Val Ala Gln Ala Pro Asn Ala Ile Leu Glu Val
    50                  55                  60

His Val Leu Phe Leu Glu Phe Pro Thr Gly Pro Ser Gln Leu Glu Leu
65                  70                  75                  80

Thr Leu Gln Ala Ser Lys Gln Asn Gly Thr Trp Pro Arg Glu Val Leu
                85                  90                  95

Leu Val Leu Ser Val Asn Ser Ser Val Phe Leu His Leu Gln Ala Leu
            100                 105                 110

Gly Ile Pro Leu His Leu Ala Tyr Asn Ser Ser Leu Val Thr Phe Gln
        115                 120                 125

Glu Pro Pro Gly Val Asn Thr Thr Glu Leu Pro Ser Phe Pro Lys Thr
    130                 135                 140

Gln Ile Leu Glu Trp Ala Ala Glu Arg Gly Pro Ile Thr Ser Ala Ala
145                 150                 155                 160

Glu Leu Asn Asp Pro Gln Ser Ile Leu Leu Arg Leu Gly Gln Ala Gln
                165                 170                 175

Gly Ser Leu Ser Phe Cys Met Leu Glu Ala Ser Gln Asp Met Gly Arg
            180                 185                 190

Thr Leu Glu Trp Arg Pro Arg Thr Pro Ala Leu Val Arg Gly Cys His
        195                 200                 205

Leu Glu Gly Val Ala Gly His Lys Glu Ala His Ile Leu Arg Val Leu
    210                 215                 220

Pro Gly His Ser Ala Gly Pro Arg Thr Val Thr Val Lys Val Glu Leu
225                 230                 235                 240

Ser Cys Ala Pro Gly Asp Leu Asp Ala Val Leu Ile Leu Gln Gly Pro
                245                 250                 255

Pro Tyr Val Ser Trp Leu Ile Asp Ala Asn His Asn Met Gln Ile Trp
            260                 265                 270

Thr Thr Gly Glu Tyr Ser Phe Lys Ile Phe Pro Glu Lys Asn Ile Arg
        275                 280                 285

Gly Phe Lys Leu Pro Asp Thr Pro Gln Gly Leu Leu Gly Glu Ala Arg
    290                 295                 300

Met Leu Asn Ala Ser Ile Val Ala Ser Phe Val Glu Leu Pro Leu Ala
305                 310                 315                 320

Ser Ile Val Ser Leu His Ala Ser Ser Cys Gly Gly Arg Leu Gln Thr
                325                 330                 335

Ser Pro Ala Pro Ile Gln Thr Thr Pro Pro Lys Asp Thr Cys Ser Pro
            340                 345                 350

Glu Leu Leu Met Ser Leu Ile Gln Thr Lys Cys Ala Asp Asp Ala Met
        355                 360                 365

Thr Leu Val Leu Lys Lys Glu Leu Val Ala His Leu Lys Cys Thr Ile
    370                 375                 380

Thr Gly Leu Thr Phe Trp Asp Pro Ser Cys Glu Ala Glu Asp Arg Gly
385                 390                 395                 400

Asp Lys Phe Val Leu Arg Ser Ala Tyr Ser Ser Cys Gly Met Gln Val
                405                 410                 415

Ser Ala Ser Met Ile Ser Asn Glu Ala Val Val Asn Ile Leu Ser Ser
            420                 425                 430
```

```
Ser Ser Pro Gln Arg Lys Lys Val His Cys Leu Asn Met Asp Ser Leu
        435                 440                 445

Ser Phe Gln Leu Gly Leu Tyr Leu Ser Pro His Phe Leu Gln Ala Ser
    450                 455                 460

Asn Thr Ile Glu Pro Gly Gln Gln Ser Phe Val Gln Val Arg Val Ser
465                 470                 475                 480

Pro Ser Val Ser Glu Phe Leu Leu Gln Leu Asp Ser Cys His Leu Asp
                485                 490                 495

Leu Gly Pro Glu Gly Gly Thr Val Glu Leu Ile Gln Gly Arg Ala Ala
            500                 505                 510

Lys Gly Asn Cys Val Ser Leu Leu Ser Pro Ser Pro Glu Gly Asp Pro
        515                 520                 525

Arg Phe Ser Phe Leu Leu His Phe Tyr Thr Val Pro Ile Pro Lys Thr
    530                 535                 540

Gly Thr Leu Ser Cys Thr Val Ala Leu Arg Pro Lys Thr Gly Ser Gln
545                 550                 555                 560

Asp Gln Glu Val His Arg Thr Val Phe Met Arg Leu Asn Ile Ile Ser
                565                 570                 575

Pro Asp Leu Ser Gly Cys Thr Ser Lys Gly Leu Val Leu Pro Ala Val
            580                 585                 590

Leu Gly Ile Thr Phe Gly Ala Phe Leu Ile Gly Ala Leu Leu Thr Ala
        595                 600                 605

Ala Leu Trp Tyr Ile Tyr Ser His Thr Arg Glu Tyr Pro Arg Pro Pro
    610                 615                 620

Gln
625
```

<210> SEQ ID NO 63
<211> LENGTH: 2606
<212> TYPE: DNA
<213> ORGANISM: Homo sapiens

<400> SEQUENCE: 63

```
ccgggcctca ctcgggcccc gcggccgcct ttataaggcg gcgggggtgg tggcccgggc     60

cgcgttgcgc tcccgccact ccgcgcccgc tatcctggct ccgtgctccc acgcgcttgt    120

gcctggacgg accctcgcca gtgctctgcg caggattgga acatcagtta acatctgacc    180

actgccagcc cacccccctcc cacccacgtc gattgcatct ctgggctcca gggataaagc    240

aggtcttggg gtgcaccatg atttcaccat tcttagtact ggccattggc acctgcctta    300

ctaactcctt agtgccagag aaagagaaag accccaagta ctggcgagac caagcgcaag    360

agacactgaa atatgccctg gagcttcaga agctcaacac caacgtggct aagaatgtca    420

tcatgttcct gggagatggg atgggtgtct ccacagtgac ggctgcccgc atcctcaagg    480

gtcagctcca ccacaaccct ggggaggaga ccaggctgga gatggacaag ttccccttcg    540

tggccctctc caagacgtac aacaccaatg cccaggtccc tgacagcgcc ggcaccgcca    600

ccgcctacct gtgtggggtg aaggccaatg agggcaccgt gggggtaagc gcagccactg    660

agcgttcccg gtgcaacacc acccagggga acgaggtcac ctccatcctg cgctgggcca    720

aggacgctgg gaaatctgtg ggcattgtga ccaccacgag agtgaaccat gccacccccca    780

gcgccgccta cgcccactcg gctgaccggg actggtactc agacaacgag atgcccccctg    840

aggccttgag ccagggctgt aaggacatcg cctaccagct catgcataac atcagggaca    900

ttgacgtgat catgggggggt ggccggaaat acatgtaccc caagaataaa actgatgtgg    960
```

-continued

```
agtatgagag tgacgagaaa gccaggggca cgaggctgga cggcctggac ctcgttgaca   1020
cctggaagag cttcaaaccg agatacaagc actcccactt catctggaac cgcacggaac   1080
tcctgaccct tgacccccac aatgtggact acctattggg tctcttcgag ccaggggaca   1140
tgcagtacga gctgaacagg aacaacgtga cggacccgtc actctccgag atggtggtgg   1200
tggccatcca gatcctgcgg aagaacccca aaggcttctt cttgctggtg gaaggaggca   1260
gaattgacca cgggcaccat gaaggaaaag ccaagcaggc cctgcatgag gcggtggaga   1320
tggaccgggc catcgggcag gcaggcagct tgacctcctc ggaagacact ctgaccgtgg   1380
tcactgcgga ccattcccac gtcttcacat ttggtggata caccccccgt ggcaactcta   1440
tctttggtct ggcccccatg ctgagtgaca cagacaagaa gcccttcact gccatcctgt   1500
atggcaatgg gcctggctac aaggtggtgg gcggtgaacg agagaatgtc tccatggtgg   1560
actatgctca caacaactac caggcgcagt ctgctgtgcc cctgcgccac gagacccacg   1620
gcggggagga cgtggccgtc ttctccaagg gccccatggc gcacctgctg cacggcgtcc   1680
acgagcagaa ctacgtcccc cacgtgatgg cgtatgcagc ctgcatcggg gccaacctcg   1740
gccactgtgc tcctgccagc tcggcaggca gccttgctgc aggcccccctg ctgctcgcgc   1800
tggccctcta ccccctgagc gtcctgttct gagggcccag ggcccgggca cccacaagcc   1860
cgtgacagat gccaacttcc cacacggcag cccccccctc aaggggcagg gaggtggggg   1920
cctcctcagc ctctgcaact gcaagaaagg ggacccaaga aaccaaagtc tgccgcccac   1980
ctcgctcccc tctggaatct tccccaaggg ccaaacccac ttctggcctc cagcctttgc   2040
tccctccccg ctgccctttg gccaacaggg tagatttctc ttgggcaggc agagagtaca   2100
gactgcagac attctcaaag cctcttattt ttctagcgaa cgtatttctc cagacccaga   2160
ggccctgaag cctccgtgga acattctgga tctgaccctc ccagtctcat ctcctgaccc   2220
tcccactccc atctccttac ctctggaacc ccccaggccc tacaatgctc atgtccctgt   2280
ccccaggccc agccctcctt caggggagtt gaggtctttc tcctcaggac aaggccttgc   2340
tcactcactc actccaagac caccagggtc ccaggaagcc ggtgcctggg tggccatcct   2400
acccagcgtg gcccaggccg ggaagagcca cctggcaggg ctcacactcc tgggctctga   2460
acacacacgc cagctcctct ctgaagcgac tctcctgttt ggaacggcaa aaaaaaattt   2520
ttttttctct ttttggtggt ggttaaaagg gaacacaaaa catttaaata aaactttcca   2580
aatatttccg aggacaaaaa aaaaaa                                        2606
```